US012806274B2

(12) United States Patent
Mandai et al.

(10) Patent No.: US 12,806,274 B2
(45) Date of Patent: Nov. 24, 2026

(54) MEDIUM FOR TISSUE FOR TRANSPLANTATION

(71) Applicants: RACTHERA Co., Ltd., Tokyo (JP); Riken, Saitama (JP)

(72) Inventors: Michiko Mandai, Wako (JP); Masayo Takahashi, Saitama (JP); Tatsuya Kamei, Kobe (JP); Keiichi Ono, Suita (JP); Kenji Watari, Kobe (JP); Atsushi Kuwahara, Kobe (JP)

(73) Assignees: RACTHERA Co., Ltd., Tokyo (JP); Riken, Saitama (JP)

( * ) Notice: Subject to any disclaimer, the term of this patent is extended or adjusted under 35 U.S.C. 154(b) by 606 days.

(21) Appl. No.: 18/025,037

(22) PCT Filed: Sep. 10, 2021

(86) PCT No.: PCT/JP2021/033386

§ 371 (c)(1),
(2) Date: Mar. 7, 2023

(87) PCT Pub. No.: WO2022/054924

PCT Pub. Date: Mar. 17, 2022

(65) Prior Publication Data

US 2023/0310614 A1 Oct. 5, 2023

(30) Foreign Application Priority Data

Sep. 11, 2020 (JP) ................................ 2020-153248

(51) Int. Cl.
*A61K 47/36* (2006.01)
*A61K 35/30* (2015.01)
*A61P 27/02* (2006.01)

(52) U.S. Cl.
CPC .............. *A61K 47/36* (2013.01); *A61K 35/30* (2013.01); *A61P 27/02* (2018.01)

(58) Field of Classification Search
CPC ........ A61K 47/42; A61K 27/52; A61K 31/30; A61L 27/22; A61L 27/383
See application file for complete search history.

(56) References Cited

U.S. PATENT DOCUMENTS

| | | | |
|---|---|---|---|
| 2013/0189230 A1 | 7/2013 | Shoichet et al. | |
| 2021/0155895 A1* | 5/2021 | Nasonkin ........... | G01N 33/5088 |

FOREIGN PATENT DOCUMENTS

| | | | |
|---|---|---|---|
| CA | 3074442 | A1 | 3/2019 |
| JP | 2005-517468 | A | 6/2005 |
| WO | 03/068053 | A2 | 8/2003 |
| WO | 2011/055855 | A1 | 5/2011 |
| WO | 2012/173207 | A1 | 12/2012 |
| WO | 2013/077425 | A1 | 5/2013 |
| WO | 2015/025967 | A1 | 2/2015 |
| WO | 2015/053375 | A1 | 4/2015 |
| WO | 2015/053376 | A1 | 4/2015 |
| WO | 2015/068505 | A1 | 5/2015 |
| WO | 2016/063985 | A1 | 4/2016 |
| WO | 2016/063986 | A1 | 4/2016 |
| WO | 2017/043605 | A1 | 3/2017 |
| WO | 2017/183732 | A1 | 10/2017 |
| WO | 2019/017491 | A1 | 1/2019 |
| WO | 2019/017492 | A1 | 1/2019 |
| WO | 2019/050015 | A1 | 3/2019 |
| WO | 2019/054514 | A1 | 3/2019 |
| WO | 2019/054515 | A1 | 3/2019 |
| WO | 2020/184720 | A1 | 9/2020 |

OTHER PUBLICATIONS

Ballios et al., "A hydrogel-based stem cell delivery system to treat retinal degenerative diseases", Biomaterials, vol. 31, 2010, pp. 2555-2564.
Kuwahara et al., "Generation of a ciliary margin-like stem cell niche from self-organizing human retinal tissue," Nature Communications, 6, Article No. 6286 (2015).
Mandai et al., "Autologous Induced Stem-Cell-Derived Retinal Cells for Macular Degeneration," The New England Journal of Medicine, 376(11): 1038-1046 (2017).
Nakazawa et al., "Tumor Necrosis Factor-alpha Mediates Photoreceptor Death in a Rodent Model of Retinal Detachment", Investigative Ophthalmology & Visual Science, 52 (3): 138 (2011).
Meyer et al., "Optic Vesicle-like Structures Derived from Human Pluripotent Stem Cells Facilitate a Customized Approach to Retinal Disease Treatment," Stem Cells, 29 (8): 1206-1218 (2011).
Reichman et al., "From confluent human iPS cells to self-forming neural retina and retinal pigmented epithelium," PNAS, 111 (23), p. 8518-p. 8523 (2014).
Zhong et al., "Generation of three-dimensional retinal tissue with functional photoreceptors from human iPSCs," Nature Communications, 5: 4047 (2014).
Kamao et al., "Characterization of Human Induced Pluripotent Stem Cell-Derived Retinal Pigment Epithelium Cell Sheets Aiming for Clinical Application", Stem Cell Reports, 2: 205-218 (2014).

(Continued)

*Primary Examiner* — Zohreh A Fay
(74) *Attorney, Agent, or Firm* — Morgan, Lewis & Bockius LLP

(57) ABSTRACT

An object of the present invention is to provide a vehicle and a composition for transplantation comprising retinal tissue and the vehicle, which are for the treatment of retinal degenerative diseases such as retinitis pigmentosa (RP) and are suitable for the subretinal transplantation of retinal tissue. The vehicle for transplantation of the present invention is a vehicle for transplantation for subretinally transplanting retinal tissue, the vehicle having a viscosity of 5 to 500 mPa·s at a shear rate of 2 (1/s) at 25° C., and comprising hyaluronic acid and a pharmaceutically acceptable aqueous liquid. The composition for transplantation of the present invention comprises transplant retinal tissue and the vehicle for transplantation of the present invention.

22 Claims, 14 Drawing Sheets

(56) References Cited

OTHER PUBLICATIONS

Nakano et al., "Self-Formation of Optic Cups and Storable Stratified Neural Retina from Human ESCs," Cell Stem Cell, 10 (6): 771-785 (2012).
McLelland et al., "Transplanted hESC-Derived Retina Organoid Sheets Differentiate, Integrate, and Improve Visual Function in Retinal Degenerate Rats," Investigative Ophthalmology & Visual Science, 59 (6): 2586-2603 (2018).
Kuwahara et al., "Preconditioning the Initial State of Feeder-free Human Pluripotent Stem Cells Promotes Self-formation of Three-dimensional Retinal Tissue", Scientific Reports, 9 (1):18936 (2019).
Lamba et al., "Transplantation of Human Embryonic Stem Cell-Derived Photoreceptors Restores Some Visual Function in Crx-Deficient Mice," Cell Stem Cell, 4: 73-79 (2009).
Zhu et al., "Immunosuppression via Loss of IL2rg Enhances Long-Term Functional Integration of hESC-Derived Photoreceptors in the Mouse Retina," Cell Stem Cell, 20: 374-384 (2017).
Boucherie et al., "Brief report: self-organizing neuroepithelium from human pluripotent stem cells facilitates derivation of photoreceptors", Stem Cells, 31 (2): 408-14 (2013).
Lamba et al., "Generation, purification and transplantation of photoreceptors derived from human induced pluripotent stem cells," PLoS One, 5 (1): e8763 (2010).
Gonzalez-Cordero et al., "Photoreceptor precursors derived from three-dimensional embryonic stem cell cultures integrate and mature within adult degenerate retina", Nat Biotechnology, 31 (8) (2013).
Tucker et al., "Use of a Synthetic Xeno-Free Culture Substrate for Induced Pluripotent Stem Cell Induction and Retinal Differentiation," Stem Cells Translational Medicine, 2: 16-24 (2013).
Mellough et al., "IGF-1 Signaling Plays an Important Role in the Formation of Three-Dimensional Laminated Neural Retina and Other Ocular Structures From Human Embryonic Stem Cells," Stem Cells, 233: 2416-2430 (2015).
Shirai et al., "Transplantation of human embryonic stem cell-derived retinal tissue in two primate models of retinal degeneration," PNAS, 113 (1): E81-E90 (2015).
Wahlin et al., "Photoreceptor Outer Segment-like Structures in Long-Term 3D Retinas from Human Pluripotent Stem Cells," Scientific Reports, 7: 766 (2017).
Hallam et al., "Human-Induced Pluripotent Stem Cells Generate Light Responsive Retinal Organoids with Variable and Nutrient-Dependent Efficiency," Stem Cells, 36: 1535-1551 (2018).
Gagliardi et al., "Characterization and Transplantation of CD73-Positive Photoreceptors Isolated from Human iPSC-Derived Retinal Organoids," Stem Cell Reports, 11: 665-680 (2018).
DiStefano et al., "Accelerated and Improved Differentiation of Retinal Organoids from Pluripotent Stem Cells in Rotating-Wall Vessel Bioreactors," Stem Cell Reports, 10: 300-313 (2018).
Mitrousis et al., "Hydrogel-mediated co-transplantation of retinal pigmented epithelium and photoreceptors restores vision in an animal model of advanced retinal degeneration," Biomaterials, 257: 120233 (2020).
Tian et al., "Screening and optimization of potential injection vehicles for storage of retinal pigment epithelial stem cell before transplantation," Journal of Tissue Engineering and Regenerative Medicine, 13: 76-86 (2019).
Humayun et al., "Human Neural Retinal Transplantation," Investigative Ophthalmology & Visual Science, 41 (10): 3100-3106 (2000).
Assawachananont et al., "Transplantation of Embryonic and Induced Pluripotent Stem Cell-Derived 3D Retinal Sheets Into Retinal Degenerative Mice," Stem Cell Reports, 2: 662-674 (2014).
International Search Report issued in counterpart International Patent Application No. PCT/JP2021/033386 dated Oct. 26, 2021.
International Preliminary Report on Patentability and Written Opinion issued in counterpart PCT/JP2021/033386 dated Mar. 23, 2023.
U.S. Appl. No. 18/025,036, filed Mar. 7, 2023.

* cited by examiner

| SAMPLE | MAJOR AXIS μm | MINOR AXIS μm | HEIGHT μm |
|---|---|---|---|
| CAP LARGE | 1606 | 1051 | 640 |
| CAP MEDIUM | 1170 | 592 | 440 |
| CAP SMALL | 1132 | 462 | 258 |
| AVERAGE | 1184 | 646 | 421 |

MEDIUM FOR TISSUE FOR TRANSPLANTATION

TECHNICAL FIELD

The present invention relates to a vehicle that is used in subretinally transplanting retinal tissue into an eyeball, and a composition for transplantation comprising retinal tissue and the vehicle, etc.

BACKGROUND ART

The transplantation of retinal tissue is considered as promising treatment for patients having a disease involving the degeneration or injury of a retina, such as retinitis pigmentosa or age-related macular degeneration, and research and development are underway. For example, it is possible to produce retinal tissue containing photoreceptor cells by differentiation from pluripotent stem cells (Non Patent Literature 1). Also, a case in which an autologous RPE cell sheet produced from pluripotent stem cells was transplanted to a patient has been reported as a method for subretinally transplanting retinal tissue into an eyeball (Non Patent Literature 2). In Non Patent Literature 1, it has been reported that a RPE cell sheet was successfully engrafted by aspirating RPE tissue to the inside of a 20 gauge Surflo needle, then inserting the Surflo needle to subretinal space in an eyeball, and discharging the RPE tissue from the tip of the Surflo needle to the subretinal space. However, a vehicle used in transplanting the RPE cell sheet is not described.

For the transplantation of retinal tissue, particularly, retinal tissue containing photoreceptor cells, it is necessary to accurately insert retinal tissue to be transplanted to an affected part in need of repair, and engraft it. Therefore, a suitable vehicle that enables transplantation surgery of retinal tissue to be performed without depending on physician's technique has been demanded.

Meanwhile, in Patent Literature 1, a device for subretinally transplanting an implant (retina cell graft) is disclosed. Although it states that an aqueous hyaluronic acid solution is used therein, neither specific retinal tissue nor the concentration of hyaluronic acid is described. Non Patent Literature 3 states that vehicles for preserving RPE stem cells before transplantation were screened and optimized, and influence on the survival, attachment, distribution, proliferation and differentiation potency into RPE cells, of RPE stem cells was examined as to each vehicle. It states that in the case of using a 0.2% hyaluronic acid solution as a preservation vehicle for RPE stem cells, the favorable distribution and proliferation of RPE stem cells as well as cobblestone formation unique to matured RPE cells and the expression of RPE cell markers have been found to be promoted after preservation for 96 hours. However, in Non Patent Literature 3, an effect in the case of actual use in transplantation surgery is not described.

It has been further reported that in the case of subretinally injecting hyaluronic acid, retinal detachment occurs (see Non Patent Literature 4).

As described above, a suitable vehicle for subretinally transplanting retinal tissue has not yet been established.

CITATION LIST

Patent Literature

Patent Literature 1: Japanese Unexamined Patent Publication No. 2005-517468

Non Patent Literature

Non Patent Literature 1: A. Kuwahara et al., "Generation of a ciliary margin-like stem cell niche from self-organizing human retinal tissue" Nature Communications, 6, Article number: 6286 (2015).

Non Patent Literature 2: M. Mandai et al., "Autologous InducedStem-Cell-Derived Retinal Cells for Macular Degeneration", The New England Journal of Medicine, 2017, 376(11), p. 1038-1046.

Non Patent Literature 3: Y. Tian et al., "Screening and optimization of potential injection vehicles for storage of retinalpigment epithelial stem cell before transplantation", J Tissue Eng Regen Med. 2019; 13(1): p 76-86.

Non Patent Literature 4: T. Nakazawa, et al., "Tumor Necrosis Factor-Mediates Photoreceptor Death in a Rodent Model of Retinal Detachment" Investigative Ophthalmology & Visual Science, March 2011, Vol. 52, No. 3, p 1384-1391

SUMMARY OF INVENTION

Technical Problem

An object of the present invention is to provide a vehicle and a composition for transplantation comprising retinal tissue and the vehicle, which are for the treatment of retinal degenerative diseases such as retinitis pigmentosa (RP) and are suitable for the subretinal transplantation of retinal tissue.

Solution to Problem

In order to attain the object, the present inventors have conducted diligent studies on a vehicle for transplantation that is used for subretinally transplanting retinal tissue, and consequently completed the present invention by finding a vehicle for transplantation that enables retinal tissue, specifically, a neural retina sheet, to be aspirated to and discharged from an administration instrument (tip for transplantation), and is useful for subretinally transplanting it to a recipient while appropriately maintaining an apical surface/basal surface direction.

Specifically, the present invention provides the following.

[1]

A vehicle for transplantation for subretinally transplanting retinal tissue, the vehicle having a viscosity of 5 to 500 mPa·s at a shear rate of 2 (1/s) at 25° C., and comprising hyaluronic acid and a pharmaceutically acceptable aqueous liquid.

[2]

The vehicle for transplantation according to [1], wherein the viscosity at a shear rate of 2 (1/s) at 25° C. is from 10 to 100 mPa·s.

[3]

The vehicle for transplantation according to [1] or [2], wherein viscosity at a shear rate of 1000 (1/s) at 25° C. is 100 mPa·s or less, and a viscosity difference between viscosity at a shear rate of 1 (1/s) and viscosity at a shear rate of 10 (1/s) is 100 mPa·s or less.

[4]

The vehicle for transplantation according to any of [1] to [3], wherein pH is from 7.0 to 7.5.

[5]

The vehicle for transplantation according to any of [1] to [4], wherein the pharmaceutically acceptable aqueous liquid is a balanced salt solution.

[6]

The vehicle for transplantation according to any of [1] to [5], comprising 0.15 w/v % to 1.50 w/v % of hyaluronic acid having an average molecular weight of 500,000 to 3,900,000.

[7]

The vehicle for transplantation according to any of [1] to [6], further comprising chondroitin sulfate.

[8]

The vehicle for transplantation according to [7], comprising 0.3 w/v % to 1.0 w/v % of chondroitin sulfate.

[9]

The vehicle for transplantation according to any of [1] to [8], comprising neither an antimicrobial agent nor an antiseptic.

[10]

A composition for transplantation comprising a transplant retinal tissue and the vehicle for transplantation according to any of [1] to [9].

[11]

The composition for transplantation according to [10], wherein the transplant retinal tissue is a transplant neural retina sheet comprising a neural retinal layer.

[12]

The composition for transplantation according to [11], wherein the transplant neural retina sheet has a front surface and a back surface, wherein the front surface constitutes an apical surface containing a neural retinal layer, the back surface constitutes a basal surface adjacent to an inner layer of the neural retina, a thickness from the front surface to the back surface of the transplant neural retina sheet is from 100 μm to 1000 μm, a major axis of the transplant neural retina sheet is from 600 μm to 2500 μm, and a minor axis of the transplant neural retina sheet is from 200 μm to 1500 μm.

[13]

The composition for transplantation according to [12], wherein the front surface has a smooth shape with less change in curvature, and the back surface has an irregular shape with large change in curvature.

[14]

The composition for transplantation according to any of [11] to [13], comprising 1 to 30 of the transplant neural retina sheets and 5 to 500 μl of the vehicle for transplantation.

[15]

The composition for transplantation according to any of [11] to [14], wherein the transplant neural retina sheet is a neural retina sheet (1) being derived from a pluripotent stem cell, (2) having a three-dimensional structure, (3) comprising a neural retinal layer having a plurality of layer structures including a photoreceptor layer and an inner layer, (4) the photoreceptor layer comprising one or more cells selected from the group consisting of a photoreceptor progenitor cell and a photoreceptor cell, (5) the inner layer comprising one or more cells selected from the group consisting of a retinal progenitor cell, a ganglion cell, an amacrine cell and a bipolar cell, (6) the surface of the neural retinal layer having an apical surface, (7) the inner layer being present inside the photoreceptor layer present along the apical surface, (8) the area of the apical surface of the neural retinal layer being 50% or more with respect to the total area of the surface of the neural retina sheet, (9) the area of a continuous epithelium structure being 80% or more with respect to the total area of the apical surface of the neural retinal layer, and

(10) the expression of neural retina-related cell-related gene being found and the expression of non-neural retina-related cell-related gene being not found in the transplant neural retina sheet, wherein the non-neural retina-related cell-related gene comprising one or more genes selected from the group consisting of brain and spinal cord tissue marker gene and eyeball-related tissue marker gene.

[16]

The composition for transplantation according to any of [11] to [15], wherein the transplant neural retina sheet (1) has been isolated from a cell aggregate containing a neural retinal layer, (2) contains a region of the center and/or its neighborhood of continuous epithelial tissue in the cell aggregate, and (3) is from 600 μm to 2500 μm in major axis, from 200 μm to 1500 μm in minor axis, and from 100 μm to 1000 μm in thickness.

[17]

The composition for transplantation according to any of [11] to [16], wherein the transplant neural retina sheet (1) has been isolated from a cell aggregate containing at least first epithelial tissue and second epithelial tissue, wherein the first epithelial tissue contains a human neural retina, and the second epithelial tissue has the continuity of the slope of a tangent line to a surface different from the continuity of the slope of a tangent line to the surface of the first epithelial tissue, and contains a non-neural retina-related cell, (2) contains a region on the first epithelial tissue most distant from the second epithelial tissue, and (3) is from 600 μm to 2500 μm in major axis, from 200 μm to 1500 μm in minor axis, and from 100 μm to 1000 μm in thickness, wherein the second epithelial tissue is a tissue selected from the group consisting of eyeball-related tissue, brain and spinal cord tissue and other tissues different from the neural retina of the first epithelial tissue.

[18]

The composition for transplantation according to any of [11] to [17], wherein the ratio of a Rx-positive cell to the total number of cells in the transplant neural retina sheet is 30% or more and 80% or less, 40% or more and 70% or less, 45% or more and 60% or less, or 50% or more and 60% or less.

[19]

The composition for transplantation according to any of [11] to [18], wherein the ratio of a Chx10-positive cell to the total number of cells in the transplant neural retina sheet is 10% or more and 80% or less, 20% or more and 70% or less, 30% or more and 60% or less, or 40% or more and 50% or less.

[20]

The composition for transplantation according to any of [11] to [19], wherein the ratio of a Pax6-positive cell to the total number of cells in the transplant neural retina sheet is 10% or more and 80% or less, 20% or more and 70% or less, 30% or more and 60% or less, or 40% or more and 50% or less.

[21]

The composition for transplantation according to any of [11] to [20], wherein the ratio of a Crx-positive cell to the total number of cells in the transplant neural retina sheet is 10% or more and 70% or less, 10% or more and 60% or less, 20% or more and 60% or less, 30% or more and 60% or less, 40% or more and 60% or less, or 50% or more and 60% or less.

[22]

A method for treating a disease caused by the damage of a neural retina-related cell or a neural retina or the injury of a neural retina, comprising subretinally transplanting the composition for transplantation according to any of [11] to [21] to a subject in need of transplantation.

Advantageous Effects of Invention

According to the present invention, it has become possible to provide a vehicle and a composition for transplantation comprising retinal tissue and the vehicle, which are suitable for the subretinal transplantation of retinal tissue. The composition for transplantation is useful in transplantation therapy with retinal tissue for the treatment of retinal degenerative diseases such as retinitis pigmentosa.

BRIEF DESCRIPTION OF DRAWINGS

FIG. 7 FIG. 5 is a conceptual view of preparing a Cap and a Ring from cell aggregates having various shapes. Portions indicated in black color and gray color mean non-target tissue.

FIG. 8 FIG. 6 shows images of typical grafts and a schematic view of a graft as well as the heights, major axes and minor axes of grafts in Reference Example 3.

DESCRIPTION OF EMBODIMENTS

1. Vehicle for Transplantation

Figure 1:
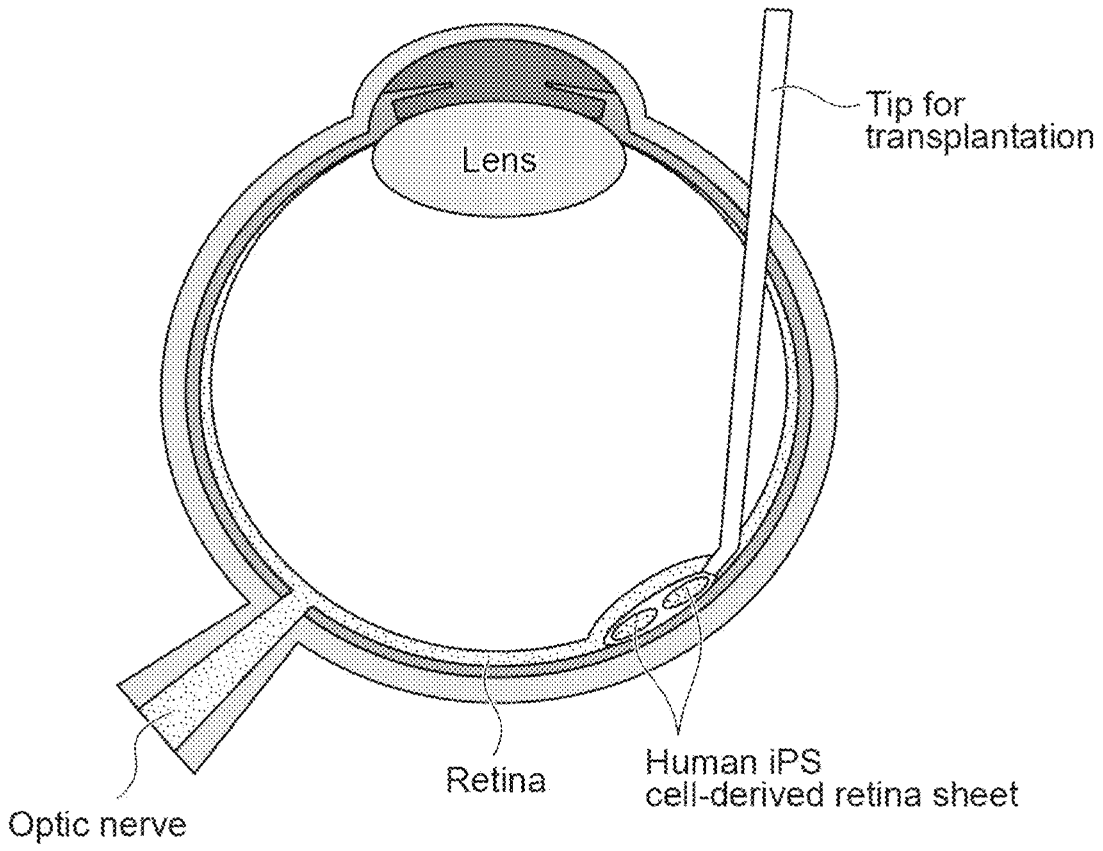
FIG. 1 is a diagram showing a method for subretinally transplanting a retina sheet using a tip for transplantation in Example 1.

The present invention provides a vehicle for transplantation that is used in subretinally transplanting a graft of retinal tissue to a mammal.

The vehicle for transplantation of the present invention is not limited as long as it is a vehicle having a viscosity of 5 to 500 mPa·s, preferably 10 to 100 mPa·s, at a shear rate of 2 (1/s) at 25° C. and comprising hyaluronic acid and a pharmaceutically acceptable aqueous liquid.

In the vehicle for transplantation of the present invention, preferably, viscosity at a shear rate of 1000 (1/s) at 25° C. is 100 mPa·s or less, preferably 30 mPa·s or less, and the amount of change in viscosity from shear rates of 1 to 10 (1/s) (i.e., the viscosity difference between viscosity at a shear rate of 1 (1/s) and viscosity at a shear rate of 10 (1/s)) is 100 mPa·s or less, preferably 30 mPa·s or less. Alternatively, it is preferable the rate of change in viscosity from shear rates of 1 to 10 (1/s) (i.e., percentage when the viscosity difference between viscosity at a shear rate of 1 (1/s) and viscosity at a shear rate of 10 (1/s) is divided by viscosity at a shear rate of 1 (1/s)) should be about 10% or less.

The vehicle for transplantation of the present invention preferably further comprises chondroitin sulfate. The hyaluronic acid and the chondroitin sulfate function as thickening components of the vehicle for transplantation.

In the specification, the hyaluronic acid is linear macromolecular polysaccharide with a molecular weight of several tens of thousands to several millions having a structure where D-glucuronic acid and D-N-acetylglucosamine are alternately linked via β-1,4 and β-1,3 glycosidic bonds. The hyaluronic acid is a substance that has high ability to retain water and viscosity and is widely used in medicines, cosmetics, etc. In the specification, the “hyaluronic acid” is meant to conceptually include both a free form of hyaluronic acid and a salt thereof. Examples of the salt of hyaluronic acid include alkali metal salts and alkaline earth metal salts of hyaluronic acid. Specifically, commercially available sodium hyaluronate, potassium hyaluronate, or the like can be used.

In the specification, the hyaluronic acid is not particularly limited as long as the viscosity of the vehicle for transplantation at a shear rate of 2 (1/s) at 25° C. can be kept at 5 to 500 mPa·s, preferably 10 to 100 mPa·s. The vehicle for transplantation can be blended with hyaluronic acid having an average molecular weight of about 500,000 to 3,900,000 at a concentration of 0.15 w/v % to 1.50 w/v %, preferably 0.15 w/v % to 0.75 w/v %, more preferably 0.30 w/v % to 0.50 w/v %.

The chondroitin sulfate is mucopolysaccharide having a structure where sulfuric acid is bonded to a sugar chain having repeats of two saccharides D-glucuronic acid (GlcA) and N-acetyl-D-galactosamine (GalNAc). In the specification, the “chondroitin sulfate” is meant to conceptually include both a free form of chondroitin sulfate and a salt thereof. Examples of the salt of chondroitin sulfate include alkali metal salts and alkaline earth metal salts of chondroitin sulfate. Specifically, commercially available chondroitin sulfate sodium salt, chondroitin sulfate potassium salt, or the like can be used.

In the specification, the chondroitin sulfate is not particularly limited as long as the viscosity of the vehicle for transplantation at a shear rate of 2 (1/s) at 25° C. can be kept at 5 to 500 mPa·s, preferably 10 to 100 mPa·s, together with hyaluronic acid. The vehicle for transplantation can be blended with chondroitin sulfate having an average molecular weight of about 20,000 to 24,000 at a concentration of 0.3 w/v % to 1.0 w/v %, preferably 0.4 w/v % to 0.7 w/v %.

The "pharmaceutically acceptable aqueous liquid" in the vehicle of the present invention is not particularly limited as long as it is an aqueous solution that can be administered to a living body and has physical properties suitable for transplantation. For example, an aqueous solution containing a buffer, a transfusion, saline, injectable water, or a perfusate may be used. A buffer is preferable.

In this context, examples of the physical properties suitable for transplantation include pH and osmotic pressure. The pH of the vehicle for transplantation is not particularly limited as long as it is in a neutral range. The vehicle for transplantation of the present invention may be adjusted to pH 6.5 to 8.0, preferably pH on the order of 7.0 to 7.5.

Examples of the osmotic pressure of the vehicle for transplantation include hypotonic, isotonic, and hypertonic pressures. It is preferable to be close to isotonic pressure. The osmotic pressure ratio may be adjusted to 0.7 to 1.3, preferably 0.9 to 1.1.

Examples of the "pharmaceutically acceptable aqueous liquid" specifically include aqueous solutions containing a balanced salt (i.e., balanced salt solutions). In the aqueous solution containing a balanced salt, a buffer, a tonicity agent, a pH adjuster, an antioxidant, a chelating agent, or the like can be appropriately selected and contained within a range that does not influence the survival rate of retinal tissue to be transplanted.

Examples of the buffer include phosphate buffers, borate buffers, citrate buffers, tartrate buffers, acetate buffers, amino acids, and epsilon-aminocaproic acid.

Examples of the tonicity agent include sugars such as sorbitol, glucose, mannitol, polyhydric alcohols such as glycerin and propylene glycol, salts such as sodium chloride, and boric acid.

Examples of the chelating agent include sodium edetate and citric acid.

Examples of the pH adjuster include sodium hydroxide, potassium hydroxide, sodium carbonate, sodium bicarbonate, boric acid and salts thereof (borax), hydrochloric acid, citric acid and salts thereof (sodium citrate, sodium dihydrogen citrate, etc.), phosphoric acid and salts thereof (disodium hydrogen phosphate, potassium dihydrogen phosphate, etc.), acetic acid and salts thereof (sodium acetate, ammonium acetate, etc.), and tartaric acid and salts thereof (sodium tartrate, etc.).

Examples of the antioxidant include ascorbic acid, glutathione, sodium bisulfite, dry sodium sulfite, sodium pyrosulfite, and tocopherol.

The vehicle for transplantation of the present invention can be preferably subjected to sterilization treatment such as filter sterilization using a membrane filter or the like.

Examples of the "pharmaceutically acceptable aqueous liquid" specifically include aqueous solutions containing one or more components selected from sugars such as glucose, inorganic salts such as calcium chloride, sodium chloride, and magnesium sulfate, inorganic materials such as sodium bicarbonate, sodium acetate, sodium citrate, sodium dihydrogen phosphate, sodium hydrogen phosphate, anhydrous sodium monohydrogen phosphate, and hydrochloric acid, and chelating agents such as edetate (e.g., sodium edetate).

As hyaluronic acid or a salt thereof, a commercially available aqueous solution of hyaluronic acid or a salt thereof can be used. Specifically, examples thereof include Opegan® 0.6 ophthalmic viscoelastic preparation containing 0.6% sodium hyaluronate, sodium chloride, sodium dihydrogen phosphate and sodium hydrogen phosphate as components, Opegan® 1.1 ophthalmic viscoelastic preparation containing 1.1% sodium hyaluronate, sodium chloride, sodium dihydrogen phosphate and sodium hydrogen phosphate as components, and Hyalein Mini® ophthalmic solution 0.3% containing 0.3% sodium hyaluronate, epsilon-aminocaproic acid, sodium edetate hydrate, potassium chloride, sodium chloride and a pH adjuster as components.

For preparing the pharmaceutically acceptable aqueous liquid, a liquid commercially available as an intraocular perfusate or lavage can be used. As the intraocular perfusate or lavage, specifically, an aqueous solution commercially available as Opeguard® containing 1.5 mg of glucose, 0.18 mg of calcium chloride hydrate, 0.3 mg of magnesium sulfate hydrate, 2.1 mg of sodium bicarbonate, and sodium citrate hydrate, sodium acetate hydrate and hydrochloric acid as additives in 1 mL, or an oxiglutatione ocular perfusate or the like can be used. For preparing the pharmaceutically acceptable aqueous liquid, Hank's balanced salt solution (HBSS), Eagle balanced salt solution (EBSS), phosphate-buffered saline (PBS), Dulbecco's phosphate-buffered saline (DPBS), or the like can also be used.

An embodiment of the vehicle for transplantation of the present invention includes a vehicle for transplantation containing only hyaluronic acid as a thickening component. Specifically, it can be prepared, for example, by blending Opegan® 0.6 ophthalmic viscoelastic preparation with an aqueous liquid such as Opeguard at 1:1 to 1:3. In another embodiment, it can be prepared, for example, by blending Hyalein Mini® ophthalmic solution 0.3% with an aqueous liquid such as Opeguard at 3:1 to 1:1.

An embodiment of the vehicle for transplantation of the present invention includes a vehicle for transplantation containing hyaluronic acid and chondroitin sulfate as thickening components. In this context, the concentrations of the hyaluronic acid and the chondroitin sulfate are not particularly limited as long as the viscosity of the vehicle for transplantation at a shear rate of 2 (1/s) at 25° C. can be kept at 5 to 500 mPa·s, preferably 10 to 100 mPa·s. An embodiment of the vehicle for transplantation of the present invention includes a composition for transplantation containing 0.15 w/v % to 1.50 w/v % of hyaluronic acid having an average molecular weight of 500,000 to 3,900,000, and 0.3 w/v % to 1.0 w/v % of chondroitin sulfate having a molecular weight of 20,000 to 24,000 or a salt thereof.

In an embodiment of the vehicle for transplantation of the present invention, Viscoat® 0.5 ophthalmic viscoelastic preparation containing sodium hyaluronate, chondroitin sulfate sodium salt, sodium dihydrogen phosphate, sodium hydrogen phosphate and a tonicity agent as components can be used. Specifically, it can be prepared, for example, by blending Viscoat® 0.5 ophthalmic viscoelastic preparation with an aqueous liquid such as Opeguard at 1:3 to 1:7.

The "pharmaceutically acceptable aqueous liquid" preferably comprises neither an antimicrobial agent nor an antiseptic.

2. Transplant Retinal Tissue

Definition

In the specification, the "tissue" refers to a structure of a cell population having a structure where one or more types of cells differing in morphology or properties are three-dimensionally arranged in a predetermined pattern.

In the specification, the "retinal tissue" means a tissue in which one or more types of retina cells, such as photoreceptor cells, horizontal cells, bipolar cells, amacrine cells, retinal ganglion cells, Muller glial cells, retinal pigment epithelial cells, their progenitor cells, or retinal progenitor cells, constituting each retinal layer in a retina in vivo are three-dimensionally arranged, preferably three-dimensionally arranged in a layer pattern, and may be a cell aggregate or a cell sheet mentioned later.

The photoreceptor progenitor cells, the horizontal progenitor cells, the bipolar progenitor cells, the amacrine progenitor cells, the retinal ganglion progenitor cells, the Muller glial progenitor cells, and the retinal pigment epithelial progenitor cells refer to progenitor cells destined for differentiation into photoreceptor cells, horizontal cells, bipolar cells, amacrine cells, retinal ganglion cells, Muller glial cells, and retinal pigment epithelial cells, respectively.

The "retinal progenitor cells" are progenitor cells capable of differentiating into any one of the immature retinal cells such as photoreceptor progenitor cells, horizontal progenitor cells, bipolar progenitor cells, amacrine progenitor cells, retinal ganglion progenitor cells, Muller glial cells, and retinal pigment epithelial progenitor cells, and refer to progenitor cells also capable of eventually differentiating into any one of the matured retinal cells such as photoreceptor cells, rod photoreceptor cells, cone photoreceptor cells, horizontal cells, bipolar cells, amacrine cells, retinal ganglion cells, and retinal pigment epithelial cells.

In the specification, the "retinal layer" means a cell population in a layer pattern in which one or more cells constituting the retina form a single layer or a plurality of layers in a predetermined pattern, and examples thereof specifically include retinal pigment epithelial layer containing retinal pigment epithelial cells, and neural retinal layer containing neural retina cells. The neural retina cells are also referred to as retinal layer-specific neuronal cells.

Examples of the neural retinal layer include outer limiting membrane, photoreceptor layer (outer nuclear layer), outer plexiform layer, inner nuclear layer, inner plexiform layer, ganglion cell layer, nerve fiber layer and inner limiting membrane.

In the specification, the "neural retina" means retinal tissue containing a neural retinal layer.

Examples of the neural retina cells include photoreceptor cells (including photoreceptor progenitor cells and matured photoreceptor cells), bipolar cells, retinal ganglion cells, amacrine cells, horizontal cells, Muller glial cells, and their progenitor cells.

In the specification, the "neural retinal progenitor cells" mean progenitor cells of neural retina cells.

The "photoreceptor cells" are present in the photoreceptor layer of a retina in vivo and plays a role in absorbing light stimuli and converting them to electrical signals. The photoreceptor cells have two types, cone cells which function in the light and rod cells which function in the dark. Examples of the cone photoreceptor cells can include S cone photoreceptor cells which express S-opsin and receive blue light, L cone photoreceptor cells which express L-opsin and receive red light, and M cone photoreceptor cells which express M-opsin and receive green light. The photoreceptor cells are matured after differentiation from photoreceptor progenitor cells. Whether or not cells are photoreceptor cells or photoreceptor progenitor cells can be readily confirmed by those skilled in the art, for example, through the expression of cell markers (Crx and Blimp 1 expressed in photoreceptor progenitor cells, recoverin expressed in photoreceptor cells, rhodopsin, S-opsin and M/L-opsin expressed in mature photoreceptor cells, etc.) mentioned later or the formation of an outer segment structure. In an embodiment, the photoreceptor progenitor cells are Crx-positive cells, and the photoreceptor cells are rhodopsin-, S-opsin- and M/L-opsin-positive cells. In an embodiment, the rod photoreceptor cells are NRL- and rhodopsin-positive cells. In an embodiment, the S cone photoreceptor cells are S-opsin-positive cells, the L cone photoreceptor cells are L-opsin-positive cells, and the M cone photoreceptor cells are M-opsin-positive cells. Specifically, in the specification, the photoreceptor cells conceptually include photoreceptor progenitor cells and matured photoreceptor cells.

In the neural retina cells, neither retinal pigment epithelial cells nor ciliary body cells are included.

In the specification, an embodiment of the retinal tissue includes a neural retina, preferably a neural retina containing a retinal layer-specific neuronal cell layer, more preferably a neural retina containing a photoreceptor layer.

The neural retina contains preferably 10% or more, more preferably 20% or more, of a photoreceptor cell or a photoreceptor progenitor cell.

The neural retina contains preferably 10% or more, more preferably 20% or more, of a neural retinal progenitor cell. Also, the neural retina contains preferably 10% or more of a photoreceptor progenitor cell. In an embodiment, the neural retina contains 3% or more of a matured photoreceptor cell.

In the specification, an embodiment of the retinal tissue includes retinal tissue containing both a neural retina and a cell layer containing an RPE cell. Examples of the retinal tissue include neural retinas covered with RPE cells described in WO2019/050015.

In the specification, an embodiment of the retinal tissue includes retinal tissue (complex) in which a neural retina and a RPE cell have adhered via polymer hydrogel. Specifically, examples thereof include a complex comprising a neural retina, a retinal pigment epithelial cell, and hydrogel, wherein the neural retina and the retinal pigment epithelial cell are each derived from a human pluripotent stem cell, a neural retinal layer containing at least a photoreceptor layer is formed in the neural retina, and the photoreceptor layer contains one or more cells selected from the group consisting of a photoreceptor cell, a photoreceptor progenitor cell and a retinal progenitor cells. In this context, the hydrogel is not particularly limited as long as it is a polymer and a substance having physical properties useful in the adhesion between a tissue and a tissue (examples thereof include glues, adhesives, matter having gelling physical properties, gelatin, and oil and fat).

Each cell constituting the retinal tissue mentioned above can be detected or identified by using a retina cell marker that is expressed (positive) or not expressed (negative) therein.

Examples of the retina cell marker include Rx (also referred to as Rax) and PAX6 expressed in retinal progenitor cells, Rx, PAX6 and Chx10 (also referred to as Vsx2)

expressed in neural retinal progenitor cells, or Crx and Blimp 1 expressed in photoreceptor progenitor cells. Examples of the negative marker for retinal progenitor cells or retina cells include Nkx2.1 and SOX1.

Examples of the marker for retinal layer-specific neuronal cells include recoverin expressed in photoreceptor cells (particularly, matured photoreceptor cells), Crx and Blimp1 expressed in photoreceptor cells (particularly, photoreceptor progenitor cells), rhodopsin expressed in rod cells, Nrl expressed in rod photoreceptor cells and rod photoreceptor progenitor cells, S-opsin and LM-opsin expressed in cone photoreceptor cells, RXR-γ expressed in cone cells, cone photoreceptor progenitor cells and ganglion cells, TRβ2, OTX2 and OC2 expressed in cone photoreceptor cells that appear at the early phase of differentiation among cone photoreceptor cells, or progenitor cells thereof, Chx10, PKCα, Goα, VSX1 and L7 expressed in bipolar cells, TuJ1 and Brn3 expressed in retinal ganglion cells, calretinin and HPC-1 expressed in amacrine cells, calbindin expressed in horizontal cells, and Pax6 commonly expressed in horizontal cells, amacrine cells and ganglion cells.

A layer that has a low appearance ratio of photoreceptor cells or photoreceptor progenitor cells, is rich in neural retinal progenitor cells, and is at a stage of differentiation before forming a photoreceptor layer is referred to as "neuroblastic layer" and includes inner neuroblastic layer and outer neuroblastic layer. Those skilled in the art can make a judgment from the shade of color (the outer neuroblastic layer is light, and the inner neuroblastic layer is dark) by a known method, for example, under a bright field microscope.

The presence or absence of expression of the retina cell marker, or the ratio of retina cell marker-positive cells in a cell population or a tissue can be readily confirmed by those skilled in the art. Examples thereof include an approach using an antibody, an approach using nucleic acid primers, and an approach using sequencing reaction. As the approach using an antibody, the expression of a protein of the retina cell marker can be confirmed, for example, by dividing the number of predetermined retina cell marker-positive cells by the total number of cells in accordance with an approach such as flow cytometry or immunostaining using a commercially available antibody. As the approach using nucleic acid primers, the expression of RNA of the retina cell marker can be confirmed by, for example, PCR, semiquantitative PCR, or quantitative PCR (e.g., real-time PCR). As the approach using sequencing reaction, the expression of RNA of the retina cell marker can be confirmed using, for example, a nucleic acid sequencer (e.g., next-generation sequencer).

The "positive cells" mean cells expressing a predetermined marker on the cell surfaces or within the cells. For example, the "Chx10-positive cells" mean cells expressing Chx10 protein.

The "negative cells" mean cells that do not express a predetermined marker on the cell surfaces or within the cells. For example, the "SOX1-negative cells" mean cells that do not express SOX1 protein. In this context, "not express" encompasses the case where the expression level thereof is below a detection limit, or the case where the expression is 1/10 or less, preferably 1/50 or less, as compared with positive cells.

In another embodiment, for example, the "SOX1-negative cells" mean cells that do not express mRNA of SOX1. In this context, "not express" encompasses the case where the expression level thereof is below a detection limit, or the case where the expression is 1/10 or less, preferably 1/50 or less, as compared with positive cells. Particularly, in the case of measuring a mRNA level by qPCR, delta between a target gene (e.g., SOX1) and an internal standard (GAPDH or ACTB) can be evaluated as a ΔCt value. The term "not express" encompasses the case where the ΔCt value is 4 or more, more preferably 6 or more, further preferably 8 or more.

The "retinal pigment epithelial cells" mean epithelial cells present outside the neural retina in a retina in vivo. Whether or not cells are retinal pigment epithelial cells can be readily confirmed by those skilled in the art, for example, through the expression of cell markers (RPE65, MITF, CRALBP, MERTK, BEST1, TTR, etc.), the presence of melanin granules (brown-black), intercellular tight junctions, or polygonal/flagstone-like characteristic cell morphology. Whether or not cells have a function of retinal pigment epithelial cells can be readily confirmed from the ability to secrete cytokines such as VEGF and PEDF. In an embodiment, the retinal pigment epithelial cells are RPE65-positive cells, MITF-positive cells, or RPE65-positive and MITF-positive cells.

The "ciliary body" includes "ciliary body" and "ciliary marginal zone" in the process of development and of an adult. Examples of a marker of the "ciliary body" include Zic1, MAL, HNF1beta, FoxQ1, CLDN2, CLDN1, GPR177, AQP1 and AQP4. Examples of the "ciliary marginal zone (CMZ)" can include a tissue that is present in a boundary region between the neural retina and the retinal pigment epithelium in a retina in vivo, and is a region containing tissue stem cells of the retina (retinal stem cells). The ciliary marginal zone is also called ciliary margin or retinal margin, and the ciliary marginal zone, the ciliary margin and the retinal margin are equivalent tissues. The ciliary marginal zone is known to play an important role in the supply of retinal progenitor cells or differentiated cells to retinal tissue, the maintenance of a retinal tissue structure, etc. Examples of a marker gene of the ciliary marginal zone can include Rdh10 gene (positive), Otx1 gene (positive) and Zic1 (positive). The "ciliary marginal zone-like structure" is a structure similar to the ciliary marginal zone.

(Structure of Retinal Tissue)

In the specification, the retinal tissue may be a form having a three-dimensional structure, i.e., a cell aggregate (also referred to as a cell cluster, stereoscopic tissue, or organoid), or may be a cell sheet in which a structure in a layer pattern is two-dimensionally expanded, i.e., a retinal cell sheet. In the cell aggregate or the cell cluster, a sphere is also included. In this context, the sphere means a cell aggregate having a stereoscopic shape close to a spherical shape. The stereoscopic shape close to a spherical shape is a shape having a three-dimensional structure, and examples thereof include a spherical shape that exhibits a circle or an ellipse when projected onto a two-dimensional surface, and a shape formed by fusing a plurality of spherical shapes (e.g., which exhibits a shape formed by 2 to 4 circles or ellipses overlapping when two-dimensionally projected). In an embodiment, the core part of the aggregate has a vesicular lamellar structure and is characterized in that the central part is observed to be dark and the outer edge portion is observed to be bright under a bright field microscope.

In an embodiment, some or all cells contained in the cell aggregate or the cell sheet mutually adhere. Specifically, in a portion or the whole of the aggregate, cells may mutually form cell-cell junction or cell adhesion, for example, adherence junction.

The shape and size of the cell aggregate or the cell sheet are not particularly limited and can be appropriately set according to an area in need of repair of retinal tissue in the case of being administered as a graft to a mammal, preferably a monkey or a human. Specifically, the size of the retinal tissue to be transplanted to a recipient is a size suitable for the recipient and is a size that permits movement inside a cell suction portion (needle tube for transplantation) in a device that is used in transplantation.

In the specification, an embodiment of the retinal tissue contained in a composition for transplantation specifically includes retinal tissue that is from 200 to 1500 μm in minor axis, from 600 to 2500 μm in major axis, and from 100 to 1000 μm in thickness. The retinal tissue of size suitable for transplantation, i.e., a graft, can be prepared by appropriately dissecting the size suitable for transplantation from the cell aggregate or the cell sheet.

Specifically, a cell sheet of size suitable for transplantation can be dissected from the cell aggregate and used as a graft.

In the specification, the retinal tissue may have an epithelial structure. The epithelial structure is formed by covering the surface of a tissue with cells without any space, and polarized to have an "apical surface" and a "basal membrane (basal surface)". In this context, the "basal membrane" is a layer that is rich in laminin and IV-type collagen and is 50 to 100 nm. The "apical surface" refers to the surface (upper surface layer) formed on the opposite side to the "basal membrane". In an embodiment, in the retinal tissue developed to the extent that photoreceptor cells or photoreceptor progenitor cells are observed, the "apical surface" refers to a surface in contact with photoreceptor layer (outer nuclear layer) in which outer limiting membrane is formed and photoreceptor cells and photoreceptor progenitor cells are present. Such an apical surface can be identified by, for example, immunostaining (known to those skilled in the art) using an antibody against an apical surface marker (e.g., atypical PKC (hereinafter, abbreviated to "aPKC"), E-cadherin, N-cadherin).

Cells constituting the epithelial structure, i.e., epithelial cells, can mutually and firmly join via adherence junction and/or tight junction to form a layer of the cells. A tissue formed from a single layer or dozen layers overlapping of this layer of the cells is the epithelial structure.

In the specification, an epithelial structure containing neural tissue is referred to as neural epithelium. Particularly, an epithelial structure containing a neural retina is referred to as neural retinal epithelium.

In the specification, in an embodiment, the neural retina may assume a polarized layer structure. For example, the neural retina, when having a shape of a cell sheet, may have apical/basal polarity. When the neural retina is a sphere-like cell aggregate, the cell aggregate may have an epithelial structure, and the epithelial structure may have apical/basal polarity in the surface and the inside of the cell aggregate.

In the specification, one embodiment of the retinal tissue contained in a composition for transplantation includes retinal tissue containing a front surface (apical surface) and a back surface (basal surface), wherein the front surface constitutes an apical surface containing a neural retinal layer which is epithelial tissue by forming the adherence junction between cells, and the back surface constitutes a basal surface adjacent to the inner layer of the neural retina. Such retinal tissue can be referred to as neural retinal epithelium. For such retinal tissue, it is preferable to be a neural retina sheet which is a sheet-shaped retinal tissue. The front surface has a smooth shape with less change in curvature, and the back surface has an irregular shape with large change in curvature. In an embodiment, the change in the curvature of the front surface of the retinal tissue may be, for example, close to change in curvature of an ellipse (e.g., an ellipse having a major axis of 1 to 10 with respect to a minor axis of 1) (also referred to as continuous change in curvature). In an embodiment, the change in the curvature of the back surface of the retinal tissue may be, for example, close to sharp change in curvature that goes back and force between positive values and negative values, as in "teeth of a saw" (also referred to as sharp change in curvature).

In the specification, the retinal tissue is preferably retinal tissue having a continuous epithelial structure. The "continuous epithelial structure" is a structure where the epithelial tissue is continuously formed, and is also referred to as "continuous epithelium". The epithelium tissue continuously formed is a state in which 10 cells to $10^7$ cells, for example, in the tangent direction of the epithelial tissue, preferably 30 cells to $10^7$ cells, further preferably $10^2$ cells to $10^7$ cells, in the tangent direction, are aligned. The continuous epithelial structure does not have a structure where an apical surface is divided, as found in a rosette-like structure. In an embodiment, the number of cells per area of the cross section of retinal tissue having the continuous epithelial structure is 10 cells to 900 cells, preferably 30 cells to 300 cells, more preferably 50 cells to 250 cells, still more preferably 75 cells to 160 cells, per 100 $\mu m^2$, for example, in the case of evaluating the number of nuclei of cells in a frozen section having a thickness on the order of 10 μm.

For example, in the continuous epithelium formed in retinal tissue, the retinal tissue has an apical surface intrinsic to the epithelial tissue. The apical surface is formed almost in parallel to, for example, at least photoreceptor layer (outer nuclear layer) among the layers forming a neural retinal layer and continuously on the surface of the retinal tissue. For example, in the case of a cell aggregate containing retinal tissue prepared from pluripotent stem cells, the apical surface is formed on the surface of the aggregate, and continuous neural epithelium is formed in which 10 cells or more, preferably 30 cells or more, more preferably 100 cells or more, further preferably 400 cells or more of photoreceptor cells or photoreceptor progenitor cells are regularly and continuously aligned in the tangent direction of the surface. A neural retina containing such continuous neural epithelium is neural retinal epithelium containing continuous epithelium.

Whether retinal tissue contains continuous epithelium can be confirmed from the continuity (i.e., undivided form) of the apical surface of retinal tissue. The continuity of the apical surface can be determined, for example, by immunostaining a marker of the apical surface (e.g., aPKC, E-cadherin, N-cadherin) and a marker of photoreceptor cells or photoreceptor progenitor cells positioned on the apical surface side (e.g., Crx or recoverin), and analyzing obtained images, etc. for the positional relationship of the apical surface to a photoreceptor layer and each retinal layer. A retinal layer other than the apical surface or the photoreceptor layer (outer nuclear layer) can be identified by, for example, DAPI staining which stains the nuclei of cells, PI staining, Hoechst staining, or immunostaining with a marker protein (Rx, Chx10, Ki67, Crx, etc.) or the like localized in the nuclei of cells.

Specifically, the continuity of the apical surface can be identified from the continuous presence of cells co-expressing a marker of cells present on the apical surface side, i.e., a photoreceptor cell marker or a photoreceptor progenitor cell marker, and a marker capable of staining the nuclei of cells.

In the specification, the retinal tissue preferably includes a neural retina containing a photoreceptor cell or a photoreceptor progenitor cell and in other words, a neural retina containing a photoreceptor layer.

In the specification, the retinal tissue preferably includes a neural retina in which a neural retinal layer or a photoreceptor layer has a continuous epithelial structure, i.e., has a continuous neuroepithelial structure.

In the specification, the retinal tissue may contain an "inner layer" containing a ganglion cell or an amacrine cell inside a photoreceptor layer. The inner layer may be in contact with the basal surface.

These neural retinas can be obtained by producing a cell aggregate containing a neural retina by a production method mentioned later.

(Cell Aggregate Containing Neural Retina)

In an embodiment, the cell aggregate containing a neural retina is a sphere-like cell aggregate. In an embodiment, in the cell aggregate containing a neural retina, a plurality of neural retinas may be present with an overlap (e.g., see conceptual views (1) and (2) in FIG. 7). In an embodiment, the cell aggregate containing a neural retina contains first epithelial tissue (target epithelial tissue) containing the transplant neural retina, and second epithelial tissue (non-target epithelial tissue) having the continuity of the slope of a tangent line to a surface different from the continuity of the slope of a tangent line to the surface of the first epithelial tissue, and containing a non-neural retina-related cell. In this context, the first epithelial tissue refers to epithelial tissue that does not substantially contain a non-neural retina-related cell (non-target cell) and allows the transplant neural retina to be dissected. On the other hand, the second epithelial tissue is epithelial tissue that may contain a neural retina, but is ineligible for dissecting the transplant neural retina because of containing non-target cells. In another embodiment, the cell aggregate containing a neural retina contains only the first epithelial tissue (target epithelial tissue) containing the transplant neural retina and does not contain non-target epithelial tissue.

(Transplant Retinal Tissue)

The transplant retinal tissue is the retinal tissue described in the specification and is human retinal tissue suitable for transplantation in humans. It is preferably a neural retina and more preferably consists of only the neural retina.

The transplant retinal tissue can be prepared by dissecting a site suitable for transplantation from the cell aggregate mentioned above. In an embodiment, the transplant retinal tissue can be prepared by dissecting a neural retina from a cell aggregate containing the neural retina. When the retinal tissue, preferably the neural retina, contains continuous epithelium, a sheet-shaped retinal tissue (hereinafter, also referred to as a retina sheet), preferably a sheet-shaped neural retina (hereinafter, also referred to as a neural retina sheet), containing the continuous epithelium can be dissected.

The transplant neural retina contains at least a photoreceptor layer. The photoreceptor layer is formed at least in the outmost of the cell aggregate. Also, photoreceptor cells or photoreceptor progenitor cells may be present in the inside. Alternatively, the photoreceptor layer may be formed in the inside. Photoreceptor cells, etc. are present continuously, i.e., by mutual adhesion, in the tangent direction of the surface of the cell aggregate. The photoreceptor cells, etc. are present continuously in the tangent direction of the surface of the cell aggregate, thereby forming a photoreceptor layer containing the photoreceptor cells, etc. The tangent direction refers to a direction tangent to the surface of the cell aggregate, i.e., a direction along which the photoreceptor cells, etc. in the photoreceptor layer are arranged, and is the direction in parallel to the neural retina or the lateral direction. The slope of a tangent line to the surface of epithelial tissue refers to a direction along which cells are arranged when individual cells in the epithelial tissue are arranged in a predetermined direction, and refers to the direction in parallel to the epithelial tissue (or epithelial sheet) or the lateral direction.

The cell aggregate that is used for preparing the transplant neural retina may contain non-target tissue other than a neural retina. Examples of the non-target tissue include epithelial tissue other than a neural retina, i.e., second epithelial tissue containing non-target epithelial tissue. Examples of the second epithelial tissue include eyeball-related tissue and brain and spinal cord tissue. The eyeball-related tissue means a non-neural retinal tissue surrounding eyeball tissue, and examples thereof include retinal pigment epithelial cells, ciliary body (e.g., ciliary marginal zone), lens, and cornea. The brain and spinal cord tissue means neural tissue of the brain and the spinal cord, and examples thereof include the forebrain, the telencephalon, the cerebrum, the diencephalon, the hypothalamus, the midbrain, the hindbrain, the cerebellum, and the spinal cord. In an embodiment, the brain and spinal cord tissue may contain pituitary gland.

Figure 6:
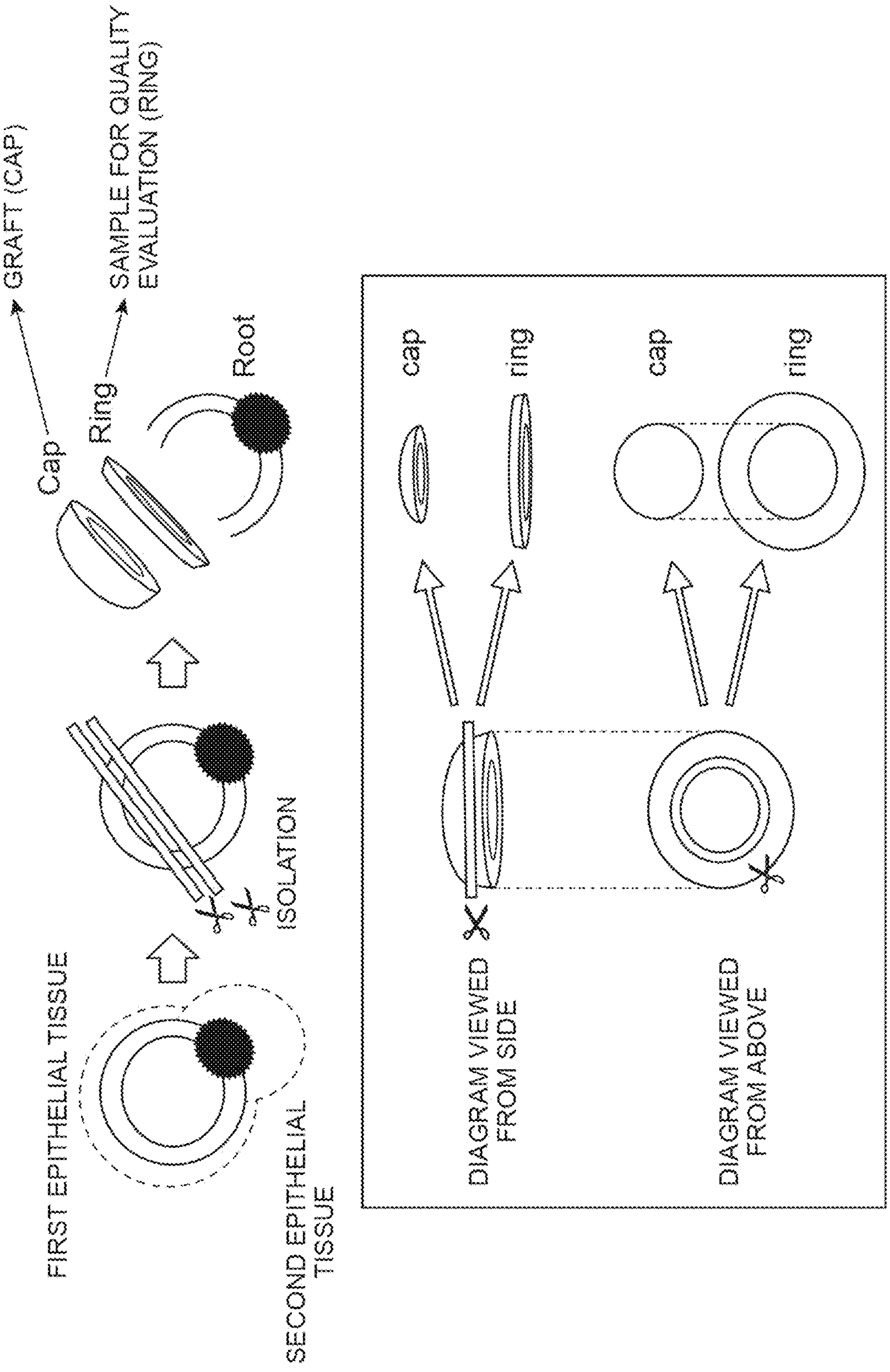
FIG. 6 is a conceptual view of preparing a Cap and a Ring from a typical cell aggregate.
Figure 7:
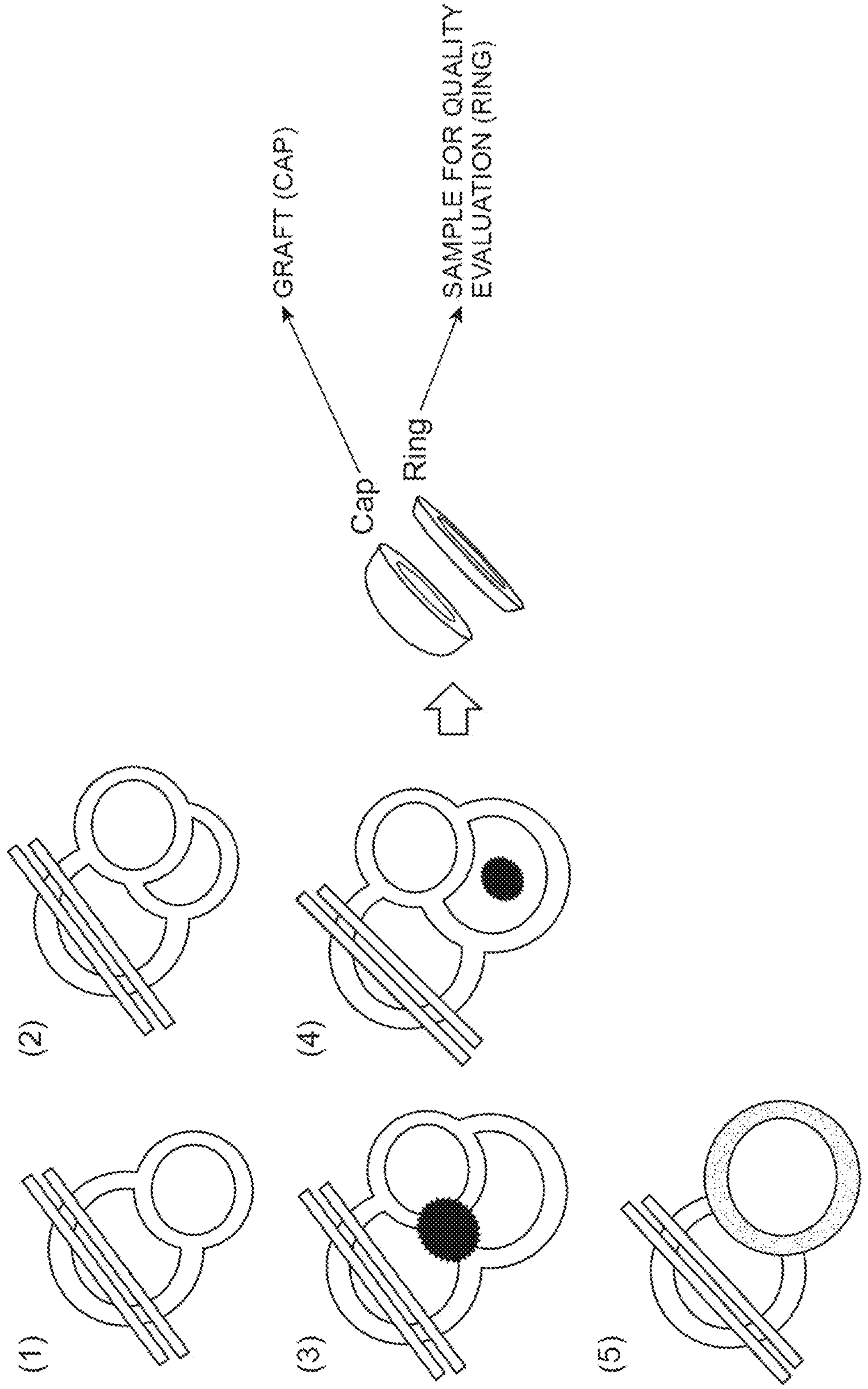

One example of the cell aggregate containing the first epithelial tissue and the second epithelial tissue includes cell aggregates shown in a conceptual view of FIG. 6 and conceptual views (3) and (5) of FIG. 7. The conceptual view of FIG. 6 shows one example of a cell aggregate in which eyeball-related tissue (retinal pigment epithelial cells, ciliary body) (black portion of FIG. 6) is present as the second epithelial tissue in a part of a neural retina which is the first epithelial tissue. The conceptual view (3) of FIG. 7 shows one example of a cell aggregate in which eyeball-related tissue (retinal pigment epithelial cells, ciliary body) (black portion of the conceptual view (3) of FIG. 7) is further present as the second epithelial tissue when a plurality of neural retinas are present with an overlap (e.g., conceptual views (1) and (2) of FIG. 7). The conceptual view (5) of FIG. 7 shows one example of a cell aggregate in which brain and spinal cord tissue (cerebrum, etc.) (gray portion of the conceptual view of FIG. 7 (5)) is present as the second epithelial tissue. As shown in the conceptual view (4) of FIG. 7, non-target tissue may be contained inside the cell aggregate containing a transplant neural retina. This case does not apply to the definition "having the continuity of the slope of a tangent line to a surface different from the continuity of the slope of a tangent line to the surface of the first epithelial tissue", and therefore does not apply to the second epithelial tissue. It is preferable that the transplant neural retina and the sample for quality evaluation should be selected from a cell aggregate that does not contain non-target tissue in the inside.

<Sampling Step>

In the case of dissecting a transplant neural retina from a cell aggregate, it is desirable to use containing a marker-positive cell of a photoreceptor cell or a photoreceptor progenitor cell as an index. In the case of dissecting a transplant neural retina from a cell aggregate, it is desirable to use containing a marker-positive cell of a retinal progenitor cell or a neural retinal progenitor cell as an index. It is also desirable to use not containing a marker-positive cell of a non-target cell as an index.

For obtaining a transplant neural retina that contains a marker-positive cell of a photoreceptor cell or a photoreceptor progenitor cell and contains a marker-positive cell of a non-target cell below a certain level (or is negative to a non-target cell marker), it is desirable to evaluate the quality of the transplant neural retina in advance.

The quality of the transplant neural retina can be evaluated, for example, by sampling a part or the whole of a cell aggregate containing a neural retina having an epithelial structure derived from a pluripotent stem cell as a sample for quality evaluation (hereinafter, referred to as "sampling step"), and detecting a marker expressed in the obtained sample by a method known to those skilled in the art. The sampling of a part of the cell aggregate as the sample for quality evaluation means selecting some (one or more) cell aggregates, or all cell aggregates from among a plurality of cell aggregates, and isolating (e.g., dissecting) a portion of the selected cell aggregates as the sample for evaluation using tweezers, scissors and/or a knife, etc. The sampling of the whole of the cell aggregate as the sample for quality evaluation means selecting some (one or more) cell aggregates from among a plurality of cell aggregates, and separately picking up the whole of the selected one or more cell aggregates as the sample for quality evaluation. In the case of selecting one or more cell aggregates from among a plurality of cell aggregate, random sampling is preferable. In the specification, the cell aggregate in the case of sampling a part of the cell aggregate as the sample for quality evaluation is referred to as "cell aggregate containing the sample for quality evaluation", and the cell aggregate in the case of sampling the whole of the cell aggregate as the sample for quality evaluation is referred to as "cell aggregate of the sample for quality evaluation".

In an embodiment, the sample for quality evaluation is a part of a cell aggregate containing a neural retina having an epithelial structure derived from a pluripotent stem cell. By sampling a part of the cell aggregate as the sample for quality evaluation, there is an advantage that a neural retina contained in the remaining portion can be used in transplantation without completely destroying the cell aggregate. Specifically, provided that the sample for quality evaluation which is a part of the cell aggregate is determined as being accepted by a determination step mentioned later, a neural retina having an epithelial structure in the cell aggregate containing the sample for quality evaluation is regarded as being applicable as the transplant neural retina and can be used in transplantation.

In the cell aggregate, it can be determined that a site having a continuous epithelium structure where an outer neuroblastic layer and an inner neuroblastic layer appear to be divided as two layers is the neural retina. On the other hand, eyeball-related tissue as the second epithelial tissue, particularly, retinal pigment epithelial cells, assume black color visually or under a microscope and therefore, can readily be distinguished from the neural retina by those skilled in the art. Also, brain and spinal cord tissue as the second epithelial tissue, visually or under a microscope, cannot be confirmed to have a continuous epithelium structure, which is a morphological feature, on the surface of the cell aggregate, cannot be confirmed to have morphological features intrinsic to the neural retina, and/or appears to have a dull color, and thus, can readily be distinguished from the neural retina by those skilled in the art by focusing thereon. Thus, those skilled in the art can isolate the transplant neural retina and the sample for quality evaluation from the first epithelial tissue containing the neural retina even in a cell aggregate containing the second epithelial tissue.

As mentioned above, in an embodiment, the sample for quality evaluation is set and sampled depending on a predetermined positional relationship with the transplant neural retina or a candidate of the transplant neural retina. In other words, a region to be dissected as the sample for quality evaluation can be fixed by the setting of the transplant neural retina or its candidate. In this context, in an embodiment, the transplant neural retina (also referred to as a graft or a cap) and its candidate can be defined by the position in the cell aggregate mentioned above (e.g., being the center and/or its neighborhood of the epithelial tissue (continuous epithelial tissue), and in the case of having the second epithelial tissue, being a region on the first epithelial tissue most distant from the second epithelial tissue), and a size described in (Transplant neural retina sheet) mentioned later, etc. Thus, those skilled in the art can set a neural retina having these features as the transplant neural retina or its candidate.

In the case of sampling the transplant neural retina and the sample for quality evaluation from the same cell aggregate, the sample for quality evaluation (also referred to as a ring) can be set as a region continuous or adjacent at least partially to the transplant neural retina set as mentioned above, and a region as narrow as possible within a range that permits quality evaluation, by those skilled in the art. In the case of sampling a part of one or more cell aggregates among the cell aggregates of the same lot as the sample for quality evaluation, the sample for quality evaluation can be sampled as the transplant neural retina mentioned above or its candidate portion in the cell aggregates by those skilled in the art. In this case, a size to be dissected as the sample for quality evaluation may be a size described in (Transplant neural retina sheet) mentioned later, or may be smaller. Thus, the sample for quality evaluation can be set and sampled depending on the positional relationship with the transplant neural retina or its candidate and the size.

<Detection Step>

The method for evaluating the quality of a transplant neural retina according to the present invention comprises detecting the expression of a neural retina-related cell-related gene and a non-neural retina-related cell-related gene (non-target cell-related gene) in the sample for quality evaluation (detection step). It is preferable for the detection step to quantitatively detect the expression levels of the genes. The non-target cell-related gene comprises one or more genes selected from the group consisting of brain and spinal cord tissue marker gene and eyeball-related tissue marker gene.

(Neural Retina-Related Cell-Related Gene)

The neural retina-related cell-related gene (target cell-related gene) means a gene expressed by neural retina-related cells. As the neural retina-related cell-related gene, a gene highly expressed in photoreceptor cells (rod photoreceptor cell, cone photoreceptor cell), horizontal cells, amacrine cells, intermediate neuronal cells, retinal ganglion cells (ganglion cell), bipolar cells (rod bipolar cell, cone bipolar cell), Muller glial cells, or progenitor cells of these cells, neural retinal progenitor cells, or the like as compared with non-target cells is preferable. Examples of the neural retina-related cell-related gene include the neural retina-related cell markers described above, and RAX, Chx10, SIX3, SIX6, RCVRN, CRX, NRL and NESTIN are preferable. GenBank IDs of the neural retina-related cell markers are shown in Table 1 below.

TABLE 1

| Gene name | GenBank ID |
| --- | --- |
| RAX | NM_013435.2 |
| Chx10 | NM_182894.2 |
| SIX3 | NM_005413.4 |

TABLE 1-continued

| Gene name | GenBank ID |
|---|---|
| SIX6 | NM_007374.2 |
| RCVRN | NM_002903.2 |
| CRX | NM_000554.6 |
| NRL | NM_006177.4 |
| NESTIN | NM_006617.2 |

The neural retina-related cell-related gene is preferably the gene described in Table 1, though not limited thereto. Other examples of the neural retina-related cell-related gene include Rax2, Vsx1, Blimp1, RXRG, S-opsin, M/L-opsin, rhodopsin, Brn3, and L7.

(Non-Neural Retina-Related Cell-Related Gene)

Identification can be performed by detecting a gene (hereinafter, referred to as non-neural retina-related cell-related gene or non-target cell-related gene) expressed in a non-target cell induced as a by-product in the process of producing the cell aggregate containing a neural retina as a medicine raw material, or a cell or tissue having the possibility that the non-target cell is produced as a by-product.

In an embodiment, examples of the non-neural retina-related cell-related gene (non-target cell-related gene) include brain and spinal cord tissue marker gene and eyeball-related tissue marker gene. In an embodiment, as the non-neural retina-related cell-related gene, undifferentiated iPS cell marker gene may be contained.

In an embodiment, the brain and spinal cord tissue marker gene may be one or more genes selected from the group consisting of telencephalon marker gene, diencephalon/midbrain marker gene and spinal cord marker gene. The diencephalon/midbrain marker gene may be one or more genes selected from the group consisting of diencephalon marker gene, midbrain marker gene, and hypothalamus marker gene regarding the hypothalamus which is a part of the diencephalon.

In an embodiment, the eyeball-related tissue marker gene may be one or more genes selected from the group consisting of optic stalk marker gene, ciliary body marker gene, lens marker gene and retinal pigment epithelium marker gene.

The telencephalon marker gene means a gene expressed in the telencephalon. The telencephalon marker gene may comprise one or more genes selected from the group consisting of FoxG1 (also called Bf1), Emx2, Dlx2, Dlx1 and Dlx5. GenBank IDs of the telencephalon marker genes are shown in Table 2 below.

TABLE 2

| Gene name | GenBank ID |
|---|---|
| FOXG1 | NM_005249.4 |
| Emx2 | NM_004098.4 |
| | NM_001165924.1 |
| DLX2 | NM_004405.4 |
| DLX1 | NM_178120.5 |
| | NM_001038493.1 |
| DLX5 | NM_005221.6 |
| | XM_005250185.3 |
| | XM_017011803.1 |

The telencephalon marker gene is preferably the gene described in Table 2, though not limited thereto. Other examples of the telencephalon marker gene include Emx1, LHX2, LHX6, LHX7, and Gsh2.

The diencephalon/midbrain marker gene means a gene expressed in the diencephalon and/or the midbrain. The diencephalon/midbrain marker gene may comprise one or more genes selected from the group consisting of OTX1, OTX2 and DMBX1. GenBank IDs of the diencephalon/midbrain marker genes are shown in Table 3 below. The diencephalon/midbrain marker gene may comprise a hypothalamus marker mentioned later regarding the hypothalamus which is a region of the diencephalon. In other words, the diencephalon/midbrain marker gene may comprise one or more genes selected from the group consisting of OTX1, OTX2, OTX2, DMBX1, Rx, Nkx2.1, OTP, FGFR2, EFNA5 and GAD1.

TABLE 3

| Gene name | GenBank ID |
|---|---|
| OTX1 | NM_001199770.1 |
| | NM_014562.4 |
| OTX2 | NM_001270523.1 |
| | NM_001270524.1 |
| | NM_001270525.1 |
| | NM_021728.3 |
| | NM_172337.2 |
| DMBX1 | NM_172225.1 |
| | NM_147192.2 |
| | XM_011540668.2 |
| | XM_017000289.1 |

The hypothalamus marker gene means a gene expressed in the hypothalamus. The hypothalamus marker gene may comprise one or more genes selected from the group consisting of Rx, Nkx2.1, Dmbx1, OTP, gad1, FGFR2 and EFNA5. GenBank IDs of the hypothalamus marker gene are shown in Table 4 below.

TABLE 4

| Gene name | GenBank ID |
|---|---|
| Rx | NM_013435.2 |
| Nkx2.1 | NM_003317.3, NM_001079668.2 |
| OTP | NM_032109.2 |
| gad1 | NM_000817.3, NM_013445.3 |
| | XM_005246444.3, XM_011510922.1 |
| | XM_017003756.1, XM_017003758.2 |
| | XM_017003757.2, XM_024452783.1 |
| FGFR2 | NM_022970.3, NM_000141.4 |
| | NM_023029.2, NM_001144913.1 |
| | NM_001144914.1, NM_001144915.1 |
| | NM_001144916.1, NM_001144917.1 |
| | NM_001144918.1, NM_001144919.1 |
| | NM_001320654.1, NM_001320658.1 |
| | NR_073009.1, XM_006717708.3 |
| | XM_006717710.4, XM_017015920.2 |
| | XM_017015921.2, XM_017015924.2 |
| | XM_017015925.2, XM_024447888.1 |
| | XM_024447887.1, XM_024447890.1 |
| | XM_024447889.1, XM_024447892.1 |
| | XM_024447891.1 |
| EFNA5 | NM_001962.3, XM_006714565.3 |
| | XM_011543250.3, XM_011543251.2 |
| | XM_017009205.1 |

The spinal cord marker gene means a gene expressed in the spinal cord. The spinal cord marker gene may comprise one or more genes selected from the group consisting of HoxB2, HoxA5, HOXC5, HOXD1, HOXD3 and HOXD4. GenBank IDs of the spinal cord marker gene are shown in Table 5 below.

TABLE 5

| Gene name | GenBank ID |
|---|---|
| HOXB2 | NM_002145.3 |
| | XM_005257275.4 |
| HOXA5 | NM_019102.4 |
| HOXC5 | NM_018953.3 |
| | NR_003084.2 |
| HOXD1 | NM_024501.3 |
| HOXD3 | NM_006898.4 |
| | XM_005246509.4 |
| | XM_005246511.4 |
| | XM_005246513.5 |
| | XM_011511065.3 |
| | XM_011511066.3 |
| HOXD4 | NM_014621.3 |
| | XM_005246514.4 |

The spinal cord marker gene is preferably the gene described in Table 5, though not limited thereto. Other examples of the spinal cord marker gene include a gene group forming the Hox cluster.

Meanwhile, in an embodiment, in the case of using retinoids (examples thereof include retinoic acid, retinal, retinol, all-trans-retinoic acid, and 11-cis-retinoic acid) in a production step, the expression of HOX gene (e.g., HOXC5, HOXA5 and HOXB2) may be found even if a good product of retinal tissue is produced. It is considered that the expression of the HOX gene is regulated by retinoic acid signals, and the HOX gene expression increases to an extent that does not influence differentiation into retinal tissue. This effect of the retinoic acid signals is considered to be ascribable to the promotion of posterior shift along the anteroposterior axis. Thus, in the case of using retinoids in a production step (particularly, in the case of using retinoids at the time or later when differentiation into the retina has started), the HOX gene (e.g., HOXC5, HOXA5 and HOXB2) can be excluded from subject genes of quality evaluation, or the quality of a transplant neural retina can be determined as being good even if the expression of these genes is found.

The optic stalk marker gene means a gene expressed in the optic stalk. The optic stalk marker gene may comprise one or more genes selected from the group consisting of GREM1, GPR17, ACVR1C, CDH6, Pax2, Pax8, GAD2 and SEMA5A. GenBank IDs of the optic stalk marker genes are shown in Table 6 below.

TABLE 6

| Gene name | GenBank ID |
|---|---|
| GREM1 | NM_013372.7, NM_001191322.1 |
| | NM_001191323.1, NM_001368719.1 |
| | XM_017022077.1 |
| GPR17 | NM_001161417.1, NM_005291.2 |
| | NM_001161415.1, NM_001161416.1 |
| | XM_017003833.2 |
| ACVR1C | NM_145259.3, NM_001111031.1 |
| | NM_001111032.1, NM_001111033.1 |
| CDH6 | NM_004932.4, NM_001362435.1 |
| | XM_011513921.3, XM_017008910.2 |
| | XR_001741972.2 |
| Pax2 | NM_000278.4, NM_003987.4 |
| | NM_003988.4, NM_003989.4 |
| | NM_003990.4, NM_001304569.1 |
| Pax8 | NM_003466.4, NM_013952.3 |
| | NM_013953.3, NM_013992.3 |
| GAD2 | NM_001134366.2, NM_000818.2 |
| SEMA5A | NM_003966.3, XM_006714506.3 |
| | XM_006714507.3, XM_011514155.2 |
| | XM_011514156.2, XM_011514157.2 |

TABLE 6-continued

| Gene name | GenBank ID |
|---|---|
| | XM_011514158.2, XM_011514159.2 |
| | XM_017010016.2 |

The lens marker gene means a gene expressed in the lens. The lens marker gene may comprise one or more genes selected from the group consisting of CRYAA and CRYBA1. GenBank IDs of the lens marker genes are shown in Table 7 below.

TABLE 7

| Gene name | GenBank ID |
|---|---|
| CRYAA | NM_000394.3 |
| | NM_001363766.1 |
| CRYBA1 | NM_005208.4 |
| | XM_017024198.1 |

The ciliary body marker gene means a gene expressed in the ciliary body and/or the ciliary marginal zone. The ciliary body marker gene may comprise one or more genes selected from the group consisting of Zic1, MAL, HNF1beta, FoxQ1, CLDN2, CLDN1, GPR177, AQP1 and AQP4. GenBank IDs of the ciliary body marker genes are shown in Table 8 below.

TABLE 8

| Gene name | GenBank ID |
|---|---|
| Zic1 | NM_003412.4 |
| MAL | NM_002371.4, NM_022438.2 |
| | NM_022439.2, NM_022440.2 |
| HNF1beta | NM_000458.4, NM_001165923.3 |
| | NM_001304286.1, XM_011525160.1 |
| | XM_011525161.1, XM_011525162.2 |
| | XM_011525163.2, XM_011525164.1 |
| FoxQ1 | NM_033260.4 |
| CLDN2 | NM_001171092.1, NM_020384.3 |
| | NM_001171095.1 |
| CLDN1 | NM_021101.5 |
| GPR177 | NM_024911.7, NM_001002292.3 |
| | NM_001193334.1, XM_011542191.2 |
| | XM_011542192.3, XM_017002390.2 |
| AQP1 | NM_198098.3, NM_001329872.1 |
| AQP4 | NM_001650.7, NM_004028.4 |
| | NM_001317384.2, NM_001317387.2 |
| | NM_001364286.1, NM_001364287.1 |
| | NM_001364289.1, XM_011525942.3 |

The retinal pigment epithelium marker gene means a gene expressed in retinal pigment epithelial cells. Examples of the retinal pigment epithelium marker gene include the retinal pigment epithelium markers described above, and may comprise one or more genes selected from the group consisting of MITF, TTR and BEST1. GenBank IDs of the retinal pigment epithelium marker genes are shown in Table 9 below.

TABLE 9

| Gene name | GenBank ID |
|---|---|
| MITF | NM_000248.3, NM_006722.2 |
| | NM_198158.2, NM_198159.2 |
| | NM_198177.2, NM_198178.2 |
| | NM_001184967.1, NM_001184968.1 |
| | NM_001354604.1, NM_001354605.1 |
| | NM_001354606.1, NM_001354607.1 |
| | NM_001354608.1 |

TABLE 9-continued

| Gene name | GenBank ID |
|---|---|
| BEST1 | NM_004183.4, NM_001139443.1<br>NM_001300786.1, NM_001300787.1<br>NM_001363591.1, NM_001363592.1<br>NM_001363593.1, NR_134580.1<br>XM_005274210.4, XM_005274215.4<br>XM_005274216.4, XM_005274219.4<br>XM_005274221.4, XM_011545229.3<br>XM_011545230.3, XM_011545233.3<br>XM_017018230.2, XR_001747952.2<br>XR_001747953.2, XR_001747954.2 |
| TTR | NM_000371.3 |

In an embodiment, the non-target cell-related gene may further comprise undifferentiated pluripotent stem cell marker gene.

The undifferentiated pluripotent stem cell marker gene may comprise one or more genes selected from the group consisting of Oct3/4, Nanog and lin28 Preferably, the undifferentiated pluripotent stem cell marker gene is one or more genes selected from the group consisting of Oct3/4, Nanog and lin28 GenBank IDs of the undifferentiated pluripotent stem cell marker genes are shown in Table 10 below.

TABLE 10

| Gene name | GenBank ID |
|---|---|
| Oct3/4<br>(POU5F1) | NM_002701.6, NM_203289.5<br>NM_001173531.2, NM_001285986.1<br>NM_001285987.1 |
| Nanog | NM_024865.4, NM_001297698.1 |
| lin28 | NM_024674.6, XM_011542148.2 |
| SOX2 | NM_003106.4 |
| KLF4 | NM_001314052.1, NM_004235.6 |
| c-Myc | NM_001354870.1, NM_002467.6 |
| Glis1 | NM_001367484.1, NM_147193.2<br>XM_017000409.1, XM_017000411.1<br>XM_017000408.1, XM_017000410.1<br>XM_017000412.1 |
| Sall4 | NM_001318031.1, NM_020436.5<br>XM_011528921.2, XM_011528922.2<br>XM_005260467.4 |
| Esrrb | NM_004452.3, XM_011536553.2<br>XM_024449508.1, XM_011536547.2<br>XM_011536554.2, XM_011536550.2<br>XM_024449509.1, XM_017021085.1 |

(Detection Approach)

In an embodiment, although the detection of the expression of the neural retina-related cell-related gene and the non-neural retina-related non-target cell-related gene is not particularly limited, examples thereof include approaches such as Western blotting, immunostaining, flow cytometry analysis/flow cytometers (FACS® manufactured by Becton, Dickinson and Company), etc.), Northern blotting, electrophoresis, PCR (preferably, quantitative PCR (qPCR) and/or real-time PCR), gene chip analysis, and next-generation sequencers. Among them, quantitative PCR is useful from the viewpoint of quantitativeness, detection sensitivity, stability of results and rapidness. Furthermore, by applying an apparatus that is used for performing single-cell quantitative PCR (e.g., Biomark HD (manufactured by Fluidigm Corp.)) to usual quantitative PCR, it is possible to evaluate a plurality of samples for quality evaluation in a short time.

In an embodiment, the respective expression levels of the neural retina-related cell-related gene and the non-neural retina-related cell-related gene in two or more samples for quality evaluation may be simultaneously detected by quantitative PCR. The quantitative PCR may be performed by, for example, a method comprising the following steps (1) to (5). Specific methods are known to those skilled in the art.

(1) Providing a flow channel plate having one sample well group consisting of 8 or more and 800 or less independent sample wells, one or more primer well groups consisting of 8 or more and 800 or less independent primer wells, and flow channels connecting the independent sample wells in the sample well group with the independent primer wells in each primer well group, solutions containing nucleic acids obtained from the two or more of the samples for quality evaluation (sample solutions), and a solution containing one or a plurality of primers specific for each of one or more of the neural retina-related cell-related genes or the non-neural retina-related cell-related genes (primer solution);

(2) adding the sample solutions at one sample solution/one sample well for each of the samples for quality evaluations to the sample well group;

(3) adding the primer solution to one or more primer wells in the one or more primer well groups so as to be different primer well groups;

(4) separately mixing the primers with the nucleic acids via the flow channels; and (5) performing quantitative PCR using the mixture obtained in (4).

Flow cytometry analysis using a flow cytometer capable of detecting the ratios of expressing cells is also useful. In recent years, improvement in detection rate has advanced, and a flow cytometer capable of evaluating multiple samples with high-throughput properties (FACS®, etc.) is also available. Thus, for the detection of the expression of the neural retina-related cell-related gene and the non-neural retina-related non-target cell-related gene, use of a high-throughput flow cytometer is also useful. It is possible for such a high-throughput flow cytometer to use a commercially available product (e.g., MACSQuant® Analyzers: manufactured by Miltenyi Biotec).

<Determination Step>

It can be determined that, when the expression of the neural retina-related cell-related gene is found and the expression of the non-neural retina-related cell-related gene is not found, the transplant retinal tissue, preferably the transplant neural retina sheet, dissected from the cell aggregate is applicable to transplantation, i.e., is suitable for transplantation (determination step).

"The expression of the neural retina-related cell-related gene is found" means that, for a detection method for gene expression, the expression of the neural retina-related cell-related gene at a level substantially detectable by the detection method (e.g., detection lower limit value or more) is found. Also, "the expression of the non-neural retina-related cell-related gene is not found" means that, for a detection method for gene expression, the expression of the non-neural retina-related cell-related gene cannot be substantially detected by the detection method (e.g., less than detection lower limit value). The substantial detectability means that the gene is detected beyond an extent that cannot regard the gene as substantially functioning. Those skilled in the art are appropriately capable of setting it according to the genes and the detection method. For example, in the case of a detection method for gene expression with quantitativeness, it can be determined that the range of more than 0% to 10% or less or more than 0% to 5% or less with reference to the detection lower limit value of the gene expression is not the substantially detectable level (i.e., the expression of the gene cannot be detected).

In an embodiment, it is preferable to determine being applicable as the transplant neural retina when the following reference 1 and reference 2 are satisfied in the quantitative PCR:

reference 1: the difference between the threshold cycle (Ct) value of the neural retina-related cell-related gene and the Ct value of an internal standard gene (ΔCt value) is 10 or less, and reference 2: the difference between the Ct value of the non-neural retina-related cell-related gene and the Ct value of the internal standard gene (ΔCt value) is 5 or more.

The threshold cycle (Ct) value means the number of cycles that reaches a predetermined amount of an amplification product in a region where the amplification of a gene by PCR occurs exponentially. The Ct value has an inverse correlation with the initial amount of the gene and as such, is used in the calculation of the initial copy number of the gene. In an embodiment, the "2ˆCt value (Ct value power of 2)" is inversely proportional to the initial amount of the gene and as such, is used in the calculation of the initial copy number of the gene. Specifically, a sample containing a 2-fold initial amount of a gene has a Ct value more rapid by one cycle than that of a sample containing the gene at only half the copy number before amplification. The predetermined amount of an amplification product can fall within the region where the amplification of a gene by PCR occurs exponentially, and can be set by those skilled in the art.

The internal standard gene means a gene whose difference in expression level is small among samples. As the internal standard gene, the one known to those skilled in the art can be appropriately used, and examples thereof include 18S ribosomal RNA, 13 actin, HPRT, a tubulin, transferrin receptor, ubiquitin, and GAPDH, with GAPDH being preferable.

The Ct value is inversely correlated with the initial amount of a gene and therefore depends on the expression level of the gene within cells. Specifically, when the concentration of a nucleic acid-containing solution is constant, the Ct value differs depending on the internal standard gene used and the difference between the Ct value of a predetermined gene and the Ct value of the internal standard gene (ΔCt value) is influenced by the internal standard gene used. In the specification, the ΔCt value is described with reference to a value with GAPDH used as the internal standard gene, unless otherwise specified.

In the case of using an internal standard gene other than GAPDH as the internal standard gene, the ΔCt values of the reference 1 and the reference 2 can be corrected by comparing the expression levels of GAPDH and the internal standard gene other than GAPDH.

In an embodiment, in the case of using β actin as the internal standard gene, the Ct value of GAPDH is lower by about 1 than the Ct value of β actin, i.e., the absolute amount of GAPDH RNA is about twice the absolute amount of β actin RNA, as to GAPDH and β actin in the production method of the present application. Therefore, reference 1: the difference between the threshold cycle (Ct) value of the neural retina-related cell-related gene and the Ct value of an internal standard gene (ΔCt value) is 9 or less, and reference 2: the difference between the Ct value of the non-neural retina-related cell-related gene and the Ct value of the internal standard gene (ΔCt value) is 4 or more.

In an embodiment, in the case of using HPRT as the internal standard gene, the Ct value of GAPDH is lower by about 7 than that of HPRT, i.e., the absolute amount of GAPDH RNA is about 27 (128 times) of the absolute amount of HPRT RNA, as to GAPDH and HPRT in the production method of the present application. Therefore, reference 1: the difference between the threshold cycle (Ct) value of the neural retina-related cell-related gene and the Ct value of an internal standard gene (ΔCt value) is 3 or less, and reference 2: the difference between the Ct value of the non-neural retina-related cell-related gene and the Ct value of the internal standard gene (ΔCt value) is −2 or more.

The neural retina-related cell-related gene can be the gene mentioned above. As the neural retina-related cell-related gene, a plurality of genes are present. Specifically, even in the case of sampling it from the same neural retina-related cells, the Ct value of the reference 1 may differ depending on the type of the neural retina-related cell-related gene. Those skilled in the art can set a ΔCt value from which the expression of the neural retina-related cell-related gene can be determined on a gene basis, from known information such as the expression site or expression level of the neural retina-related cell-related gene.

For example, as for the Chx10 gene, when GAPDH is used as the internal standard, the ΔCt value may be 20 or less, preferably 15 or less, more preferably 10 or less.

For example, as for the recoverin gene, when GAPDH is used as the internal standard, the ΔCt value may be 16 or less, preferably 11 or less, more preferably 6 or less.

In general, the difference between the Ct value of the neural retina-related cell-related gene and the Ct value of the internal standard gene (e.g., GAPDH) (ΔCt value) may be, for example, 25 or less, 20 or less, 15 or less or 10 or less. The difference between the Ct value of the neural retina-related cell-related gene and the Ct value of the internal standard gene may be, for example, −10 or more, −5 or more, 0 or more or or more.

The non-neural retina-related cell-related gene can be the gene mentioned above. As the non-neural retina-related cell-related gene, a plurality of genes are present. Specifically, even in the case of sampling it from the same non-retinal cells, the Ct value differs depending on the non-neural retina-related cell-related gene. Those skilled in the art can set a ΔCt value from which the expression of the non-neural retina-related cell-related gene can be determined on a gene basis, from known information such as the expression site or expression level of the non-neural retina-related cell-related gene. For example, as for the PAX2 gene, when GAPDH is used as the internal standard, the ΔCt value may be 5 or more. As for the HOXB2 gene, when GAPDH is used as the internal standard, the ΔCt value may be 5 or more. In general, the difference between the Ct value of the non-neural retina-related cell-related gene and the Ct value of the internal standard gene may be 30 or less, 25 or less or 20 or less. Also, the difference between the Ct value of the non-neural retina-related cell-related gene and the Ct value of the internal standard gene may be, for example, 0 or more, 3 or more or 5 or more.

(Transplant Neural Retina Sheet)

In the specification, it is preferable that the transplant retinal tissue should be a transplant neural retina, and it is more preferable to be a transplant neural retina sheet comprising a neural retinal layer. The transplant neural retina sheet includes a transplant neural retina sheet having a front surface and a back surface, wherein the front surface constitutes an apical surface containing a neural retinal layer, the back surface constitutes a basal surface containing a basal membrane component, a thickness from the basal surface to the apical surface of the transplant neural retina sheet is from 100 μm to 1000 μm, a major axis of the transplant neural retina sheet is from 600 μm to 2500 μm, and a minor axis of the transplant neural retina sheet is from 200 μm to 1500 μm.

In an embodiment of the present invention, the transplant retinal tissue is a transplant neural retina sheet (1) being derived from a pluripotent stem cell, (2) having a three-dimensional structure, (3) comprising a neural retinal layer having a plurality of layer structures including a photoreceptor layer and an inner layer, (4) the photoreceptor layer comprising one or more cells selected from the group consisting of a photoreceptor progenitor cell and a photoreceptor cell, (5) the inner layer comprising one or more cells selected from the group consisting of a retinal progenitor cell, a ganglion cell, an amacrine cell and a bipolar cell, (6) the surface of the neural retinal layer having an apical surface, (7) the inner layer being present inside the photoreceptor layer present along the apical surface, (8) the area of the apical surface of the neural retinal layer being 50% or more with respect to the total area of the surface of the transplant neural retina sheet, (9) the area of a continuous epithelium structure being 80% or more with respect to the total area of the apical surface of the neural retinal layer, and

(10) the expression of neural retina-related cell-related gene being found and the expression of non-neural retina-related cell-related gene being not found in the transplant neural retina sheet, wherein the non-neural retina-related cell-related gene comprising one or more genes selected from the group consisting of brain and spinal cord tissue marker gene and eyeball-related tissue marker gene.

The transplant neural retina sheet (3) comprises a neural retinal layer having a plurality of layer structures including a photoreceptor layer and an inner layer. As described in (6) and (7), although the photoreceptor layer is present outside (surface) the transplant neural retina sheet, an ectopic photoreceptor layer may be present in the inner layer.

In the transplant neural retina sheet, (5) the inner layer comprises one or more cells selected from the group consisting of a retinal progenitor cell, a ganglion cell, an amacrine cell and a bipolar cell, but may comprise one or more cells selected from the group consisting of an ectopic photoreceptor progenitor cell and photoreceptor cell. In an embodiment, a transplant neural retina sheet in which the content of a ganglion cell, an amacrine cell and a horizontal cell is 30% or less of the total number of cells, a transplant neural retina sheet in which the content of a ganglion cell, an amacrine cell, a horizontal cell and a bipolar cell is 30% or less of the total number of cells, and/or a transplant neural retina sheet in which the content of a bipolar cell is 10% or less of the total number of cells is also provided.

In the transplant neural retina sheet, (8) the area of the neural retinal layer is 40% or more, preferably 50% or more, more preferably 60% or more, with respect to the total area of the surface of the transplant neural retina sheet. In the transplant neural retina sheet, (9) the area of a continuous epithelium structure is 60% or more, preferably 70% or more, more preferably 80% or more, with respect to the total area of the apical surface of the neural retinal layer.

The neural retina-related cell-related gene and the non-neural retina-related cell-related gene (brain and spinal cord tissue marker gene and eyeball-related tissue marker gene) are the genes mentioned above.

(10) The expression of neural retina-related cell-related gene being found and the expression of non-neural retina-related cell-related gene being not found in the transplant neural retina sheet can be revealed by isolating a part of the transplant neural retina sheet, and detecting the expression of the genes. For a transplant neural retina sheet isolated from a cell aggregate in which the expression of neural retina-related cell-related gene is substantially found and the expression of non-neural retina-related cell-related gene is not substantially found in a sample for quality evaluation by the method for evaluating the quality of a transplant neural retina mentioned above, the detection of gene expression in the transplant neural retina sheet itself is unnecessary. The expression of the gene being substantially found or the expression being not found is determined, as mentioned above, by the detection method for gene expression, depending on whether or not to be a level substantially detectable by the detection method.

The neural retina-related cell-related gene in the transplant neural retina sheet may be, for example, one or more selected from the group consisting of Rx, Chx10, Pax6 and Crx. The ratio of cells expressing the neural retina-related cell-related gene (positive cell) to the total number of cells differs depending on the stage of differentiation into the neural retina.

In an embodiment, the ratio of a Rx-positive cell to the total number of cells in the transplant neural retina sheet may be 30% or more, 40% or more, 50% or more, or 60% or more. In an embodiment, the ratio of a Chx10-positive cell or a Pax6-positive cell to the total number of cells in the transplant neural retina sheet may be 10% or more, 20% or more, 30% or more, 40% or more, or 50% or more. In an embodiment, the ratio of a Crx-positive cell to the total number of cells in the transplant neural retina sheet may be 10% or more, 20% or more, 30% or more, 40% or more, or 50% or more.

In an embodiment, the ratio of the Rx-positive cell to the total number of cells in the transplant neural retina sheet may be 30% or more and 80% or less, 40% or more and 70% or less, 45% or more and 60% or less, or 50% or more and 60% or less. In an embodiment, the ratio of the Chx10-positive cell or the Pax6-positive cell to the total number of cells in the transplant neural retina sheet may be 10% or more and 80% or less, 20% or more and 70% or less, 30% or more and 60% or less, or 40% or more and 50% or less. In an embodiment, the ratio of the Crx-positive cell to the total number of cells in the transplant neural retina sheet is 10% or more and 70% or less, 10% or more and 60% or less, 20% or more and 60% or less, 30% or more and 60% or less, 40% or more and 60% or less, or 50% or more and 60% or less.

In an embodiment, (1) the ratio of a Chx10-positive and Pax6-positive cell (neural retinal progenitor cell) may be 10% or more and 50% or less or 10% or more and 30% or less, (2) the ratio of a Chx10-positive and Pax6-negative cell (progenitor cell biased toward a bipolar cell) may be 10% or more and 25% or less or 15% or more and 25% or less, and (3) the ratio of a Chx10-negative and Pax6-positive cell (ganglion cell and amacrine cell) may be 10% or more and 25% or less or 10% or more and 20% or less, to the total number of cells in the transplant neural retina sheet.

In another embodiment, (1) the ratio of the Chx10-positive and Pax6-positive cell (neural retinal progenitor cell) may be 20% or more and 40% or less, (2) the ratio of the Chx10-positive and Pax6-negative cell (progenitor cell biased toward a bipolar cell) may be 5% or more and 20% or less, and (3) the ratio of the Chx10-negative and Pax6-positive cell (ganglion cell and amacrine cell) may be 5% or more and 20% or less or 5% or more and 15% or less, to the total number of cells in the transplant neural retina sheet.

In an embodiment, the transplant neural retina sheet according to the present invention is a transplant neural retina determined as being applicable as the transplant neural retina by the method for evaluating the quality of a transplant neural retina, and may be an isolated sheet-shaped transplant neural retina.

In an embodiment, the transplant neural retina sheet according to the present invention has been isolated from a cell aggregate containing a neural retina, and may be a transplant neural retina sheet containing a region of the center and/or its neighborhood of continuous epithelial tissue in the cell aggregate.

In an embodiment, the transplant retinal tissue is a transplant neural retina sheet (1) has been isolated from a cell aggregate containing a neural retinal layer, (2) contains a region of the center and/or its neighborhood of continuous epithelial tissue in the cell aggregate, and (3) is from 600 μm to 2500 μm in major axis, from 200 μm to 1500 μm in minor axis, and from 100 μm to 1000 μm in thickness.

In an embodiment, the transplant neural retina sheet according to the present invention has been isolated from a cell aggregate containing a neural retina, a retinal pigment epithelial cell and a ciliary marginal zone structure, and may be a transplant neural retina sheet that has the continuity of the slope of a tangent line to a surface different from the continuity of the slope of a tangent line to the surface of a neural retinal epithelial structure, and contains a region on an epithelial structure most distant from a portion containing the retinal pigment epithelial cell.

In an embodiment, the transplant neural retina sheet according to the present invention has been isolated from a cell aggregate containing a neural retina and brain and spinal cord tissue, and may be a transplant neural retina sheet that has the continuity of the slope of a tangent line to a surface different from the continuity of the slope of a tangent line to the surface of a neural retinal epithelial structure, and contains a region on an epithelial structure most distant from a portion containing the brain and spinal cord tissue.

In an embodiment, the transplant neural retina sheet according to the present invention has been isolated from two or more cell aggregates each containing neural retinal epithelium, and may be a transplant neural retina sheet containing the central part of morphologically favorable and/or large-size neural retinal epithelium suitable for isolation thereamong.

In an embodiment, the transplant retinal tissue is a transplant neural retina sheet, and the transplant neural retina sheet (1) has been isolated from a cell aggregate containing at least first epithelial tissue and second epithelial tissue, wherein the first epithelial tissue contains a human neural retina, and the second epithelial tissue has the continuity of the slope of a tangent line to a surface different from the continuity of the slope of a tangent line to the surface of the first epithelial tissue, and contains a non-neural retina-related cell, (2) contains a region on the first epithelial tissue most distant from the second epithelial tissue, and (3) is from 600 μm to 2500 μm in major axis, from 200 μm to 1500 μm in minor axis, and from 100 μm to 1000 μm in thickness, wherein the second epithelial tissue is a tissue selected from the group consisting of eyeball-related tissue, brain and spinal cord tissue and other tissues different from the neural retina of the first epithelial tissue.

In an embodiment, the major axis of the transplant neural retina sheet according to the present invention may be, for example, from 300 μm to 3300 μm and is preferably from 600 μm to 2500 μm, more preferably from 1100 μm to 1700 μm.

In an embodiment, the minor axis of the transplant neural retina sheet according to the present invention may be, for example, from 100 μm to 2000 μm and is preferably from 200 μm to 1500 μm, more preferably from 400 μm to 1100 μm.

In an embodiment, the height of the transplant neural retina sheet according to the present invention may be, for example, from 50 μm to 1500 μm and is preferably from 100 μm to 1000 μm, more preferably from 200 μm to 700 μm.

In an embodiment, the volume of the transplant neural retina sheet according to the present invention may be, for example, from 0.001 $mm^3$ to 4.0 $mm^3$ and is preferably from 0.01 $mm^3$ to 1.5 $mm^3$, more preferably from 0.07 $mm^3$ to 0.57 $mm^3$.

Methods for measuring the major axis, minor axis and height of the transplant neural retina sheet are not particularly limited, and they can be measured, for example, from an image taken under a microscope. For example, a front image taken with a cut surface turned to an objective lens side, and a side image taken with the cut surface inclined so as to be perpendicular to an objective lens are taken under a stereo microscope as to the transplant neural retina sheet dissected from a cell aggregate, and they can be measured from the taken images. In this context, the major axis means the longest line segment among line segments connecting two end points on the sheet cross section in the front image, and the length thereof. The minor axis means the longest line segment among line segments connecting two end points on the sheet cross section in the front image and orthogonal to the major axis, and the length thereof. The height means the longest line segment among line segments orthogonal to the sheet cross section and having a point intersecting the sheet cross section and the apex of the retina sheet as end points, and the length thereof. The volume of the sheet means a volume calculated according to the following calculation expression by approximating a graft as being an ellipsoid halved such that the cross section passes through the major axis.

$$\text{Volume} = 2/3 \times \text{Ratio of the circumference of a circle } (\pi) \times (\text{Major axis}/2) \times (\text{Minor axis}/2) \times \text{Height}$$

The retinal tissue that may be administered using the vehicle of the present invention is not particularly limited.

In an embodiment, examples of the retinal tissue include retina sheets described in Bryce T. McLelland et al., IOVS, May 2018, Vol. 59, No. 6, p. 2586.

In an embodiment, as the retinal tissue, a retina sheet may be prepared from retinal tissue produced by production methods described in the following literatures.

Nakano, T. et al. Cell Stem Cell 10, 771-785 (2012).

Kawahara A. et al. Nature Communications, 6, p. 6286 (2015).

Kuwahara A, Yamasaki S, et al. Sci Rep. 2019 Dec. 12; 9(1):18936.

Lamba, D. A., Gust, J. & Reh, T. A. Cell Stem Cell 4, 73-79, (2009).
Zhu, J., Cifuentes, H., Reynolds, J. & Lamba, D. A. Cell Stem Cell 20,374-384.e375(2017)
Meyer, J. S. et al. Stem Cells 29, 1206-1218, (2011).
Zhong, X. et al. Nat Commun 5, doi:10.1038/ncomms5047 (2014).
Boucherie, C., et al. Stem Cells 31, 408-414, doi:10.1002/stem.1268 (2013).
Gonzalez-Cordero, A. et al. Nat Biotechnol 31, 741-747, (2013).
Mellough, C. B. et al. Stein Cells 33, 2416-2430, (2015).
Hallam, D. et al. Stein Cells, doi:10.1002/stem.2883 (2018).
Reichman, S et al. PNAS 111, 8518-8523, (2014).
Gagliardi, G. et al. Stein Cell Reports 11, 665-680, (2018).
Tucker, B. A., et al. Stein Cells Transl Med 2, 16-24, (2013).
Wahlin, K. J. et al. Sci Rep 7, 766, (2017).
DiStefano, T. et al. Stem Cell Reports 10, 300-313, (2018).

(Production of Retinal Tissue)

In the specification, the retinal tissue that is used for transplantation may be retinal tissue excised from a living body (e.g., a fetus), or may be retinal tissue obtained by differentiation from autologous or allogeneic pluripotent stem cells (e.g., embryonic stem cells (ES cells) established from the embryo within 14 days after fertilization, induced pluripotent stem cells (iPS cells)). The retinal tissue may be a neural retina containing a photoreceptor cell.

A method for providing retinal tissue from a living body is known to those skilled in the art. Specifically, the retinal tissue can be dissected under anesthesia.

Examples of the retinal tissue obtained by differentiation from pluripotent stem cells include retinal tissue obtained by suspension-culturing a cell aggregate formed from pluripotent stem cells under appropriate differentiation conditions.

In this context, the "pluripotent stem cells" that are used as a starting material can be induced from, e.g., a fertilized egg, a cloned embryo, germline stem cells, tissue stem cells and somatic cells. Examples of the pluripotent stem cells can include embryonic stem cells (ES cells), embryonic germ cells (EG cells) and induced pluripotent stem cells (iPS cells). Muse cells (Multi-lineage differentiating stress enduring cells) obtained from the mesenchymal stem cells (MSC) and GS cells prepared from germ cells (for example, testis) are included in the pluripotent stem cells.

Human embryonic stem cells were established in 1998 and have been used also for regenerative medicine. The method for producing embryonic stem cells is described, for example, in WO96/22362, WO02/101057, U.S. Pat. Nos. 5,843,780, 6,200,806, 6,280,718. The embryonic stem cells are available from a predetermined institution and also, commercially available. For example, human embryonic stem cells such as KhES-1, KhES-2 and KhES-3 are available from the Institute for Frontier Life and Medical Sciences, Kyoto University. Human embryonic stem cells such as Crx::Venus strain (derived from KhES-1) are available from RIKEN.

The "induced pluripotent stem cells" refers to cells having pluripotency, which is induced by reprogramming somatic cells by a method known in the art.

The induced pluripotent stem cells were established in mouse cells by Yamanaka et al., in 2006 (Cell, 2006, 126 (4), pp. 663-676). The induced pluripotent stem cells were also established in human fibroblasts in 2007. The induced pluripotent stem cells have pluripotency and self-renewal ability similarly to embryonic stem cells (Cell, 2007, 131 (5), pp. 861-872; Science, 2007, 318 (5858), pp. 1917-1920; Nat. Biotechnol., 2008, 26 (1), pp. 101-106).

The induced pluripotent stem cells more specifically refer to cells which are induced to be pluripotent by reprogramming somatic cells differentiated into, for example, fibroblasts and peripheral blood mononuclear cells, by allowing any one of sets of a plurality of genes selected from a reprogramming gene group containing Oct3/4, Sox2, Klf4, Myc (c-Myc, N-Myc, L-Myc), Glis1, Nanog, Sall4, lin28 and Esrrb to express. Examples of a preferable set of reprogramming factors may include (1) Oct3/4, Sox2, Klf4, and Myc (c-Myc or L-Myc) and (2) Oct3/4, Sox2, Klf4, Lin28 and L-Myc (Stem Cells, 2013; 31: 458-466).

Other than producing induced pluripotent stem cells through direct reprogramming by gene expression, the pluripotent stem cells can be artificially induced from somatic cells, for example, by adding a chemical compound (Science, 2013, 341, pp. 651-654).

Alternatively, an induced pluripotent stem cell strain is available. For example, human induced pluripotent cell strains established by Kyoto University, such as 201B7 cell, 201B7-Ff cell, 253G1 cell, 253G4 cell, 1201C1 cell, 1205D1 cell, 1210B2 cell and 1231A3 cell, are available form Kyoto University and iPS Academia Japan, Inc. As the induced pluripotent stem cell strains, for example, Ff-I01 cell, Ff-I14 cell and QHJI01s04 cell established by Kyoto University, are available from Kyoto University.

In the specification, the pluripotent stem cells are preferably embryonic stem cells or induced pluripotent stem cells, more preferably induced pluripotent stem cells.

In the specification, the pluripotent stem cells are human pluripotent stem cells, preferably human induced pluripotent stem cells (iPS cells) or human embryonic stem cells (ES cells).

Pluripotent stem cells such as human iPS cells can be subjected to maintenance culture and expansion culture performed by methods known to those skilled in the art.

A method for producing the retinal tissue described in the section 2 is not particularly limited, and it can be produced by a method known to those skilled in the art.

The retinal tissue described in the section 2 is preferably retinal tissue (neural retina) comprising a neural retinal layer. The neural retinal tissue that is used in transplantation may be a cell aggregate containing a neural retina or a retina sheet obtained by dissecting a portion thereof.

In the specification, the cell aggregate containing a neural retina has an epithelial structure and can be obtained by differentiating pluripotent stem cells.

An embodiment includes a method for producing the cell aggregate containing a neural retina using a differentiation factor. Examples of the differentiation factor include basal membrane preparations, BMP signaling pathway agonists, Wnt signaling pathway inhibitors, and IGF signaling pathway agonists. An embodiment includes a method for producing the cell aggregate containing a neural retina by self-organization. The self-organization refers to a mechanism under which a population of cells autonomically yields a complicated structure. The self-organization can be performed by, for example, SFEB (serum-free floating culture of embryoid bodies-like aggregates) (WO2005/12390) or SFEBq (WO2009/148170).

Examples of a method for forming a cell aggregate from pluripotent stem cells include SFEB (serum-free floating culture of embryoid bodies-like aggregates) (WO2005/12390) and SFEBq (WO2009/148170).

Examples of a method for differentiating pluripotent stem cells into retinal tissue include, but are not particularly limited to, methods disclosed in literatures such as WO2011/055855, WO2013/077425, WO2015/025967, WO2016/

063985, WO2016/063986, WO2017/183732, "PLoS One. 2010 Jan. 20; 5 (1): e8763", "Stem Cells. 2011 August; 29 (8):1206-18", "Proc Natl Acad Sci USA. 2014 Jun. 10; 111 (23): 8518-23", "Nat Commun. 2014 Jun. 10; 5: 4047", WO2012/173207, WO2015/053375, WO2015/053376, WO2015/068505, WO2017/043605, WO2017/183732, WO2019/017492, WO2019/054514, WO2019/054515, "Stem Cell Reports, 2 (2), 205-218 (2014)", "Cell Stem Cell, 10 (6), 771-785 (2012)", and "Nature Communications 6: 6286 (2015)".

Examples of a method for producing retinal tissue can include methods described in Bryce T. McLelland et al., IOVS, May 2018, Vol. 59, No. 6, p. 2586.

Other examples of the method for producing retinal tissue include methods described in the following literatures.

Nakano, T. et al. Cell Stem Cell 10, 771-785 (2012).
Kawahara A. et al. Nature Communications, 6, p. 6286 (2015).
Kuwahara A, Yamasaki S, et al. Sci Rep. 2019 Dec. 12; 9(1):18936.
Lamba, D. A., Gust, J. & Reh, T. A. Cell Stem Cell 4, 73-79, (2009).
Zhu, J., Cifuentes, H., Reynolds, J. & Lamba, D. A. Cell Stem Cell 20,374-384.e375(2017)
Meyer, J. S. et al. Stem Cells 29, 1206-1218, (2011).
Zhong, X. et al. Nat Commun 5, doi:10.1038/ncomms5047 (2014).
Boucherie, C., et al. Stem Cells 31, 408-414, doi:10.1002/stem.1268 (2013).
Gonzalez-Cordero, A. et al. Nat Biotechnol 31, 741-747, (2013).
Mellough, C. B. et al. Stem Cells 33, 2416-2430, (2015).
Hallam, D. et al. Stem Cells, doi:10.1002/stem.2883 (2018).
Reichman, S et al. PNAS 111, 8518-8523, (2014).
Gagliardi, G. et al. Stem Cell Reports 11, 665-680, (2018).
Tucker, B. A., et al. Stem Cells Transl Med 2, 16-24, (2013).
Wahlin, K. J. et al. Sci Rep 7, 766, (2017).
DiStefano, T. et al. Stem Cell Reports 10, 300-313, (2018).

In a specific embodiment, the cell aggregate containing a neural retina can be prepared by a method comprising the following steps (A), (B), (C) and (D):

(A) culturing pluripotent stem cells in a culture medium for pluripotent stem cell culture in the absence of feeder cells;
(B) forming a cell aggregate by suspension-culturing the cells obtained in the step (A);
(C) further suspension-culturing the cell aggregate obtained in the step (B) in a culture medium containing a BMP signaling pathway agonist; and
(D) suspension-culturing and maturing the cell aggregate obtained in the step (C).

The step (A) may further involve a TGFβ family signaling pathway inhibitor and/or a sonic hedgehog signaling pathway agonist.

Also, the step (B) may involve a sonic hedgehog signaling pathway agonist and/or a Wnt signaling pathway inhibitor, as mentioned later.

This method is also disclosed in, for example, WO2015/025967, WO2016/063985, and WO2017/183732. For more details, see WO2015/025967, WO2016/063985, WO2017/183732, WO2019/017492, WO2019/054514, WO2019/054515, etc.

The "culture medium for pluripotent stem cell culture" that is used in the step (A) is a culture medium that allows pluripotent stem cells to be cultured under feeder-free conditions. Examples of the culture medium include culture media containing a factor for maintaining undifferentiated state.

In the specification, the factor for maintaining undifferentiated state is not particularly limited as long as it is a substance having an action of suppressing the differentiation of pluripotent stem cells. Examples of the factor for maintaining undifferentiated state that is generally used by those skilled in the art can include FGF signaling pathway agonists, TGFβ family signaling pathway agonists, and insulin. Examples of the FGF signaling pathway agonist specifically include fibroblast growth factors (e.g., bFGF, FGF4, FGF8). Examples of the TGFβ family signaling pathway agonist include TGFβ signaling pathway agonists and Nodal/activin signaling pathway agonists. Examples of the TGFβ signaling pathway agonist include TGFβ1 and TGFβ2. Examples of the Nodal/activin signaling pathway agonist include Nodal, activin A, and activin B. In the case of culturing human pluripotent stem cells (human ES cells, human iPS cells), the culture medium in the step (A) preferably contains bFGF as the factor for maintaining undifferentiated state.

The concentration of the factor for maintaining undifferentiated state in the culture medium that is used in the step (A) is a concentration capable of maintaining the undifferentiated state of the pluripotent stem cells to be cultured, and can be appropriately set by those skilled in the art. For example, specifically, in the case of using bFGF as the factor for maintaining undifferentiated state in the absence of feeder cells, its concentration is usually on the order of 4 ng to 500 ng/mL, preferably on the order of 10 ng to 200 ng/mL, more preferably on the order of 30 ng to 150 ng/mL.

Many synthetic media have been developed or are commercially available as culture media for pluripotent stem cell cultures applicable under feeder-free conditions. Examples thereof include Essential 8 medium (manufactured by Life Technologies Corp.). The Essential 8 medium contains L-ascorbic acid-2-phosphate magnesium (64 mg/L), sodium selenium (14 μg/L), insulin (19.4 mg/L), $NaHCO_3$ (543 mg/L), transferrin (10.7 mg/L), bFGF (100 ng/mL), and the TGFβ family signaling pathway agonist (TGFβ1 (2 ng/mL) or Nodal (100 ng/mL)) as additives in DMEM/F12 medium (Nature Methods, 8, 424-429 (2011)). Examples of other commercially available feeder-free media include S-medium (manufactured by DS Pharma Biomedical Co., Ltd.), StemPro (manufactured by Life Technologies Corp.), hESF9 (Proc. Natl. Acad. Sci. USA. 2008 Sep. 9; 105 (36): 13409-14), mTeSR1 (manufactured by STEMCELL Technologies Inc.), mTeSR2 (manufactured by STEMCELL Technologies Inc.), TeSR-E8 (manufactured by STEMCELL Technologies Inc.), and StemFit (manufactured by Ajinomoto Co., Inc.). In the step (A), the present invention can be conveniently carried out by using these. By using these culture media, it is possible to perform the culture of pluripotent stem cells under feeder-free conditions. The culture medium that is used in the step (A) is, as one example, a serum-free medium that is not supplemented with any of the BMP signaling pathway agonist, the Wnt signaling pathway agonist and the Wnt signaling pathway inhibitor.

The culture medium that is used in the preparation of the cell aggregate containing a neural retina, i.e., the culture medium that is used in the steps (B), (C) and (D), can employ a basal medium for cell proliferation (also referred to as a basal medium), unless otherwise specified. The basal medium for cell proliferation is not particularly limited as long as the culture of cells is possible. A basal medium commercially available as a culture medium for cell proliferation can be appropriately used. Specifically, examples thereof can include culture media that can be used in the culture of animal cells, such as BME medium, BGJb medium, CMRL 1066 medium, Glasgow MEM (GMEM) medium, Improved MEM Zinc Option medium, IMDM medium, Medium 199 medium, MEM medium, Eagle MEM medium, αMEM medium, DMEM medium, F-12 medium, DMEM/F12 medium, IMDM/F12 medium, Ham's medium, RPMI 1640 medium, Fischer's medium, Leibovitz's L-15 medium and mixtures of these media. Alternatively, a culture medium supplemented with $N_2$ medium which is an assisted culture medium may be used.

In the specification, the TGFβ family signaling pathway inhibitor refers to a substance inhibiting the TGFβ family signaling pathway, i.e., the signaling pathway transduced by the Smad family. Specifically, examples thereof can include TGFβ signaling pathway inhibitors (e.g., SB431542, LY-364947, SB505124, A-83-01), Nodal/activin signaling pathway inhibitors (e.g., SB431542, A-83-01) and BMP signaling pathway inhibitors (e.g., LDN193189, dorsomorphin). These substances are commercially available and can be obtained.

In the specification, the sonic hedgehog (hereinafter, also referred to as "Shh") signaling pathway agonist is a substance capable of enhancing signal transduction mediated by Shh. Examples of the Shh signaling pathway agonist include SHH, partial peptides of SHH (e.g., sonic hedgehog N-terminus (Shh-N), recombinant human sonic hedgehog (C24II) N-terminus (SHH-C24II), recombinant mouse sonic hedgehog (C25II) N-terminus (SHH-C25II)), hedgehog family proteins other than Shh (e.g., Hh, IHH, DHH, EHH, TwHH), PMA (purmorphamine), and SAG (smoothened agonist).

In the step (A), the concentrations of the TGFβ family signaling pathway inhibitor and the sonic hedgehog signaling pathway agonist can be concentrations capable of inducting differentiation into retinal cells. For example, SB431542 is used at a concentration of usually 0.1 to 200 μM, preferably 2 to 50 μM. A-83-01 is used at a concentration of usually 0.05 to 50 μM, preferably 0.5 to 5 μM. LDN193189 is used at a concentration of usually 1 to 2000 nM, preferably 10 to 300 nM. SAG is used at a concentration of usually 1 to 2000 nM, preferably 10 to 700 nM. PMA is used at a concentration of usually 0.002 to 20 μM, preferably 0.02 to 2 μM.

In the culture of pluripotent stem cells under feeder-free conditions in the step (A), a suitable matrix may be used as a scaffold in order to provide a scaffold as a replacement for feeder cells to the pluripotent stem cells. Examples of the matrix that can be used as a scaffold include laminin (Nat Biotechnol 28, 611-615, (2010)), laminin fragments (Nat Commun 3, 1236, (2012)), basal membrane preparations (Nat Biotechnol 19, 971-974, (2001)), gelatin, collagen, heparan sulfate proteoglycan, entactin, and vitronectin.

The culture time of the pluripotent stem cells in the step (A) is not particularly limited within a range in which an effect of improving the quality of the cell aggregate to be formed in the step (B) can be achieved in the case of culture in the presence of the TGFβ family signaling pathway inhibitor and/or the sonic hedgehog signaling pathway agonist (e.g., from 100 nM to 700 nM), and is usually from 0.5 to 144 hours. In an embodiment, it is preferably from 2 to 96 hours, more preferably from 6 to 48 hours, further preferably from 12 to 48 hours, still further preferably from 18 to 28 hours (e.g., 24 hours).

The culture medium that is used in the step (B) may be a serum-containing medium or a serum-free medium. A serum-free medium is suitably used from the viewpoint of circumventing contamination with chemically undetermined components. In order to circumvent the complication of preparation, examples thereof include serum-free media supplemented with an appropriate amount of a serum replacement such as commercially available KSR. The amount of KSR added to the serum-free medium is usually from about 1% to about 30%, preferably from about 2% to about 20%.

For the formation of the aggregate, first, dispersed cells are prepared by the dispersion operation of the cells obtained in the step (A). The "dispersed cells" obtained by dispersion operation include a state in which 70% (preferably 80% or more) or more are single cells and 30% or less (preferably 20% or less) of 2- to 50-cell masses are present. The dispersed cells include a state in which the mutual adhesion (e.g., surface adhesion) of cells has been mostly lost.

A suspension of the dispersed cells is seeded into an incubator, and the dispersed cells are cultured under conditions of non-adhesive to the incubator, thereby causing the aggregation of a plurality of cells to form an aggregate. In an embodiment, when a predetermined number of dispersed stem cells is placed in each well of a multi-well plate (U-bottom, V-bottom) such as a 96-well plate and this is statically cultured, the cells aggregate rapidly, thereby forming one aggregate in each well (SFEBq). In the case of suspension-culturing cells using a 96-well plate, a liquid prepared so as to attain about $1\times10^3$ to about $1\times10^5$ cells (preferably about $3\times10^3$ to about $5\times10^4$ cells or about $4\times10^3$ to about $2\times10^4$ cells) per well is added to the wells, and the plate is left standing to form aggregates.

In an embodiment, the culture medium that is used in the step (B) contains a sonic hedgehog signaling pathway agonist.

In other words, in a specific embodiment, the cell aggregate containing a neural retina can be prepared by a method comprising the following steps (A), (B) and (C):

(A) culturing pluripotent stem cells in a culture medium containing a factor for maintaining undifferentiated state and optionally containing a TGFβ family signaling pathway inhibitor and/or a sonic hedgehog signaling pathway agonist in the absence of feeder cells;

(B) forming a cell aggregate by suspension-culturing the cells obtained in the step (A) in a culture medium containing a sonic hedgehog signaling pathway agonist; and (C) further suspension-culturing the cell aggregate obtained in the step (B) in a culture medium containing a BMP signaling pathway agonist.

As the sonic hedgehog signaling pathway agonist in the step (B), the one mentioned above can be used at the concentration mentioned above (e.g., from 10 nM to 300 nM). The sonic hedgehog signaling pathway agonist is preferably contained in the culture medium from the start of suspension culture. A ROCK inhibitor (e.g., Y-27632) may be added to the culture medium. The culture time is, for example, from 12 hours to 6 days. The culture medium that is used in the step (B) is, as one example, a culture medium that is not supplemented with one or more (preferably all) selected from the group consisting of a BMP signaling pathway agonist, a Wnt signaling pathway agonist, a TGFβ family signaling pathway inhibitor and a TGFβ family signaling pathway agonist.

In an embodiment, the cell aggregate in the step (B) is at a stage of differentiation where a pluripotency marker is expressed. Specifically, it is a state of differentiation where one or more markers selected from Oct3/4, Sox2, Klf4, Nanog, Sall4, lin28, Esrrb and Esrrb are detectable.

In the specification, the BMP signaling pathway agonist is a substance capable of enhancing the signaling pathway mediated by BMP. Examples of the BMP signaling pathway agonist include BMP protein such as BMP2, BMP4 and BMP7, GDF protein such as GDF7, anti-BMP receptor antibodies, and BMP partial peptides. The BMP2 protein, the BMP4 protein and the BMP7 protein are available from, for example, R&D Systems, Inc., and the GDF7 protein is available from, for example, Wako Pure Chemical Industries, Ltd.

Examples of the culture medium that is used in the step (C) include serum-free media and serum media (preferably serum-free media) supplemented with a BMP signaling pathway agonist. The serum-free medium and the serum medium can be provided as mentioned above. The culture medium that is used in the step (C) is, as one example, a culture medium that is not supplemented with one or more (preferably all) selected from the group consisting of a Wnt signaling pathway agonist, a TGFβ family signaling pathway inhibitor and a TGFβ family signaling pathway agonist. Alternatively, the culture medium that is used in the step (C) is, as one example, a culture medium that is not supplemented with a sonic hedgehog signaling pathway agonist. Alternatively, the culture medium that is used in the step (C) is a culture medium that may be supplemented with a Wnt signaling pathway agonist.

The concentration of the BMP signaling pathway agonist can be a concentration capable of inducing differentiation into retinal cells. For example, human BMP4 protein is added to the culture medium so as to attain a concentration of about 0.01 nM to about 1 μM, preferably about 0.1 nM to about 100 nM, more preferably about 1 nM to about 10 nM, further preferably about 1.5 nM (55 ng/mL).

The BMP signaling pathway agonist can be added about 24 hours or later after the start of suspension culture in the step (A), and may be added to the culture medium within several days (e.g., within 15 days) after the start of suspension culture. Preferably, the BMP signaling pathway agonist is added to the culture medium between Day 1 and Day 15, more preferably between Day 1 and Day 9, most preferably on Day 3, after the start of suspension culture.

In a specific embodiment, a part or the whole of the culture medium is exchanged with a culture medium containing BMP4, for example, on Days 1 to 9, preferably Days 1 to 3, after the start of suspension culture in the step (B), and the medium is prepared such that the final concentration of BMP4 becomes about 1 to 10 nM. Culture can be performed for, for example, 1 to 12 days, preferably 2 to 9 days, further preferably 2 to 5 days, in the presence of BMP4. In this context, in order to maintain the concentration of BMP4 at the same concentration, a part or the whole of the culture medium can be exchanged with a culture medium containing BMP4 once or about twice. Alternatively, the concentration of BMP4 may be decreased in stages. For example, the concentration of the BMP signaling pathway agonist (BMP4) is maintained from Days 2 to 10 after the start of suspension culture in the step (B), and then, the concentration of the BMP signaling pathway agonist (BMP4) may be decreased in stages from Days 6 to 20 after the start of suspension culture in the step (B).

Culture conditions such as culture temperature and $CO_2$ concentration in the step (A) to the step (C) can be appropriately set. The culture temperature is, for example, from about 30° C. to about 40° C., preferably about 37° C. The $CO_2$ concentration is, for example, from about 1% to about 10%, preferably about 5%.

Retinal cells at various stages of differentiation can be produced as retinal cells contained in the cell aggregate by varying the culture period in the step (C). In other words, retinal cells in the cell aggregate containing immature retinal cells (e.g., retinal progenitor cell, photoreceptor progenitor cell) and matured retinal cells (e.g., photoreceptor cell) at various ratios can be produced. The ratio of matured retinal cells can be increased by extending the culture period in the step (C).

The step (B) and/or the step (C) may employ a method disclosed in WO2017/183732. Specifically, in the step (B) and/or the step (C), the cell aggregate can be formed by suspension culture in a culture medium further containing a Wnt signaling pathway inhibitor.

The Wnt signaling pathway inhibitor that is used in the step (B) and/or the step (C) is not particularly limited as long as it is capable of suppressing signal transduction mediated by Wnt, and may be any of a protein, a nucleic acid, a low-molecular compound, and the like. Signals mediated by Wnt are transduced via Wnt receptor present as a heterodimer of frizzled (Fz) and LRP5/6 (low-density lipoprotein receptor-related protein 5/6). Examples of the Wnt signaling pathway inhibitor include, but are not limited to, substances acting directly on Wnt or Wnt receptor (anti-Wnt neutralizing antibody, anti-Wnt receptor neutralizing antibody, etc.), substances suppressing the expression of a gene encoding Wnt or Wnt receptor (e.g., antisense oligonucleotide, siRNA), substances inhibiting the binding of Wnt to Wnt receptor (soluble Wnt receptor, dominant negative Wnt receptor, etc., Wnt antagonist, Dkk1, Cerberus protein, etc.), and substances inhibiting bioactivity caused by signal transduction ascribable to Wnt receptor [e.g., low-molecular compounds such as CKI-7 (N-(2-aminoethyl)-5-chloroisoquinoline-8-sulfonamide), D4476 (4-[4-(2,3-dihydro-1,4-benzodioxin-6-yl)-5-(2-pyridinyl)-1H-imidazol-2-yl]benzamide), IWR-1-endo (IWR1e) (4-[(3aR,4S,7R,7aS)-1,3,3a,4,7,7a-hexahydro-1,3-dioxo-4,7-methano-2H-isoindol-2-yl]-N-8-quinolinyl-benzamide), and IWP-2 (N-(6-methyl-2-benzothiazolyl)-2-[(3,4,6,7-tetrahydro-4-oxo-3-phenylthieno [3,2-d]pyrimidin-2-yl)thio]acetamide)]. One or two or more of these may be contained as the Wnt signaling pathway inhibitor. CKI-7, D4476, IWR-1-endo (IWR1e), IWP-2, and the like are known Wnt signaling pathway inhibitors, and commercially available products, etc. can be appropriately obtained. IWR1e is preferably used as the Wnt signaling pathway inhibitor.

The concentration of the Wnt signaling pathway inhibitor in the step (B) can be a concentration capable of inducing the favorable formation of the cell aggregate. For example, IWR-1-endo is added to the culture medium so as to attain a concentration of about 0.1 μM to about 100 μM, preferably about 0.3 μM to about 30 μM, more preferably about 1 μM to about 10 μM, further preferably about 3 μM. In the case of using a Wnt signaling pathway inhibitor other than IWR-1-endo, it is desirable to be used at a concentration that exhibits Wnt signaling pathway inhibitory activity equivalent to the concentration of IWR-1-endo.

In the step (B), the timing of adding the Wnt signaling pathway inhibitor to the culture medium is preferably earlier. The Wnt signaling pathway inhibitor is added to the culture medium usually within 6 days, preferably within 3 days, more preferably within 1 day, more preferably within 12 hours, from the start of suspension culture in the step (B), further preferably at the start of suspension culture in the step (B). Specifically, for example, the addition of a basal medium supplemented with the Wnt signaling pathway inhibitor, or the exchange of a part or the whole of the culture medium with the basal medium can be performed. Although a period for which the Wnt signaling pathway inhibitor is allowed to act on the cells obtained in the step (A) in the step (B) is not particularly limited, preferably, it is added to the culture medium at the start of suspension culture in the step (B) and then allowed to act until the completion of the step (B) (immediately before addition of a BMP signaling pathway agonist). Further preferably, as mentioned later, exposure to the Wnt signaling pathway inhibitor is continued even after the completion of the step (B) (i.e., during the period of the step (C)). In an embodiment, as mentioned later, the action of the Wnt signaling pathway inhibitor is continued even after the completion of the step (B) (i.e., during the period of the step (C)), and the action may be performed until retinal tissue is formed.

In the step (C), as the Wnt signaling pathway inhibitor, any of the Wnt signaling pathway inhibitors mentioned above can be used. Preferably, the same type as the Wnt signaling pathway inhibitor used in the step (B) is used in the step (C).

The concentration of the Wnt signaling pathway inhibitor in the step (C) can be a concentration capable of inducing retinal progenitor cells and retinal tissue. For example, IWR-1-endo is added to the culture medium so as to attain a concentration of about 0.1 μM to about 100 μM, preferably about 0.3 μM to about 30 μM, more preferably about 1 μM to about 10 μM, further preferably about 3 μM. In the case of using a Wnt signaling pathway inhibitor other than IWR-1-endo, it is desirable to be used at a concentration that exhibits Wnt signaling pathway inhibitory activity equivalent to the concentration of IWR-1-endo. The concentration of the Wnt signaling pathway inhibitor in the culture medium in the step (C) is preferably 50 to 150, more preferably 80 to 120, further preferably 90 to 110, when the concentration of the Wnt signaling pathway inhibitor in the culture medium in the step (B) is defined as 100. It is more preferable to be equivalent to the concentration of the Wnt signaling pathway inhibitor in the culture medium in the second step.

The timing of addition of the Wnt signaling pathway inhibitor to the culture medium is not particularly limited within a range that can achieve the formation of an aggregate containing retinal cells or retinal tissue, and is preferably earlier. Preferably, the Wnt signaling pathway inhibitor is added to the culture medium at the start of the step (C). More preferably, the Wnt signaling pathway inhibitor is added in the step (B) and then also continuously (i.e., from the start of the step (B)) contained in the culture medium in the step (C). Further preferably, the Wnt signaling pathway inhibitor is added at the start of suspension culture in the step (B) and then also continuously contained in the culture medium in the step (C). For example, a BMP signaling pathway agonist (e.g., BMP4) can be added to the cultures (suspension of aggregates in a culture medium containing a Wnt signaling pathway inhibitor) obtained in the step (B).

A period for which the Wnt signaling pathway inhibitor is allowed to act is not particularly limited, but is preferably from 2 days to 30 days, more preferably from 6 days to 20 days, from 8 days to 18 days, from 10 days to 18 days, or from 10 days to 17 days (e.g., 10 days), with the start of suspension culture in the step (B) as a commencement when the Wnt signaling pathway inhibitor is added at the start of suspension culture in the step (B). In another embodiment, the period for which the Wnt signaling pathway inhibitor is allowed to act is preferably from 3 days to 15 days (e.g., 5 days, 6 days, 7 days), more preferably from 6 days to 10 days (e.g., 6 days), with the start of suspension culture in the step (B) as a commencement when the Wnt signaling pathway inhibitor is added at the start of suspension culture in the step (B).

A neural retina having a ciliary marginal zone-like structure can also be produced by culturing the cell aggregate obtained by the method mentioned above in a serum-free medium or a serum medium containing a Wnt signaling pathway agonist and/or a FGF signaling pathway inhibitor for a period on the order of 2 days to 4 days (step (D)), followed by culture in a serum-free medium or a serum medium containing neither a Wnt signaling pathway agonist nor a FGF signaling pathway inhibitor for about 30 days to about 200 days (from 30 days to 150 days, from 50 days to 120 days, from 60 days to 90 days) (step (E)).

In an embodiment, a neural retina having a ciliary marginal zone-like structure can be produced by the step (D) and the step (E) from the cell aggregate obtained in the steps (A) to (C), the cell aggregate being of Days 6 to 30 or Days 10 to 20 (Day 10, Day 11, Day 12, Day 13, Day 14, Day 15, Day 16, Day 17, Day 18, Day 19 or Day 20) after the start of suspension culture in the step (B).

The Wnt signaling pathway agonist is not particularly limited as long as it is capable of enhancing signal transduction mediated by Wnt. Examples of a specific Wnt signaling pathway agonist can include GSK3β inhibitors (e.g., 6-bromoindirubin-3'-oxime (BIO), CHIR99021, kenpaullone). For example, in the case of CHIR99021, the range of about 0.1 μM to about 100 μM, preferably about 1 μM to about 30 μM, can be included.

The FGF signaling pathway inhibitor is not particularly limited as long as it can inhibit signal transduction mediated by FGF. Examples of the FGF signaling pathway inhibitor include SU-5402, AZD4547, and BGJ398. For example, SU-5402 is added at a concentration of about 0.1 μM to about 100 μM, preferably about 1 μM to about 30 μM, more preferably about 5 μM.

The culture medium that is used in the step (D) is, as one example, a culture medium that is not supplemented with one or more (preferably all) selected from the group consisting of a BMP signaling pathway agonist, a Wnt signaling pathway inhibitor, a SHH signaling pathway agonist, a TGFβ family signaling pathway inhibitor and a TGFβ family signaling pathway agonist.

A part of the step (E) or the whole step can perform culture using a culture medium for continuous epithelial tissue maintenance disclosed in WO2019/017492. Specifically, the continuous epithelium structure of the neural retina can be maintained by culture using a culture medium for continuous epithelial tissue maintenance. One example of the culture medium for continuous epithelial tissue maintenance can include a medium in which Neurobasal medium (e.g., manufactured by Thermo Fisher Scientific Inc., 21103049) is blended with B27 supplement (e.g., Thermo Fisher Scientific Inc., 12587010).

For the culture in the step (E), exchange with the culture medium for continuous epithelial tissue maintenance in stages is preferable for achieving both the differentiation and/or maturation of retinal cells (particularly, photoreceptor cell) and the maintenance of the continuous epithelium structure. For example, culture can be performed using a basal medium for cell proliferation (e.g., a culture medium in which DMEM/F12 medium is supplemented with 10% fetal bovine serum, 1% N2 supplement, and 100 μM taurine) for first 10 days to 30 days, a mixture of a basal medium for cell proliferation and a culture medium for continuous epithelial tissue maintenance (culture medium in which a medium in which DMEM/F12 medium is supplemented with 10% fetal bovine serum, 1% N2 supplement, and 100 μM taurine, and a medium in which Neurobasal medium is supplemented with 10% fetal bovine serum, 2% B27 supplement, 2 mM glutamine, and 100 μM taurine, are mixed at a ratio of 1:3) for next 10 days to 40 days, and a culture medium for continuous epithelial tissue maintenance (e.g., a culture medium in which Neurobasal medium is supplemented with 10% fetal bovine serum, 2% B27 supplement, 2 mM glutamine, and 100 μM taurine) for next 20 days to 140 days.

In a part of the step (E) or the whole step, in the case of using any medium of the basal medium for cell proliferation, the culture medium for continuous epithelial tissue maintenance or a mixture of these media, a thyroid hormone signaling pathway agonist may be further contained. By culture in a culture medium containing a thyroid hormone signaling pathway agonist, the production of a cell aggregate containing a neural retina becomes possible in which the ratio of bipolar cells, amacrine cells, ganglion cells or horizontal cells, etc. contained in the neural retina is low and the ratio of photoreceptor progenitor cells has been increased.

In the specification, the thyroid hormone signaling pathway agonist is a substance capable of enhancing signal transduction mediated by thyroid hormone, and is not particularly limited as long as it is capable of enhancing the thyroid hormone signaling pathway. Examples of the thyroid hormone signaling pathway agonist include triiodothyronine (hereinafter, also abbreviated to T3), thyroxin (hereinafter, also abbreviated to T4), and thyroid hormone receptor (preferably TRβ receptor) agonists.

Examples of the thyroid hormone receptor agonist known to those skilled in the art can include compounds such as diphenylmethane derivatives, diaryl ether derivatives, pyridazine derivatives, pyridine derivatives and indole derivatives described in International Publication No. WO 97/21993, International Publication No. WO 2004/066929, International Publication No. WO 2004/093799, International Publication No. WO 2000/039077, International Publication No. WO 2001/098256, International Publication No. WO 2003/018515, International Publication No. WO 2003/084915, International Publication No. WO 2002/094319, International Publication No. WO 2003/064369, Japanese Unexamined Patent Publication No. 2002-053564, Japanese Unexamined Patent Publication No. 2002-370978, Japanese Unexamined Patent Publication No. 2000-256190, International Publication No. WO 2007/132475, International Publication No. WO 2007/009913, International Publication No. WO 2003/094845, International Publication No. WO 2002/051805 or International Publication No. WO 2010/122980.

In the case of using T3 as the thyroid hormone signaling pathway agonist, it can be added to the culture medium so as to attain, for example, the range of 0.1 to 1000 nM. Preferably, examples thereof include concentrations having thyroid hormone signaling enhancing activity that corresponds to T3 with a concentration of 1 to 500 nM; more preferably to 100 nM; further preferably 30 to 90 nM; still more preferably around 60 nM. In the case of using T4 as the thyroid hormone signaling pathway agonist, it can be added to the culture medium so as to attain, for example, the range of 1 nM to 500 μM. Preferably, it is the range of 50 nM to 50 μM; more preferably 500 nM to 5 μM. In the case of using other thyroid hormone receptor agonists, the concentration can exhibit activity equivalent to the agonist activity exhibited by T3 or T4 with the concentration mentioned above.

The culture medium that is used in the step (E) may appropriately contain L-glutamine, taurine, serum, or the like. The culture medium that is used in the step (E) is, as one example, a culture medium that is not supplemented with one or more (preferably all) selected from the group consisting of a BMP signaling pathway agonist, a FGF signaling pathway inhibitor, a Wnt signaling pathway agonist, a Wnt signaling pathway inhibitor, a SHH signaling pathway agonist, a TGFβ family signaling pathway inhibitor and a TGFβ family signaling pathway agonist.

In a specific embodiment, the cell aggregate containing a neural retina can be prepared by a method comprising the following steps (A) to (E):

(A) culturing pluripotent stem cells in a culture medium containing a factor for maintaining undifferentiated state and optionally containing a TGFβ family signaling pathway inhibitor and/or a sonic hedgehog signaling pathway agonist in the absence of feeder cells;

(B) forming a cell aggregate by suspension-culturing the cells obtained in the step (A) in a culture medium optionally containing a Wnt signaling pathway inhibitor and/or a sonic hedgehog signaling pathway agonist;

(C) further suspension-culturing the cell aggregate obtained in the step (B) in a culture medium containing a BMP signaling pathway agonist;

(D) culturing the cell aggregate obtained in the step (C) in a serum-free medium or a serum medium containing a Wnt signaling pathway agonist and/or a FGF signaling pathway inhibitor for a period on the order of 2 days to 4 days; and (E) culturing the cell aggregate obtained in the step (D) in a serum-free medium or a serum medium containing neither a Wnt signaling pathway agonist nor a FGF signaling pathway inhibitor and optionally containing a thyroid hormone signaling pathway agonist for about 30 days to about 200 days.

In a specific embodiment, the cell aggregate containing a neural retina can be prepared by a method comprising the following steps (A) to (E):

(A) culturing pluripotent stem cells in a culture medium containing a factor for maintaining undifferentiated state and containing a TGFβ family signaling pathway inhibitor and/or a sonic hedgehog signaling pathway agonist in the absence of feeder cells for 12 hours to 48 hours;

(B) forming a cell aggregate by suspension-culturing the cells obtained in the step (A) in a culture medium containing a Wnt signaling pathway inhibitor and/or a sonic hedgehog signaling pathway agonist for 12 hours to 72 days (24 hours to 48 hours);

(C) further suspension-culturing the cell aggregate obtained in the step (B) in a culture medium containing a BMP signaling pathway agonist for 8 days to 15 days (10 days to 13 days);

(D) culturing the cell aggregate obtained in the step (C) in a serum-free medium or a serum medium containing a Wnt signaling pathway agonist and/or a FGF signaling pathway inhibitor for 2 days to 4 days; and (E) culturing the cell aggregate obtained in the step (D) in a serum-free medium or a serum medium containing neither a Wnt signaling pathway agonist nor a FGF signaling pathway inhibitor and optionally containing a thyroid hormone signaling pathway agonist for about 10 days to about 200 days.

In this context, the step (E) may comprise the step of performing culture in a basal medium for cell proliferation for 10 days to 30 days, subsequently performing culture in a mixture of a basal medium for cell proliferation and a culture medium for continuous epithelial tissue maintenance containing a thyroid hormone signaling pathway agonist for 10 days to 40 days, and further performing culture in a culture medium for continuous epithelial tissue maintenance containing a thyroid hormone signaling pathway agonist for 20 days to 140 days.

In an embodiment, the step (E) comprises performing culture in the presence of a thyroid hormone signaling pathway agonist for 20 days to 60 days (30 days to 50 days).

In an embodiment, the culture period from the step (B) to the step (E) is from 70 days to 100 days (from 80 days to 90 days).

The cell aggregate containing a neural retina can be produced by the method mentioned above, though not limited thereto. In an embodiment, the cell aggregate containing a neural retina can also be obtained as a mixture of cell aggregates. In another embodiment, for example, one cell aggregate may be produced per well of a 96-well plate, and cell aggregates containing a neural retina may be obtained one by one.

3. Composition for Transplantation

The composition for transplantation of the present invention comprises the vehicle for transplantation described in the section 1 and the transplant retinal tissue described in the section 2. The transplant retinal tissue is preferably the transplant neural retina sheet described in the section 2.

The composition for transplantation of the present invention comprises the transplant retinal tissue to be subjected to one transplantation to a recipient, i.e., a graft, and the vehicle for transplantation in a necessary amount for smoothly performing a procedure of aspirating the graft into a device for transplantation and subretinally discharging it to the recipient, without damaging the graft.

Specifically, the composition for transplantation of the present invention comprises, for example, 1 to 30 grafts in 5 to 500 μl of the composition for transplantation. Preferably, it comprises 1 to 2 grafts in to 50 μl of the composition for transplantation. In another embodiment, it comprises 3 to 4 grafts in 5 to 100 μl of the composition for transplantation. In an alternative embodiment, it comprises 5 to 6 grafts in 10 to 150 μl of the composition for transplantation. In an alternative embodiment, it comprises 7 to 10 grafts in 20 to 200 μl of the composition for transplantation. In an alternative embodiment, it comprises 11 to 30 grafts in 30 to 300 μl of the composition for transplantation. The grafts are preferably transplant neural retina sheets.

Specifically, the composition for transplantation of the present invention comprises, for example, 1 to 30 grafts in 5 to 500 μl of the composition for transplantation. In this context, the number of cells contained in one graft described above includes 10,000 to 1,000,000 cells, preferably 5,000 to 300,000 cells.

Preferably, it comprises 1 to 2 grafts (the number of cells is 10,000 to 2,000,000 cells, preferably 5,000 to 600,000 cells) in 5 to 50 μl of the composition for transplantation. In another embodiment, it comprises 3 to 4 grafts (the number of cells is 30,000 to 4,000,000 cells, preferably 15,000 to 1,200,000 cells) in 5 to 100 μl of the composition for transplantation. In an alternative embodiment, it comprises 5 to 6 grafts (the number of cells is 50,000 to 6,000,000 cells, preferably 25,000 to 1,800,000 cells) in 10 to 150 μl of the composition for transplantation. In an alternative embodiment, it comprises 7 to 10 grafts (the number of cells is 70,000 to 10,000,000 cells, preferably 35,000 to 3,000,000 cells) in 20 to 200 μl of the composition for transplantation. In an alternative embodiment, it comprises 11 to 30 grafts (the number of cells is 110,000 to 30,000,000 cells, preferably 55,000 to 9,000,000 cells) in 30 to 300 μl of the composition for transplantation.

In an aspect of the present invention, a pharmaceutical composition comprising the composition for transplantation of the present invention comprising the transplant retinal tissue and the vehicle for transplantation, is provided.

The pharmaceutical composition can be used in the treatment of a disease caused by the damage of a neural retina-related cell or a neural retina or the injury of a neural retina. Examples of the disease caused by the damage of a neural retina-related cell or a neural retina include ophthalmic diseases such as retinal degenerative diseases, macular degeneration, age-related macular degeneration, retinitis pigmentosa, glaucoma, corneal diseases, retinal detachment, central serous chorioretinopathy, cone dystrophy, and cone rod dystrophy. Examples of the injury state of a neural retina include a state in which photoreceptor cells die of degeneration.

In an aspect of the present invention, a therapeutic product for a disease caused by the damage of a neural retina, comprising the composition for transplantation of the present invention, is provided.

The composition for transplantation of the present invention can be prepared through the step of removing a vehicle for preservation from a composition containing a graft and the vehicle for preservation, and exchanging it with the vehicle for transplantation. In this context, one example of the vehicle for preservation includes, but is not particularly limited to, preservation solutions described in WO2019/017491.

4. Transplantation Method and Treatment Method

The composition for transplantation of the present invention can be subretinally injected and thereby transplanted to a mammal (e.g., a human, a mouse, a rat, preferably a human) having a retinal disease, for example, macular degeneration (e.g., atrophic and exudative age-related macular degeneration, Stargardt disease), hereditary retinal disease, retinitis pigmentosa (also referred to as retinal pigment degeneration), cone dystrophy, rod dystrophy, cone rod dystrophy, macular hole, giant macular hole, or glaucoma. Examples of a transplantation method include a method of subretinally transplanting the composition for transplantation to an injured site through an incision to an eyeball. Examples of a method for transplantation include a method of performing infusion using a device for transplantation including a syringe, a needle, or a plastic tip of appropriate size, and a method of performing transplantation by sandwiching between tweezers.

In the case of using the composition for transplantation of the present invention in the treatment of retinitis pigmentosa, it may be used in the treatment of, for example, corrected visual acuity less than 0.7, preferably visual acuity less than 0.2.

In the case of using the composition for transplantation of the present invention in the treatment of retinitis pigmentosa, examples thereof include diseases having tunnel vision, for example, a disease in which a central 20-degree visual field remains in static perimetry (which can be tested by Humphrey visual field test), preferably a disease in which a central 10-degree visual field remains in static perimetry (which can be tested by Humphrey visual field test), more preferably a disease in which a central 5-degree visual field remains in static perimetry (which can be tested by Humphrey visual field test). The composition for transplantation of the present invention can be transplanted to treat a retinal region that has lost visual functions.

In the case of using the composition for transplantation of the present invention in the treatment of retinitis pigmentosa, it may be used in the treatment of, for example, a MD value less than −30 dB in Humphrey visual field test (10-2).

In an aspect of the present invention, a method for treating a disease caused by the damage of a neural retina-related cell or a neural retina or the injury of a neural retina, comprising transplanting the composition for transplantation of the present invention to a subject in need of transplantation (e.g., subretinally to an eye having the ophthalmic disease), is also provided. As the therapeutic product for a disease caused by the damage of a neural retina, or in order to make up for a corresponding injured site in the injury state of the neural retina, the composition for transplantation of the present invention can be used. The disease caused by the damage of a neural retina-related cell or a neural retina, or the injury state of a neural retina can be treated by transplanting the composition for transplantation of the present invention to a patient having the disease caused by the damage of a neural retina-related cell or a neural retina, or a patient with the injury state of a neural retina, in need of transplantation, and making up for the neural retina-related cell or the damaged neural retina.

EXAMPLES

Hereinafter, the present invention will be described more specifically with reference to Examples. However, the present invention is not limited by these by any means.

Example 1: Study on Viscosity of Candidate of Vehicle for Transplantation

In order to establish an approach of subretinally transplanting a retinal tissue sheet having a size of 1 mm or more in major axis to a human, a vehicle for transplantation thereof was studied.

First, a preliminary study on surgery to subretinally transplant a retina sheet to a monkey was conducted. As a vehicle for transplantation, a balanced salt solution (BSS) containing neither hyaluronic acid nor chondroitin sulfate was used.

Posterior vitreous detachment was caused as needed by performing generally practiced vitreous stem microscopic transection using a cataract and vitrectomy surgery apparatus. A balanced salt solution was subretinally injected using the liquid injection function of the cataract and vitrectomy surgery apparatus to prepare localized retinal detachment (bleb). A partial incision was made in a retina at the site detached with vitreous scissors to form a wound for transplantation.

A plastic tip (tip for transplantation) was connected to a discharge apparatus, and a balanced salt solution containing a retina sheet was aspirated thereto. The tip for transplantation was inserted from an incision wound prepared in the sclera, and the tip for transplantation was allowed to reach the wound for transplantation prepared in the retina. The balanced salt solution containing a retina sheet was subretinally inserted using the liquid injection function of the cataract and vitrectomy surgery apparatus (see FIG. 1).

As a result, subretinal administration was difficult to carry out stably because the retina sheet moved around in the bleb.

Accordingly, the composition of the vehicle for transplantation was studied using the aqueous hyaluronic acid solutions shown in the following Table 11.

TABLE 11

| Product name | Viscoat 0.5 ophthalmic viscoelastic preparation | Opegan 0.6 or 1.1 ophthalmic viscoelastic preparation | Hyalein Mini ophthalmic solution 0.3% |
|---|---|---|---|
| Component | Sodium hyaluronate<br>Sodium dihydrogen phosphate<br>Sodium hydrogen phosphate<br>Chondroitin sulfate sodium salt<br>Tonicity agent | Sodium hyaluronate<br>Sodium chloride<br>Sodium dihydrogen phosphate<br>Sodium hydrogen phosphate | Sodium hyaluronate<br>Epsilon-aminocaproic acid<br>Sodium edetate hydrate<br>Potassium chloride<br>Sodium chloride<br>pH adjuster |

Specifically, as candidates of the vehicle for transplantation, the following vehicles were prepared:

(1) Viscoat stock solution,
(2) Viscoat diluted 2-fold (Viscoat:Opeguard=1:1),
(3) Viscoat diluted 4-fold (Viscoat:Opeguard=1:3),
(4) Hyalein Mini,
(5) Provisc,
(6) Healon,
(7) Opegan,
(8) Opegan diluted 1.5-fold (Opegan:Opeguard=2:1), and
(9) Opegan diluted 2-fold (Opegan:Opeguard=1:1).

Opeguard is, as mentioned above, an aqueous solution containing 1.5 mg of glucose, 0.18 mg of calcium chloride hydrate, 0.3 mg of magnesium sulfate hydrate, 2.1 mg of sodium bicarbonate, and sodium citrate hydrate, sodium acetate hydrate and hydrochloric acid as additives in 1 mL (i.e., a balanced salt solution containing sugar).

For comparison, (10) a balanced salt solution (BSS) was used. Viscosity was measured as to the vehicles (1) to (10) under conditions of "30° C. and velocity gradient 1/s=2" using a viscometer. The results are shown in Table 12.

TABLE 12

| Vehicle | Viscosity mPa · s | Sodium hyaluronate concentration (w/v) | Chondroitin sulfate ester sodium concentration (w/v) |
|---|---|---|---|
| (1) Viscoat | 43600 | 3.00% | 4.00% |
| (2) Viscoat diluted 2-fold | 2900 | 1.50% | 2.00% |
| (3) Viscoat diluted 4-fold | 172 | 0.75% | 1.00% |
| (4) Hyalein Mini | 37 | 0.30% | N.A. |
| (5) Provisc | 30700 | 1.00% | N.A. |
| (6) Healon | 22800 | 1.00% | N.A. |

TABLE 12-continued

| Vehicle | Viscosity mPa · s | Sodium hyaluronate concentration (w/v) | Chondroitin sulfate ester sodium concentration (w/v) |
|---|---|---|---|
| (7) Opegan | 4650 | 1.00% | N.A. |
| (8) Opegan diluted 1.5-fold | 1040 | 0.66% | N.A. |
| (9) Opegan diluted 2-fold | 564 | 0.50% | N.A. |
| (10) Balanced salt solution (BSS) | 1 | N.A. | N.A. |

N.A.: not applicable

Figure 2:
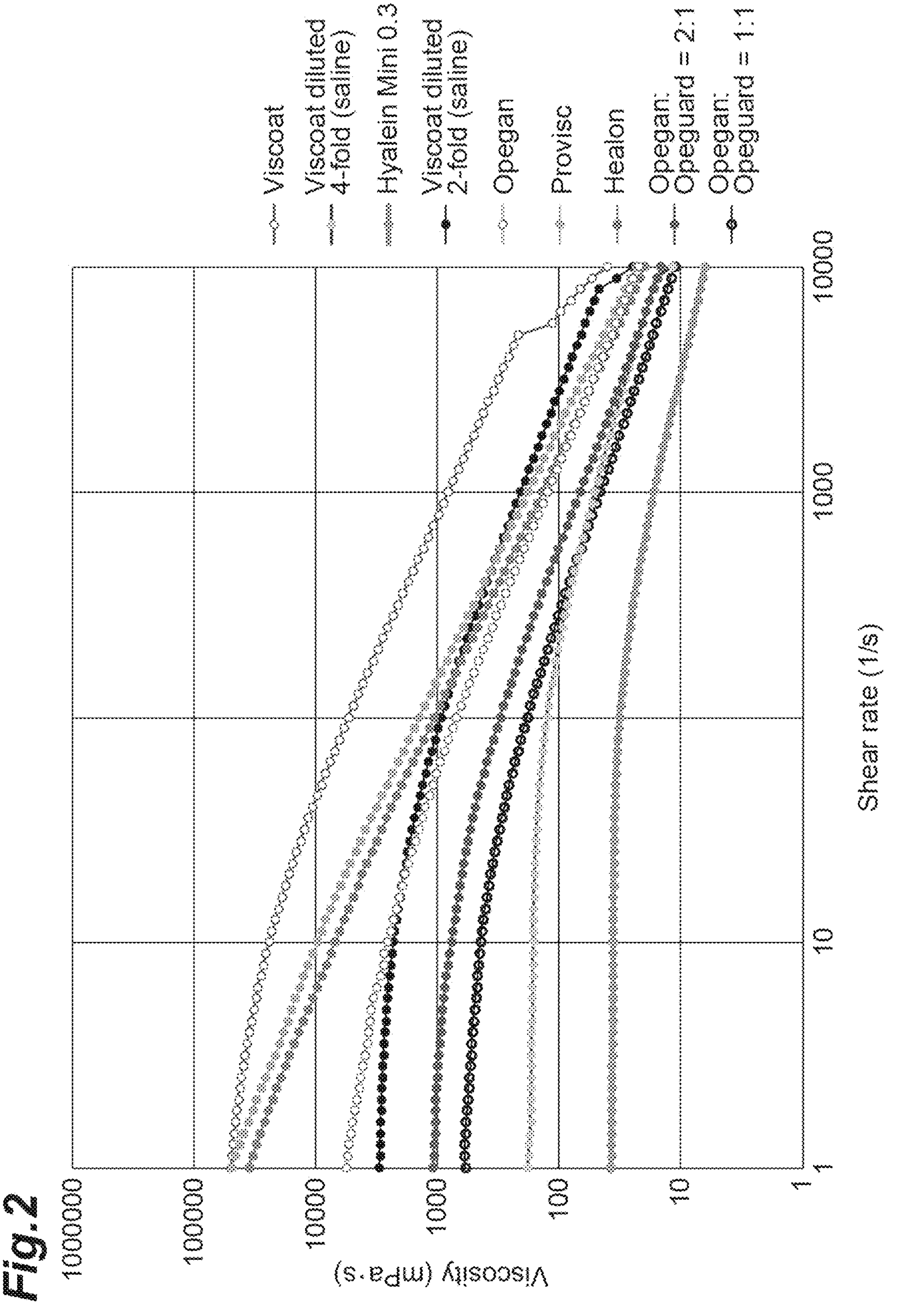
FIG. 2 is a graph showing results of measuring the correlation between velocity gradient (shear rate) and viscosity under a condition of 30° C. as to vehicles (1) to (10) shown in Table 12 in Example 1.

Also, the correlation between velocity gradient (shear rate) and viscosity was measured as to the vehicles (1) to (9) under a condition of 30° C. using a viscometer. The results are shown in FIG. 2 and Table 13.

TABLE 13

| Vehicle | Amount of change in viscosity* (mPa · s) | Viscosity at velocity gradient of 1000 (1/s) (mPa · s) |
|---|---|---|
| (1) Viscoat | 25800 | 821 |
| (2) Viscoat diluted 2-fold | 690 | 209 |
| (3) Viscoat diluted 4-fold | 18 | 51.6 |
| (4) Hyalein Mini | 1.5 | 16.8 |
| (5) Provisc | 40000 | 182 |
| (6) Healon | 28510 | 139 |
| (7) Opegan | 3090 | 125 |
| (8) Opegan diluted 1.5-fold | 314 | 68 |
| (9) Opegan diluted 2-fold | 151 | 46.4 |

*Absolute value of the amount of change in viscosity (mPa · s) from shear rates of 1 to 10

Figure 8:
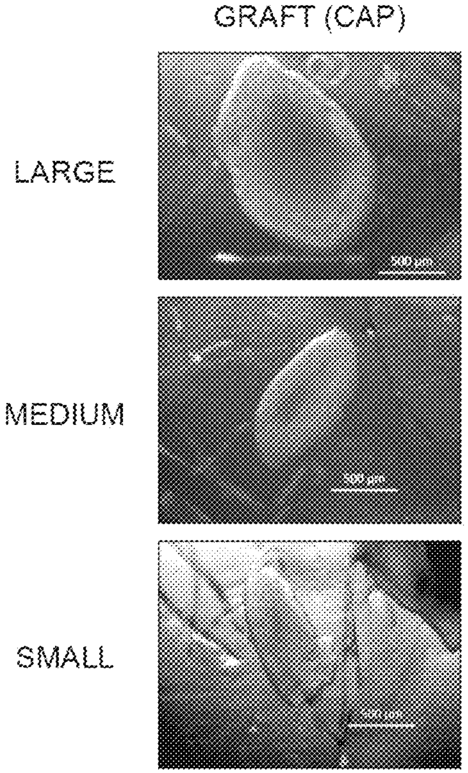
Figure 8:
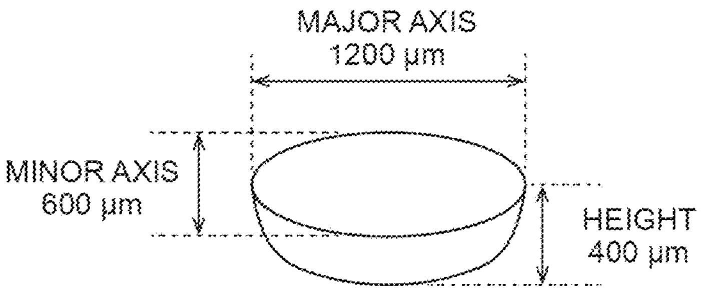

Each of the vehicles (1) to (10) was added to a retina sheet, and the behavior of the retina sheet was observed by performing suction and ejection using a plastic tip (tip for transplantation, manufactured by Bethel Co., Ltd.; which is a tip for transplantation, wherein the retina sheet illustrated in FIG. 8 can pass though the inside of the tip and the length of the tip is 1 cm or more and 10 cm or less). As a result, since (1), (5), (6), and (7) had too high viscoelasticity, the retina sheet was immediately broken into pieces in an attempt to move it in the vehicle, and repetitive sliding was found impossible. For (2) Viscoat diluted 2-fold (2900 mPa·s), it was found that although the retina sheet was slidable, the retina sheet was difficult to move in the liquid and was fragile so as to be broken. For (3) Viscoat diluted 4-fold, (8) Opegan diluted 1.5-fold, (9) Opegan diluted 2-fold, and (4) Hyalein Mini (37 mPa·s), the retina sheet slid favorably. On the other hand, in the case of using (10) a balanced salt solution having lower viscosity, vigorous discharge was found. It was found that when viscosity is low, transplantation is difficult.

Similar results are also obtained when a commercially available tip for transplantation other than the plastic tip described above is used.

In short, it was found that: a vehicle with adjusted viscosity is important as a vehicle for transplantation of a retina sheet; and favorable results are given when viscosity at a shear rate of 2 (1/s) is 2 mPa·s or more and 1040 mPa·s or less.

As shown in FIG. 2, when the "velocity gradient" (shear rate) shown in the X-axis was changed, the "viscosity" shown in the Y-axis was changed. It was able to be confirmed that the correlation therebetween differs depending on each administered vehicle. Accordingly, it was thought that in optimizing the vehicle for transplantation, a better vehicle for transplantation could be characterized by evaluating the relationship between the "velocity gradient" and the "viscosity".

From the results of FIG. 2 and Table 13, it was found that when the shear rate is small, for example, 10 (1/s) or less, a smaller rate of change in viscosity is more preferable. It was also found that the amount of change in viscosity from shear rates of 1 to 10 (1/s) (i.e., the viscosity difference between viscosity at a shear rate of 1 (1/s) and viscosity at a shear rate of 10 (1/s)) is 500 mPa·s or less (314 mPa·s in (8) of Table 12).

It was also found that viscosity at a shear rate of 1000 (1/s) is 100 mPa·s or less (68 mPa·s in (8) of Table 12).

Figure 3:
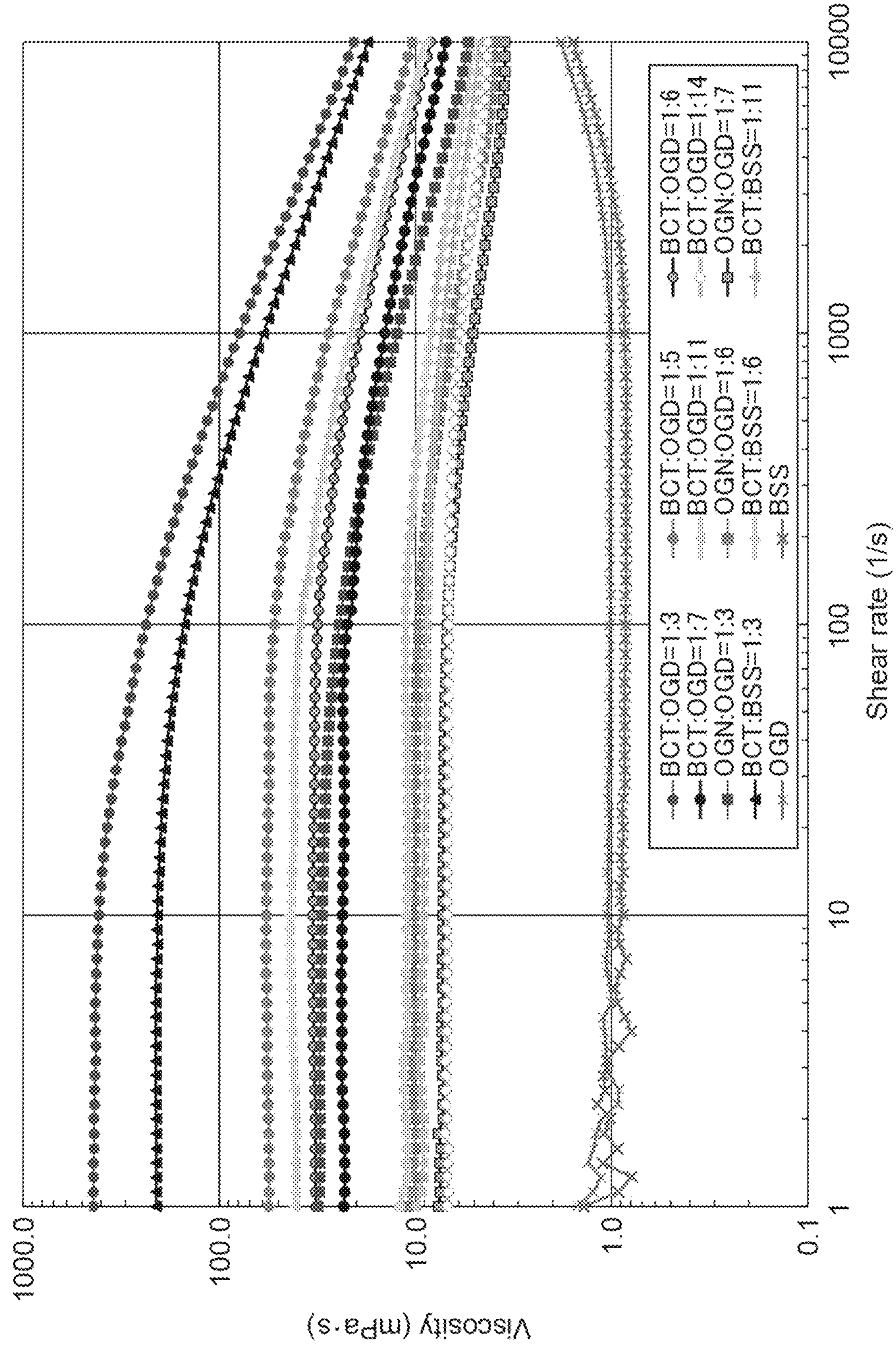
FIG. 3 is a graph showing results of measuring the correlation between velocity gradient (shear rate) and viscosity under a condition of 25° C. as to vehicles shown in Table 13 in Example 1.

In order to find the optimum viscosity, an additional study was further conducted. Viscosity measured under conditions of "25° C. and velocity gradient 1/s=2" using the aqueous hyaluronic acid solutions shown in Table 14 below is shown in Table 14. Further, results of measuring the correlation between velocity gradient and viscosity at 25° C. are shown in FIG. 3 and Table 14.

TABLE 14

| Vehicle | Dilution ratio | Viscosity (mPa · s) | Amount of change in viscosity* (mPa · s) | Viscosity at velocity gradient of 1000 (1/s) (mPa · s) |
|---|---|---|---|---|
| BCT:OGD = 1:3 | ×4 | 434.0 | 26.0 | 78.8 |
| BCT:OGD = 1:5 | ×6 | 56.0 | 1.6 | 27.6 |
| BCT:OGD = 1:6 | ×7 | 32.3 | 1.2 | 19.1 |
| BCT:OGD = 1:7 | ×8 | 23.2 | 0.3 | 14.3 |
| BCT:OGD = 1:11 | ×12 | 11.2 | 0.9 | 8.4 |
| BCT:OGD = 1:14 | ×15 | 6.9 | 0.0 | 5.9 |
| Opegan:OGD = 1:3 | ×4 | 30.5 | 1.5 | 12.4 |
| Opegan:OGD = 1:6 | ×7 | 10.0 | 0.7 | 6.5 |
| Opegan:OGD = 1:7 | ×8 | 7.2 | 0.4 | 5.1 |
| BCT:BSS+ = 1:3 | ×4 | 209.0 | 2.0 | 59.6 |
| BCT:BSS+ = 1:6 | ×7 | 40.9 | 2.3 | 21.4 |
| BCT:BSS+ = 1:11 | ×12 | 9.1 | 0.8 | 7.4 |
| OGD | N.A. | 1.1 | 0.4 | 1.0 |
| BSS+ | N.A. | 1.0 | 0.5 | 0.9 |

BCT: Viscoat;
OGD: Opeguard;
N.A.: not applicable (i.e., not diluted);
BSS+: buffer (manufactured by Alcon Inc.) in which oxyglutathione was added to a buffer (BSS)
*Absolute value of the amount of change in viscosity (mPa · s) from shear rates of 1 to 10

Each of the vehicles described above was added to a retina sheet, and the behavior of the retina sheet, i.e., whether to slide smoothly, was observed by performing suction and ejection using a plastic tip (tip for transplantation, manufactured by Bethel Co., Ltd.). As a result, for all the vehicles except for Opeguard and BSS+, the retina sheet slid favorably. In short, as the viscosity of the vehicle for transplantation at a shear rate of 2 (1/s) at 25° C., 5 to 500 mPa·s was found appropriate.

On the basis of the results of FIG. 3, the correlation between velocity gradient and viscosity at 25° C. of the vehicle for transplantation was studied.

As a result, as for the physical properties of the vehicle, it was found that favorable results are shown in a viscosity (mPa·s) range of 6.9 to 434.0 when the velocity gradient (1/s) is 2, in a viscosity (mPa·s) range of 6.9 to 410.0 when the velocity gradient (1/s) is 10, in a viscosity (mPa·s) range of 6.8 to 236.0 when the velocity gradient (1/s) is 100, in a viscosity (mPa·s) range of 5.9 to 78.8 when the velocity gradient (1/s) is 1000, and in a viscosity (mPa·s) range of 4.3 to 20.6 when the velocity gradient (1/s) 10000.

These results were also consistent with the results of FIG. 2. In short, it was found that: when the shear rate is small, for example, 10 (1/s) or less, a smaller rate of change in viscosity is more preferable; and, for example, the rate of change in viscosity from shear rates of 1 to 10 (1/s) (i.e., percentage when the viscosity difference between viscosity at a shear rate of 1 (1/s) and viscosity at a shear rate of 10 (1/s) is divided by viscosity at a shear rate of 1(1/s)) is about 10% or less, and the amount of change in viscosity is 30 mPa·s or less (26 mPa·s as to BCT:OGD=1:3 in Table 14).

It was also found that viscosity at a shear rate of 1000 (1/s) is 100 mPa·s or less.

Example 2: Study on Viscosity of Composition for Transplantation in Subretinal Administration to Rat A study on the viscosity of a composition for transplantation in subretinal administration to a rat was conducted. The method for transplantation to a rat was performed by the method described in Shirai et al., Proc Natl Acad Sci USA 2016, 113: E81-90.

On the basis of the results of Example 1, transplantation was performed under two conditions:

Viscoat diluted 2-fold (Viscoat:Opeguard=1:1), and

Viscoat diluted 4-fold (Viscoat:Opeguard=1:3).

As a result, for Viscoat diluted 4-fold, it was found that subretinal transplantation can be stably performed. In actuality, transplantation was performed to 20 nude rats under this condition, and successful transplantation was made in 18 rats. On the other hand, for Viscoat diluted 2-fold, it was found that although transplantation itself is possible, viscosity is high and slightly hinders transplantation.

As a result of pathologically analyzing 6 months later the eyeballs of the rats that underwent transplantation with Viscoat diluted 4-fold, findings about any safety problem were not observed, and it was found that a retina sheet was successfully engrafted. It was able to be demonstrated that Viscoat diluted 4-fold does not inhibit the engraftment of a retina sheet.

In short, it was able to be demonstrated that viscoelastic substances (hyaluronic acid, etc.) contained in Viscoat diluted 4-fold are free from concern about safety and the engraftment of a retina sheet, even if subretinally administered at this concentration or volume. In other words, it was able to be concerned that there is no concern about safety and graft survival as long as the concentration or the amount is equal to or less than that of Viscoat diluted 4-fold.

From the results described above, the vehicle of Viscoat diluted 4-fold was found excellent in safety and functionality and also suitable for transplantation procedures.

Example 3: Study on Viscosity of Composition for Transplantation in Subretinal Administration to Monkey A study on the viscosity of a composition for transplantation in subretinal administration to a monkey was conducted using cynomolgus monkeys. Transplantation was performed by the method described in Example 1. For the transplantation, a skilled surgeon, i.e., a clinical surgeon having 10-year or more experience of ophthalmic surgery, evaluated procedural usability.

As administered vehicles, the following vehicles were used on the basis of the results of Example 1.

Viscoat diluted 2-fold (Viscoat:Opeguard=1:1), viscosity (30° C., velocity gradient 1/s=2): 2900 mPa·s Viscoat diluted 4-fold (Viscoat:Opeguard=1:3), viscosity (25° C., velocity gradient 1/s=2): 434 mPa·s Viscoat diluted 6-fold (Viscoat:Opeguard=1:5), viscosity (25° C., velocity gradient 1/s=2): 56 mPa·s Viscoat diluted 7-fold (Viscoat:Opeguard=1:6), viscosity (25° C., velocity gradient 1/s=2): 32.3 mPa·s Hyalein Mini, viscosity (30° C., velocity gradient 1/s=2): 37 mPa·s As in Example 2, there were evaluation results indicating that Viscoat diluted 2-fold had high viscosity and was difficult to use in the transplantation method described in Example 1. Specifically, in a procedure of aspirating a retina sheet and discharging it at an appropriate position, transplant slidability was not favorable, and a little better slidability was evaluated as leading to easier transplantation. As for Viscoat diluted 4-fold, albeit better than Viscoat diluted 2-fold, improvement in slidability was also evaluated as being necessary.

On the other hand, transplantation to monkeys was carried out using Hyalein Mini, Viscoat diluted 6-fold and Viscoat diluted 7-fold, and the transplantation was also found successful without problems about the technique of the evaluator. Particularly, for Viscoat diluted 6-fold, transplantation was performed to two monkeys, and successful transplantation was able to be confirmed.

Specifically, it was found that a retina sheet can be subretinally administered slowly to a monkey and movement in bleb is also gentle, leading to easy transplantation.

Example 4: Study on Viscosity of Composition for Transplantation in Subretinal Administration Using Harvested Pig Eye A study on a composition for transplantation in subretinal administration was conducted using harvested pig eyes. Surgery was performed by the method described in Example 1. As the composition for transplantation, Viscoat diluted 7-fold (Viscoat:Opeguard=1:6, viscosity (30° C., velocity gradient 1/s=2): 32.3 mPa·s) was used.

First, from Example 1, for example, in the case of using a diluted vehicle of Viscoat, a dilution ratio on the order of 4-fold to 14-fold, preferably a dilution ratio of 5-fold to 11-fold, was found suitable. In short, it was found that: viscosity (25° C., velocity gradient 1/s=2) of 7 mPa·s to 434 mPa·s, preferably 11 to 200 mPa·s, gives favorable results; and subretinal transplantation to a pig eye can be performed without problems using Viscoat diluted 7-fold.

Various studies were conducted as mentioned above, and Viscoat was found preferable as a viscoelastic substance. This was considered to be associated not only with viscosity but also with the physical properties (stickiness and the degree of stringiness) of Viscoat. As an approach of physicochemically analyzing the physical properties, it was considered that the correlation between velocity gradient and viscosity influenced the behavior of a retina sheet in bleb. Specifically, as considered in Example 2, viscosity when a velocity gradient (1/S) at 25° C. is 2 is appropriately 5 to 500 mPa·s. Also, change in viscosity from velocity gradients of 1 to 10 is 500 or less, preferably 30 or less, further preferably 2 or less, and viscosity at a velocity gradient of 1000 is 100 or less, further preferably 30 or less.

In the present invention, a vehicle for transplantation for cells or tissue in a totally new dosage form, i.e., a retina sheet, was studied. A technique of subretinally transplanting a three-dimensional tissue such as a retina sheet, not a two-dimensional tissue, to a human stably has not been established. According to the present invention, the physical properties of the vehicle for transplantation suitable for a retina sheet has been revealed.

Reference Example 1 Production of Retina Sheet Containing Neural Retina

Human iPS cells (DSP-SQ strain, established by Sumitomo Dainippon Pharma Co., Ltd.) were subjected to feeder-free culture in accordance with the method described in Scientific Reports, 4, 3594 (2014). As a feeder-free medium, StemFit medium (AK03N, manufactured by Ajinomoto Co., Inc.) was used, and as a feeder-free scaffold, Laminin511-E8 (manufactured by Nippi, Inc.) was used.

Operation of differentiation was carried out as follows: Human iPS cells (DSP-SQ strain) were cultured in feeder-free using StemFit medium until 2 days before the cells reached sub-confluency (state where about 30% of the culture area is covered by cells). The human iPS cells the 2 days before the sub-confluency were subjected to feeder-free culture for 2 days (preconditioning treatment) in the presence of SAG (300 nM).

The preconditioned human iPS cells were treated for cell dispersions using TrypLE Select (manufactured by Life Technologies) and further separated into single cells by pipetting. Thereafter, the separated human iPS single cells were suspended in 100 µl of a serum-free medium such that the density of cells per well of a non-cell adhesive 96-well culture plate (PrimeSurface, 96 V-bottom plate, manufactured by Sumitomo Bakelite Co., Ltd.) was $1.3\times10^4$ cells, and subjected to suspension culture in the conditions of 37° C. and 5% $CO_2$. The serum-free medium (gfCDM+KSR) used herein is a serum-free medium prepared by adding 10% KSR and 450 µM 1-monothioglycerol and 1×Chemically defined lipid concentrate to a mixture of culture fluids containing F-12 medium and IMDM medium in a ratio of 1:1. At the initiation time of the suspension culture (Day 0 from initiation of the suspension culture), Y-27632 (final concentration 20 µM) and SAG (final concentration 10 nM) were added to the serum-free medium. Day 2 from initiation of the suspension culture, 50 µl of a fresh serum-free medium (the same one as mentioned above), which did not contain Y-27632 or SAG and contained human recombinant BMP4 (manufactured by R&D), was added such that the final concentration of exogenous human recombinant BMP4 became 1.5 nM (55 ng/ml).

Four days later (that is, Day 6 from initiation of the suspension culture), the medium was exchanged with the serum free medium, which did not contain Y-27632, SAG or human recombinant BMP4. Operation of medium exchange was carried out as follows: 60 µl of the medium in the incubator was discarded, 90 µl of a fresh serum-free medium (the same one as mentioned above) was added. This operation was carried out to control the total medium volume to be 180 µl. Thereafter, a half of the medium was exchanged with serum-free medium, which did not contain Y-27632, SAG or human recombinant BMP4, once every 2 to 4 days. The operation for exchanging a half volume of the medium was as follows. A half volume, i.e., 90 µl, of the medium in the incubator was discarded, 90 µl of a fresh serum-free medium (the same one as mentioned above) was added to control the total medium volume to be 180 µl.

The cell mass obtained on Day 13 from initiation of the suspension culture was cultured in a serum free medium (prepared by adding 1% $N_2$ supplement to DMEM/F12 medium) containing CHIR99021 (3 µM) and SU5402 (5 µM), for 3 days, i.e., up to Day 16 from initiation of the suspension culture.

The resultant cell aggregate on Day 16 from initiation of the suspension culture was cultured in each of the serum media shown in the following [1], [2] and [3] in the condition of 5% $CO_2$ up to Day 75 from initiation of the suspension culture.

[1] Day 16 to day 40 from initiation of the suspension culture:

DMEM/F12 medium containing 10% fetal bovine serum, 1% $N_2$ supplement and 100 µM taurine (hereinafter referred to as medium A).

[2] Day 40 to day 60 from initiation of the suspension culture:

Mixture of culture fluids containing medium A and a medium, which was Neurobasal medium containing 10% fetal bovine serum, 2% B27 supplement, 2 mM glutamine, 60 nM T3 and 100 µM taurine (hereinafter referred to as medium B) in a ratio of 1:3.

[3] On and after Day 60 from initiation of the suspension culture: medium B.

The cell mass on Day 75 from initiation of the suspension culture was observed under an inverted microscope to confirm morphology. It was found here that a neuroepithelial structure was formed.

Figure 4:
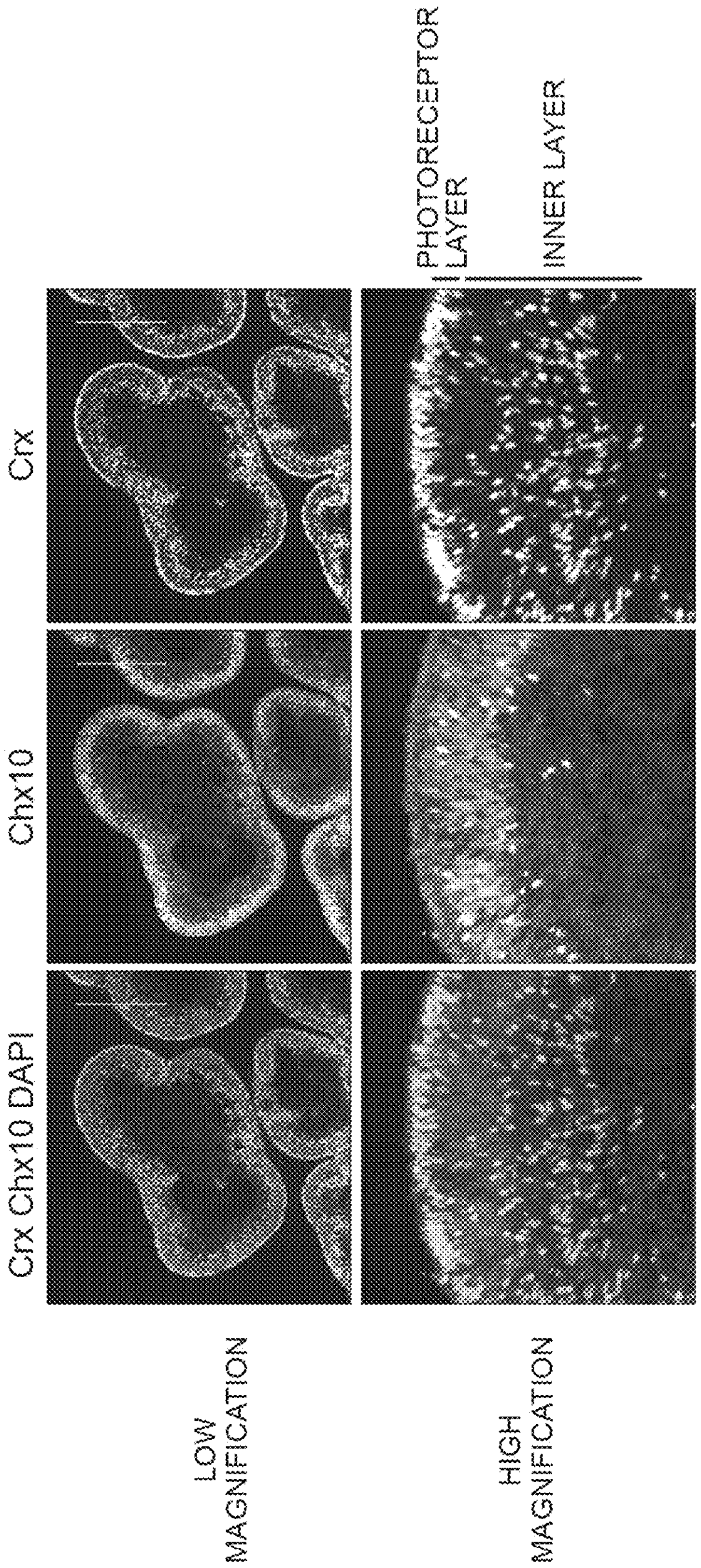
FIG. 4 is fluorescence microscope images showing results of performing immunostaining on cell aggregates containing a transplant neural retina with Crx and Chx10 in Reference Example 1.
Figure 5:
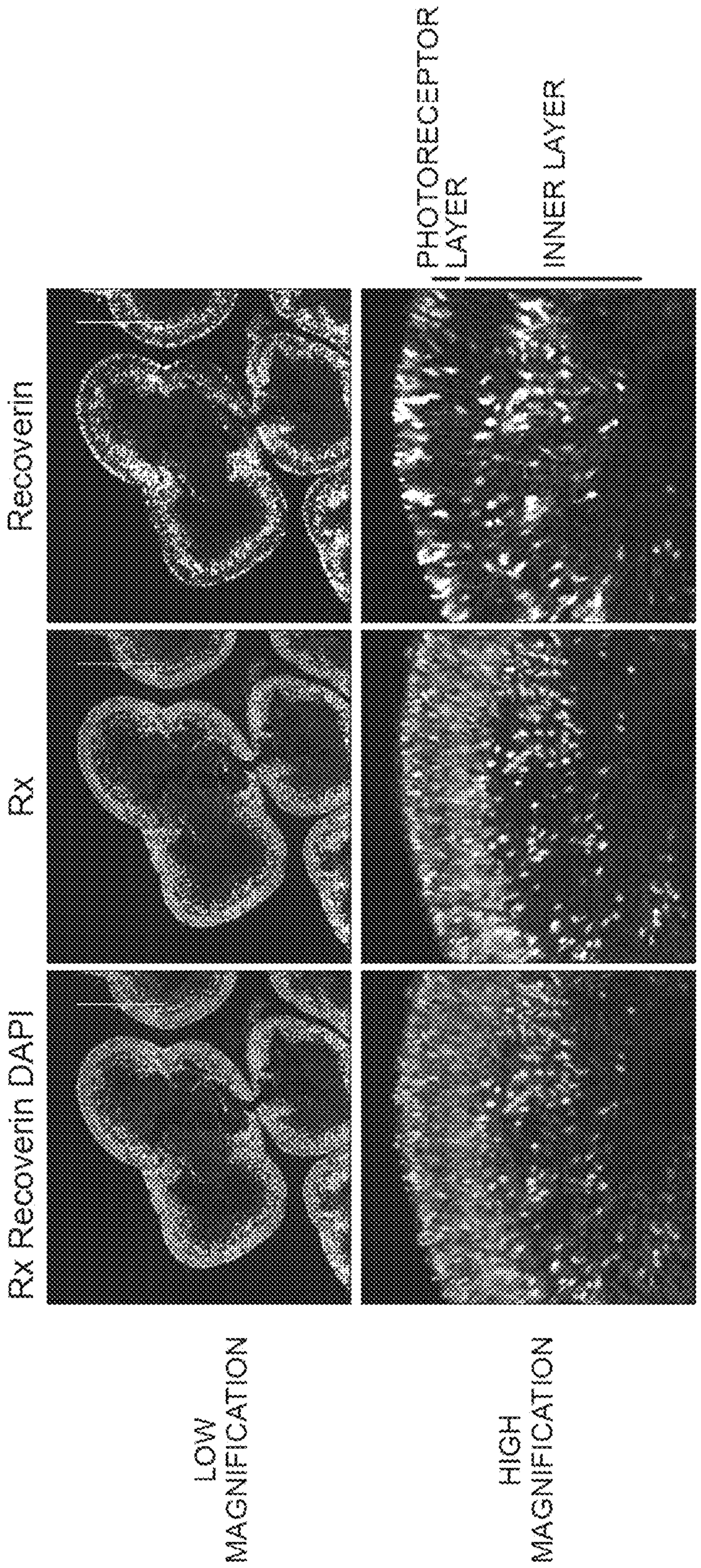
FIG. 5 is fluorescence microscope images showing results of performing immunostaining on cell aggregates containing a transplant neural retina with Rx and Recoverin in Reference Example 1.

The cell mass on Day 75 from initiation of the suspension culture was fixed with 4% paraformaldehyde, frozen and sectioned. The frozen sections were subjected to immunostaining to stain a neural retina marker, Chx10 (anti-Chx10 antibody, Exalpha Biologicals, sheep) and a photoreceptor progenitor cell marker Crx (anti-Crx antibody, Takara Bio Inc., rabbit) (FIG. 4). Other frozen sections were subjected to immunostaining to stain a neural retina marker Rx (anti-Rx antibody, Takara Bio Inc., guinea pig) and a photoreceptor cell marker recoverin (anti-recoverin antibody, Proteintech Group, rabbit) (FIG. 5). The nuclei of the cells were stained with DAPI.

These sections stained were observed using a fluorescence microscope (manufactured by Keyence Corp.) to obtain immunostained images. The photographs in which the produced cells were observed under a fluorescence microscope are shown in FIG. 4 and FIG. 5. The upper boxes of FIG. 4 and FIG. 5 are images taken with a low-magnification lens, and the lower boxes are images taken with a high-magnification lens.

From the DAPI-stained images of FIG. 4 and FIG. 5, it was found that neural tissue densely packed with cells was formed on the surface of the cell mass and this neural tissue formed a continuous epithelium structure. As a result of analyzing the image of FIG. 4, it was found that in this neural tissue, a Crx-positive layer (photoreceptor layer) with a thickness on the order of 2 to 5 cells was formed on the surface of the cell mass, a Chx10-positive layer with a thickness on the order of 5 to 20 cells was formed inside the Crx-positive layer, and a layer in which Crx-positive cells were sparsely present was further formed inside it (FIG. 4). It was found that the surface of this cell mass was morphologically an apical surface. Furthermore, as a result of analyzing the image of FIG. 5, it was found that in this neural tissue, a recoverin-positive layer (photoreceptor layer) was formed and a Rx-positive layer was also formed. From these results, it was found that in this neural tissue, a photoreceptor layer containing Crx-positive cells and recoverin-positive cells was formed on the surface, a retinal progenitor cell layer containing Chx10-positive cells was formed inside the photoreceptor layer, and a cell layer was also formed inside the retinal progenitor cell. In short, it was found that by this production method, a neural retina containing a photoreceptor layer and a retinal progenitor cell layer can be prepared from human iPS cells and this neural retina has a continuous epithelium structure.

Reference Example 2 Preparation and Evaluation of Graft

A three-dimensional retina prepared from human iPS cells consists of a neural retina having a neuroepithelial structure with the continuity of the composition or distribution of cells. This neural retina having the neuroepithelial structure has a layer structure constituted by a photoreceptor layer and an inner layer and has a characteristic appearance and morphology (FIG. 4).

Individual human three-dimensional retinas differ in shape with a size on the order of 1 to 2 mm. Although a neural retina that is used in transplantation is a main product owing to the characteristics of a production method using self-organization culture, eyeball-related tissue (RPE, ciliary body, etc.) and brain and spinal cord tissue (telencephalon, spinal cord, etc.) which are non-neural retinas are produced as by-products. Therefore, the central part of a neural retina that did not contain a non-neural retina was dissected to obtain a retina piece (graft, cap) (FIG. 6 and FIG. 7). Specifically, a neighboring part of the retina piece (Cap) was used as a sample for quality evaluation (Ring), and only a Cap corresponding to a Ring adapted for references was used as a transplant neural retina by conducting analysis (preferably, quantitative PCR).

FIG. 6 and FIG. 7 are conceptual views of typical cell aggregates. A site at which the neuroepithelial structure (preferably continuous epithelium structure) intrinsic to the neural retina where a photoreceptor layer and an inner layer appeared to be divided as two layers was found, was regarded as a graft (cap). A site that is a neighboring site of the Cap and exhibits a neuroepithelial structure (preferably continuous epithelium structure) similar to that of the Cap was regarded as a sample for quality evaluation (ring). A site other than the Cap and the Ring was referred to as a root.

An approach of isolating a Cap and a Ring from a neuroepithelial structure contained in one cell aggregate is as mentioned below.

Reference Example 3 Shape of Graft (Cap)

Grafts (caps) were prepared by the following method (FIG. 8). First, a bright-field image (phase contrast image) of a cell aggregate on Day 99 from initiation of suspension culture prepared from human iPS cells (DSP-SQ strain) in accordance with the method described in Reference Example 1 was taken under an inverted microscope (manufactured by Olympus Corp.). After confirming that a neural retina was present on the cell aggregate, the cell aggregate was transferred to under a stereo microscope, and various sizes of the neural retina were dissected as grafts by the method given below. Also, study was made on the influence of a graft size on the operation of transplantation with a device for transplantation.

(Dissection of Retina Sheet of Neural Retina)

The cell aggregate was subjected to observation by an inverted microscope (ECLIPSE Ti, manufactured by Nikon Corp.) as a bright-field image (phase contrast image). The observation was performed, particularly, focusing on features of the morphology of individual cells and the mutual adhesion state between the cells. In the cell aggregate, a site having a continuous epithelium structure where an outer neuroblastic layer (containing photoreceptor layer and neural retinal progenitor cell layer) and an inner neuroblastic layer appeared to be divided as two layers was determined as the neural retina. Also, a tissue in which a continuous epithelium structure was not found, and a site having a continuous epithelium structure where, however, an outer neuroblastic layer and an inner neuroblastic layer were not able to be distinguished from each other and appeared to be one layer, were determined as by-products. Thereafter, while observed under a stereo microscope, tissue pieces were prepared by dissecting the neural retina from the cell aggregate under the stereo microscope using tapered tweezers and scissors.

(Influence of Dissected Retina Sheet on Transplantation Operation)

A front image taken with a cut surface turned to an objective lens side, and a side image taken with the cut surface inclined so as to be perpendicular to an objective lens were taken under a stereo microscope as to the dissected grafts. Thereafter, the major axes, minor axes, and heights of the grafts were measured from the taken images. For the measurement, the major axis was defined as the longest line segment among line segments connecting two end points on the retina sheet cross section in the front image, and the length thereof. The minor axis was defined as the longest line segment among line segments connecting two end points on the retina sheet cross section in the front image and orthogonal to the major axis, and the length thereof. The height was defined as the longest line segment among line segments orthogonal to the retina sheet cross section in the side image and having a point intersecting the retina sheet cross section and the surface of the retina sheet as end points, and the length thereof. The volume of the graft was calculated according to the following calculation expression by approximating the graft as being an ellipsoid halved such that the cross section passed through the major axis.

Volume=2/3×Ratio of the circumference of a circle (π)×(Major axis/2)×(Minor axis/2)×Height As a result, it was found that the loading of a graft in a device for transplantation, the stability of the graft in the device for transplantation and the discharge of the graft from the device for transplantation were influenced by the size of the graft. It was also suggested that, particularly, the minor axis was a useful parameter. The major axis, the minor axis, the height and the volume were calculated as to each of 11 grafts for which the operation of transplantation with the device for transplantation was favorable. Results of determining an average value, the maximum value and the minimum value as to each parameter were summarized in Table 15. From this result, it was found that the graft (cap) was at least from 0.8 to 1.7 mm in major axis, from 0.4 to 1.1 mm in minor axis, from 0.2 to 0.7 mm in height, from about 0.07 to about 0.57 $mm^3$ in apparent volume.

TABLE 15

| | Major axis [mm] | Minor axis [mm] | Height [mm] | Volume [$mm^3$] |
|---|---|---|---|---|
| Average value | 1.184 | 0.646 | 0.421 | 0.184 |
| Maximum value | 1.606 | 1.051 | 0.640 | 0.565 |
| Minimum value | 0.870 | 0.462 | 0.258 | 0.070 |

Reference Example 4 Composition of Cell in Graft (Cap)

Grafts (caps) were prepared by the following method (Nos: 18001MF, d89, H5). First, grafts (caps) were isolated by the methods described in Examples 2 and 3 from a cell aggregate on Day 89 from initiation of suspension culture prepared from human iPS cells (DSP-SQ strain) in accordance with the method described in Example 1.

Figure 9:
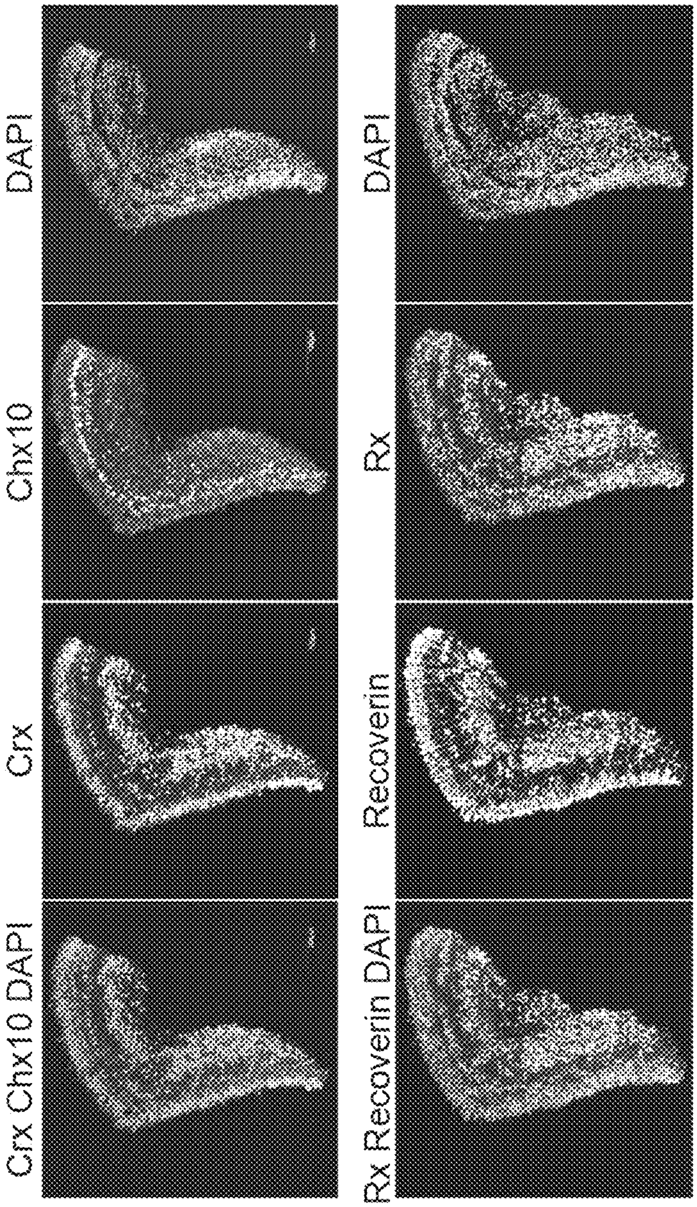
FIG. 9 is confocal fluorescence microscope images showing results of performing immunostaining on grafts with Crx, Chx10, Rx and Recoverin in Reference Example 4.

The graft was fixed with 4% paraformaldehyde, frozen and sectioned. The frozen sections were subjected to immunostaining to stain a neural retina marker, Chx10 (anti-Chx10 antibody, Exalpha Biologicals, sheep) and a photoreceptor progenitor cell marker Crx (anti-Crx antibody, Takara Bio Inc., rabbit) (FIG. 9). Other frozen sections were subjected to immunostaining to stain a neural retina marker Rx (anti-Rx antibody, Takara Bio Inc., guinea pig) and a photoreceptor cell marker recoverin (anti-recoverin antibody, Proteintech Group, rabbit) (FIG. 9). The nuclei of the cells were stained with DAPI. These sections stained were observed using a confocal laser microscope (manufactured by Olympus Corp.) to obtain immunostained images.

From the stained images, it was found that neural tissue densely packed with cells was formed on the surface (left side in the drawing) of the graft (cap) and this neural tissue formed a neuroepithelial structure (particularly, continuous epithelium structure) (FIG. 9). It was further found that in this neural tissue, a Crx-positive layer (photoreceptor layer, FIG. 9) with a thickness on the order of 2 to 10 cells was formed on the surface of the cell mass, a Chx10-positive layer with a thickness on the order of 5 to 20 cells was formed inside the Crx-positive layer, and a layer in which Crx-positive cells were present was further formed inside it (FIG. 9). It was found that the surface of this graft (cap) was morphologically an apical surface. Furthermore, it was found that in this neural tissue, a recoverin-positive layer (photoreceptor layer, FIG. 7, arrow) was formed and a Rx-positive layer was also formed. From these results, it was found that in this neural tissue, a photoreceptor layer containing Crx-positive cells and recoverin-positive cells was formed on the surface, a retinal progenitor cell layer containing Chx10-positive cells was formed inside the photoreceptor layer, and a cell layer was also formed inside the retinal progenitor cell. In short, it was found that the graft (cap) can prepare a neural retina containing a photoreceptor layer and a retinal progenitor cell layer and this neural retina has a continuous epithelium structure.

Reference Example 5 Verification of Equivalent State Between Cap and Ring

Gene expression between a Cap and a ring was compared by the method given below. First, a cell aggregate on Day 99 from initiation of suspension culture was prepared from human iPS cells (DSP-SQ strain) in accordance with the method described in Reference Example 1, and used as lot 1. Further, a cell aggregate on Day 82 from initiation of suspension culture was prepared from human iPS cells (DSP-SQ strain) in accordance with the method described in Reference Example 1, and used as lot 2. The main product neural retina and by-products were determined as to these two lots using a microscope by the methods described in Example 3 to isolate a Cap of the neural retina and caps of the by-products. Rings were isolated by dissection under a stereo microscope using tapered tweezers and scissors, as in the grafts. From the caps and the rings isolated from the neural retina and the by-products, total RNA was extracted using a spin column (manufactured by Qiagen N.V., RNeasy Micro kit) by the method described in the manual attached to the kit.

The concentration of the total RNA was measured in measurement equipment (Nanodrop, manufactured by Thermo Fisher Scientific Inc.), and then, it was reversely transcribed into cDNA using reverse transcriptase and primers (Reverse Transcription Master Mix Kit, manufactured by Fluidigm Corp.). The cDNA was subjected to multiplex-PCR reaction (Pre-Run) using all the probes used in the test and using a PCR apparatus (Veriti 96 well thermal cycler, manufactured by Applied Biosystems). Thereafter, the Pre-Run reaction solution was injected to multi-wells with flow channels (96.96 Dynamic Array IFC, manufactured by Fluidigm Corp.) using IFC Controller HX (manufactured by Fluidigm Corp.), and the expression level of marker gene in the neural retina and the by-products other than the neural retina was measured by real-time PCR using a multi-sample real-time PCR system (Biomark HD, manufactured by Fluidigm Corp.). The probes for PCR used in the test are shown in Table 16.

TABLE 16

| Classification | Gene name | Probe ID | GenBank ID |
|---|---|---|---|
| Internal standard | GAPDH | Hs02758991_g1 | NM_001256799.2, NM_001289745.2 NM_001289746.1, NM_001357943.1 NM_002046.7 |
| | ActinB | Hs01060665_g1 | NM_001101.5 |
| Neural retina | RAX | Hs00429459_m1 | NM_013435.2 |
| | Chx10 | Hs01584047_m1 | NM_182894.2 |
| | SIX3 | Hs00193667_m1 | NM_005413.4 |
| | SIX6 | Hs00201310_m1 | NM_007374.2 |
| | RCVRN | Hs00610056_m1 | NM_002903.2 |
| | CRX | Hs00230899_m1 | NM_000554.6 |
| | NRL | Hs00172997_m1 | NM_006177.4 |
| | NESTIN | Hs04187831_g1 | NM_006617.2 |
| Cerebrospinal | FOXG1 | Hs01850784_s1 | NM_005249.4 |
| | Emx2 | Hs00244574_m1 | NM_004098.4, NM_001165924.1 |
| | Nkx2.1 | Hs00968940_m1 | NM_003317.3, NM_001079668.2 |
| | Dmbx1 | Hs00542612_m1 | NM_172225.1, NM_147192.2 XM_011540668.2, XM_017000289.1 |
| | HOXB2 | Hs01911167_s1 | NM_002145.3, XM_005257275.4 |
| | HoxA5 | Hs00430330_m1 | NM_019102.4 |
| Eyeball | MITF | Hs01117294_m1 | NM_000248.3, NM_006722.2 NM_198158.2, NM_198159.2 NM_198177.2, NM_198178.2 NM_001184967.1, NM_001184968.1 NM_001354604.1, NM_001354605.1 NM_001354606.1, NM_001354607.1 NM_001354608.1 |
| | aqp1 | Hs01028916_m1 | NM_198098.3, NM_001329872.1 |
| | ZIC1 | Hs00602749_m1 | NM_003412.4 |
| | PAX2 | Hs01057416_m1 | NM_000278.4, NM_003987.4 NM_003988.4, NM_003989.4 NM_003990.4, NM_001304569.1 |

TABLE 16-continued

| Classification | Gene name | Probe ID | GenBank ID |
|---|---|---|---|
| Undifferentiated iPSC | POU5F1 | Hs00999632_g1 | NM_002701.6, NM_203289.5 NM_001173531.2, NM_001285986.1 NM_001285987.1 |
| | Nanog | Hs04260366_g1 | NM_024865.4, NM_001297698.1 |

Figure 10A:
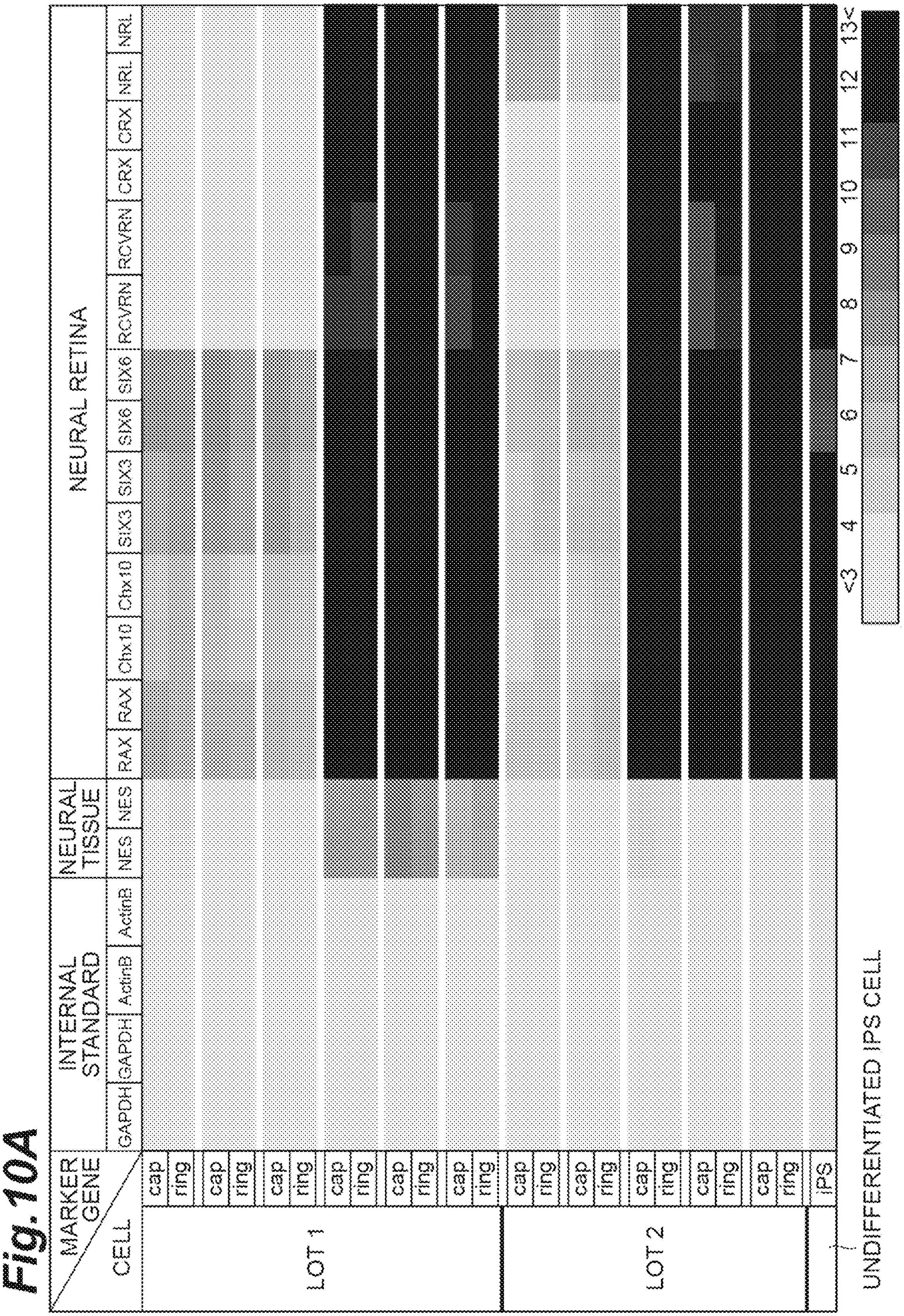
FIG. 10A shows results of analyzing gene expression for RNA extracted from a Cap and a Ring by quantitative PCR in Reference Example 5.
Figure 10B:
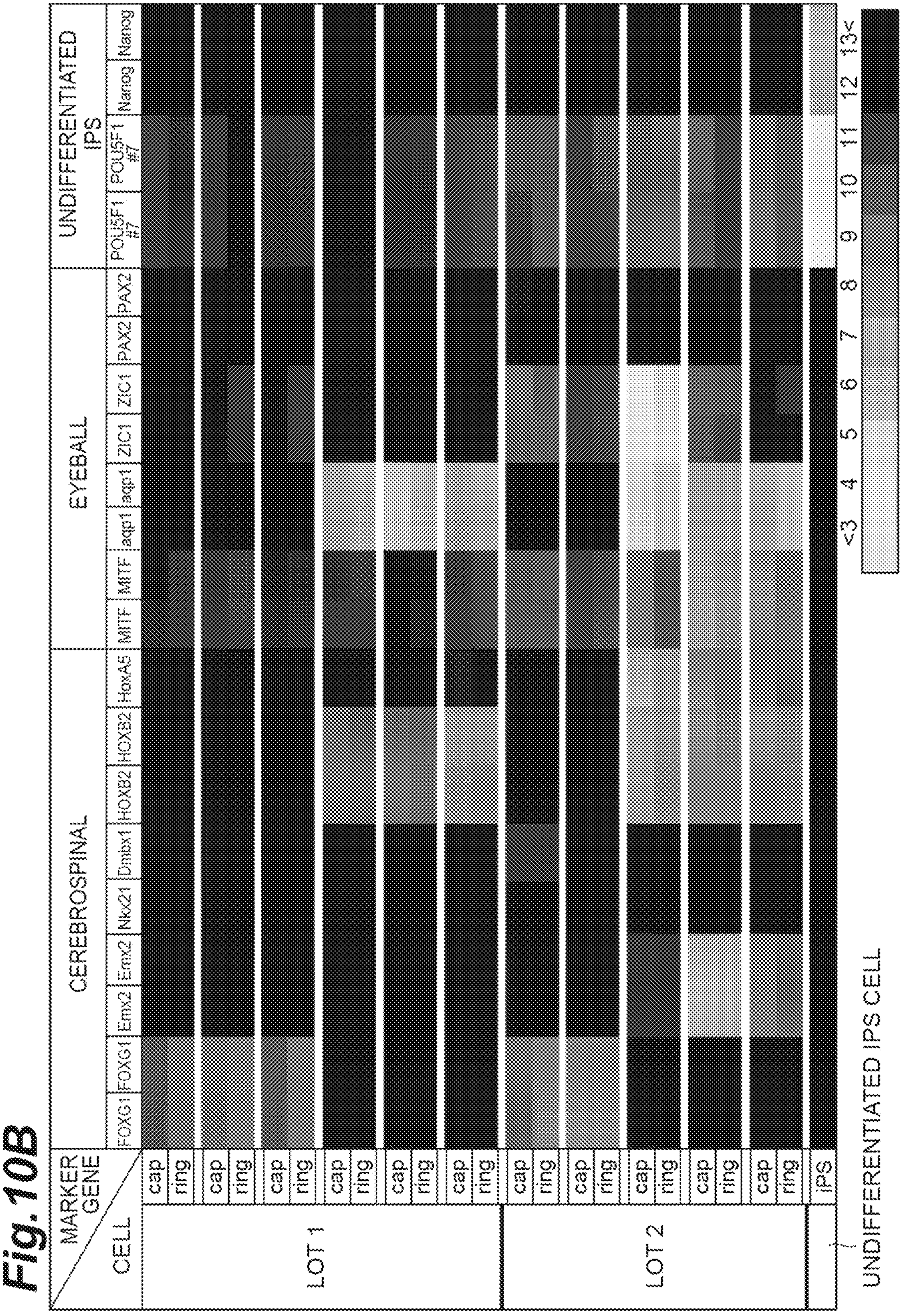
FIG. 10B shows results of analyzing gene expression for RNA extracted from a Cap and a Ring by quantitative PCR in Reference Example 5.

The results are shown in a heatmap in FIG. 10A and FIG. 10B. The gene expression levels were evaluated from ΔCt values calculated from the difference between the Ct value of the target gene and the Ct value of the GAPDH gene used as an internal standard. A lower ΔCt value represents a higher gene expression level, and a higher ΔCt value represents a lower gene expression level. The gray color corresponds to a high gene expression level, and the black color corresponds to a low gene expression level (a lighter color corresponds to a higher level of gene expression). As a result of examining gene expression in each Cap and ring, the neural retina marker gene group was expressed in the Cap and the Ring isolated from the neural retina in both the lot 1 and the lot 2. On the other hand, as a result of examining gene expression in the caps and the rings isolated from the by-products, the expression level of the neural retina marker gene group was low and the expression levels of the by-product marker gene groups were high, on the contrary to the neural retina, in both the lots. Moreover, as a result of comparing gene expression between the Cap and the Ring isolated from the same cell aggregate, it was found that the expression level of the neural retina marker gene or the expression level of the by-product marker gene was equivalent between the Cap and the Ring isolated from any of the neural retina and the by-products.

From these results, it was able to be demonstrated that, provided that the Ring is the neural retina, the Cap is also the neural retina. It was also able to be demonstrated that gene expression is equivalent between the Cap and the ring.

Reference Example 6 Transplantation Results of Graft

The gene expression of a Ring was analyzed by the method described in Reference Example 5, and then, the corresponding Cap (neural retina sheet) was used as the retina sheet described in Reference Example 1. The retina sheet was dipped in "Viscoat diluted 4-fold (Viscoat:Opeguard=1:3)" as a vehicle for transplantation to prepare a composition for transplantation. This was transplanted to a retinal degenerative nude rat to evaluate images of post-transplant engraftment.

First, a cell aggregate was prepared from human iPS cells (DSP-SQ strain) in accordance with the method described in Example 1. Thereafter, a Cap and a Ring were isolated by the method described in Reference Example 3 from the cell aggregate on Day 75 or later from initiation of suspension culture. The isolated Cap was preserved using a commercially available preservation solution while the gene analysis of the Ring was carried out. The isolated Ring was subjected to gene expression analysis by real-time PCR using Biomark HD (manufactured by Fluidigm Corp.) in accordance with the method described in Reference Example 5. From the results of the gene expression analysis, a Ring that expressed the neural retina marker gene and did not express the by-product marker gene was selected, and a Cap corresponding to this Ring was selected as a graft (retina sheet to be transplanted). The graft was washed with a buffer (manufactured by Thermo Fisher Scientific Inc.) and then dipped in the vehicle described in Example 1 to prepare a composition for transplantation. This was subretinally transplanted to a retinal degenerative nude rat (photoreceptor cell degenerative model, SD-Foxn1 Tg(S334ter)3LavRrrc nude rat) using the injector described in the known literature (Shirai et al., PNAS 113, E81-E90).

The eye tissue obtained on Days 230 to 240 from initiation of the suspension culture was fixed with paraformaldehyde (PFA fixed) and subjected to sucrose replacement. The eye tissue fixed was frozen and sectioned by use of a cryostat. These frozen sections were subjected to immunostaining to stain a human nucleus (anti-HuNu antibody, Merck Millipore, mouse, or anti-HNA antibody), a photoreceptor cell marker recoverin (anti-recoverin antibody, Proteintech Group, rabbit) and a bipolar cell marker PKCα (anti-PKCα antibody, R&D systems, Inc., goat).

Results of summarizing quality evaluation results by the gene expression analysis of rings and transplantation results of grafts are shown in Table 17. A method for calculating ΔCt values employed the method described in Reference Example 5. The gene expression analysis of rings passed them on the quality evaluation test (ring-PCR test) when the ΔCt value of a neural retina marker gene, recoverin, was or less and each of the ΔCt values of by-product marker genes FOXG1, HOXB2, ZIC1 and OCT3/4 was 5 or more. As for the transplantation results, engraftment was evaluated as being favorable when human nucleus-positive and recoverin-positive photoreceptor cells were able to be subretinally detected. It was determined that swelling was not detected unless the transplantation site was much thicker than the proper size of engraftment.

Figure 11:
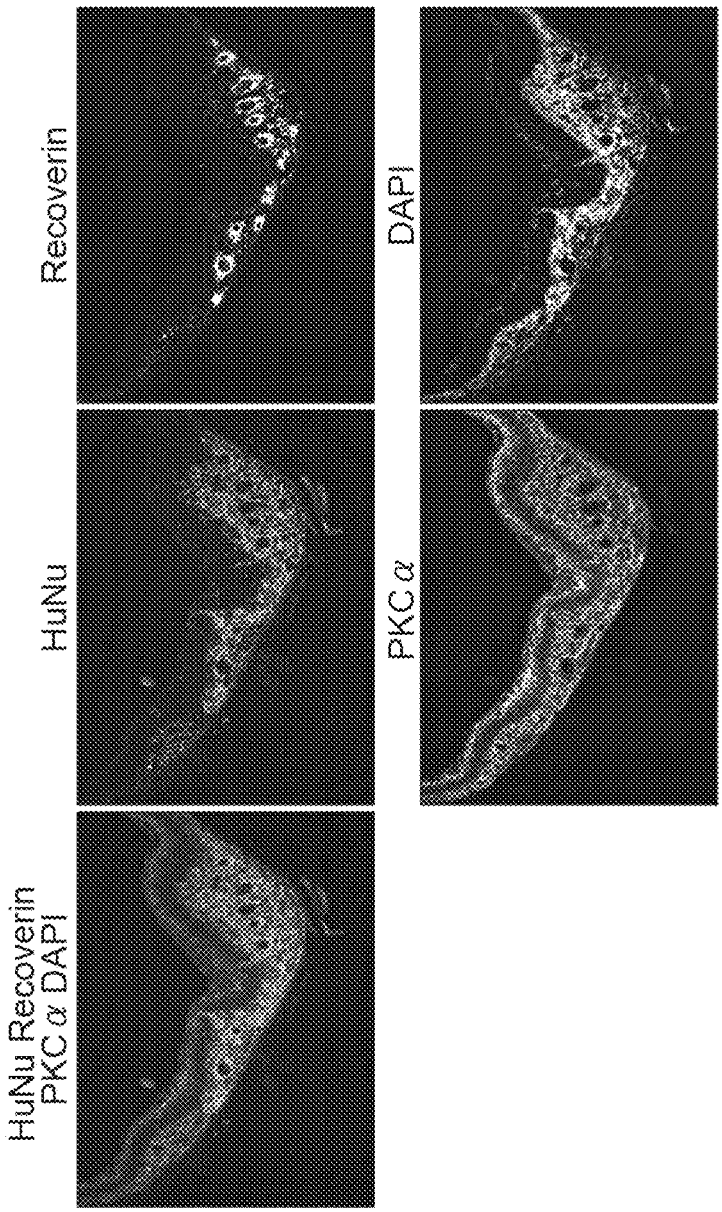
FIG. 11 is images showing results of analyzing RNA extracted from a Ring by quantitative PCR, then subretinally transplanting a graft (cap) to a rat, and observing an image of post-transplant engraftment under a fluorescence microscope in Reference Example 6.

A typical image of engraftment is shown in FIG. 11. As a result of evaluating images of post-transplant engraftment as to 14 eyes passed on the quality evaluation test before transplantation, recoverin-positive photoreceptor cells were detected in all the 14 eyes. Thus, favorable engraftment was found. Since these cells were HuNu-positive, it was found that the recoverin-positive photoreceptor cells were derived from the transplanted caps. Swelling was not detected in any of the 14 eyes.

From the results described above, a graft that was subretinally favorably engrafted, i.e., in which photoreceptor cells were engrafted without causing swelling, was able to be selected by examining the expression levels of the neural retina and by-products marker genes before transplantation by the gene expression analysis of the ring.

The safety of "Viscoat diluted 4-fold (Viscoat:Opeguard=1:3)", a vehicle for transplantation, in subretinal administration was able to be demonstrated. Specifically, although hyaluronic acid and chondroitin sulfate are contained in Viscoat diluted 4-fold, the safety of a vehicle using 0.75 w/v % of hyaluronic acid and 1.00 w/v % of chondroitin sulfate in subretinal administration was able to be demonstrated.

TABLE 17

| Graft | | Transplantation results | |
|---|---|---|---|
| Strain | Quality evaluation test | Engraftment of photoreceptor cell | Swelling |
| DSP-SQ | Pass on ring-PCR test | All cases of 14 eyes Favorable engraftment | All cases of 14 eyes Not observed |

Reference Example 7 Expression of Marker in Cap and Ring

In Reference Example 5, it was demonstrated by PCR that the composition of cells was equivalent between a Cap and a Ring. Accordingly, whether the composition of cells and a tissue structure were equivalent between the Cap and the Ring was then examined by immunostaining.

First, human iPS cells (DSP-SQ strain) were differentiated into retinas by the production method described in Reference Example 1. Thereafter, a Cap and a Ring of the neural retina were isolated by the method described in Reference Example 5 from a cell aggregate on Day 120 from initiation of suspension culture. Thereafter, the Cap and the Ring were washed, then fixed with 4% paraformaldehyde (PFA fixed) and subjected to sucrose replacement. The Cap and the Ring fixed were frozen and sectioned by use of a cryostat. These frozen sections were subjected to immunostaining to stain a nucleus with DAPI, a photoreceptor progenitor cell marker Crx (anti-Crx antibody, Takara Bio Inc., rabbit), a neural retina marker Chx10 (anti-Chx10 antibody, Exalpha Biologicals, sheep), a rod photoreceptor progenitor cell marker NRL (anti-NRL antibody, Bio-Techne Corp., goat), a telencephalon marker FOXG1 (anti-FOXG1 antibody, Takara Bio Inc., rabbit), an optic stalk marker PAX2 (anti-PAX2 antibody, Thermo Fisher Scientific Inc., rabbit), and an undifferentiated pluripotent stem cell marker NANOG (anti-NANOG antibody, Merck, mouse).

Figure 12:
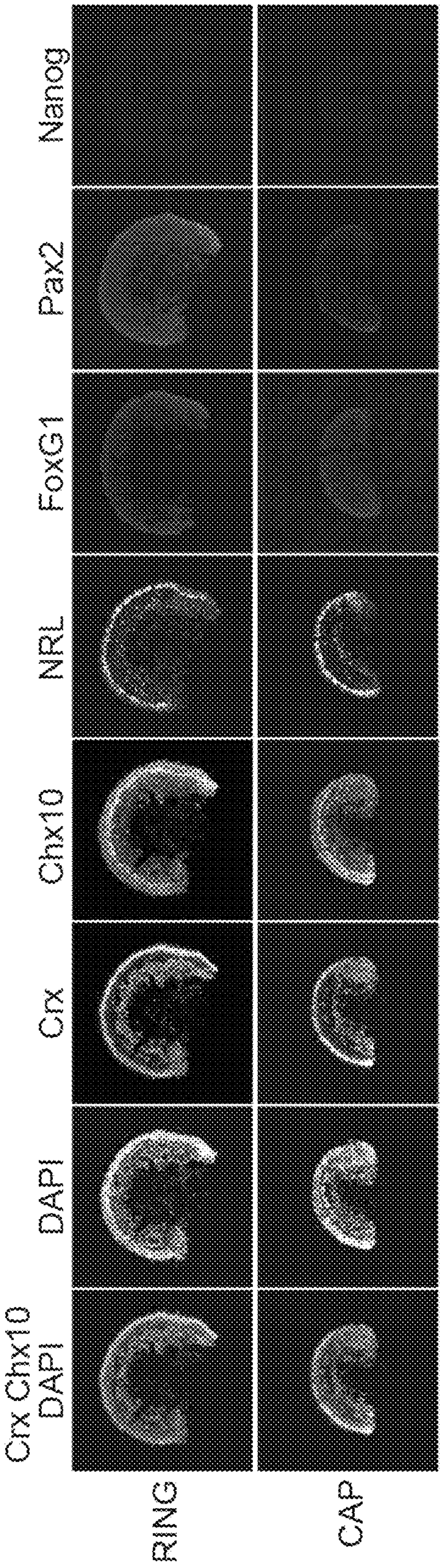
FIG. 12 is fluorescence microscope images showing results of performing immunostaining on a Cap and a Ring prepared from one cell aggregate in Reference Example 7.

The results of the immunostaining are shown in FIG. 12. As for the Cap and the Ring dissected from the same cell aggregate, the results of immunostaining the Ring are shown in the upper boxes, and the results of immunostaining the Cap are shown in the lower boxes. From these results, it was found that Crx-positive photoreceptor progenitor cells, Chx10-positive neural retina, and NRL-positive rod photoreceptor progenitor cells were expressed in a continuous layer pattern in both the Cap and the ring. FOXG1-positive telencephalon, PAX2-positive optic stalk, or NANOG-positive pluripotent stem cells were not detected in any of the Cap and the ring. When Crx-, Chx10- and NRL-stained images were compared, it was confirmed that these neural retina markers exhibited almost equivalent distribution between the Cap and the ring.

Reference Example 8 Ratios of Photoreceptor Progenitor Cell and Neural Retinal Progenitor Cell Constituting Transplant Neural Retina Sheet The ratios of photoreceptor progenitor cells and neural retinal progenitor cells to cells constituting a neural retina sheet prepared from a cell aggregate differentiated from pluripotent stem cells were analyzed and quantified by an immunostaining method, immunohistochemistry (IHC).

Human iPS cells (DSP-SQ strain) were differentiated into retinas by the production method described in Example 1. Thereafter, caps and rings were isolated by the method described in Reference Example 3 from the cell aggregates on Days 84, 92 and 93 from initiation of suspension culture. The gene expression analysis of the isolated rings was carried out by the method described in Reference Example 6. A Ring that expressed the neural retina marker gene and did not express the by-product marker gene was selected by the method described in Reference Example 6, and a Cap corresponding to this Ring was used as a transplant neural retina sheet. In this way, one transplant neural retina sheet from the cell aggregate on Day 84 from initiation of suspension culture, two transplant neural retina sheets from the cell aggregate on Day 92 from initiation of suspension culture, and one transplant neural retina sheet from the cell aggregate on Day 93 from initiation of suspension culture, were prepared. In other words, a total of four transplant neural retina sheets were prepared.

Figure 13:
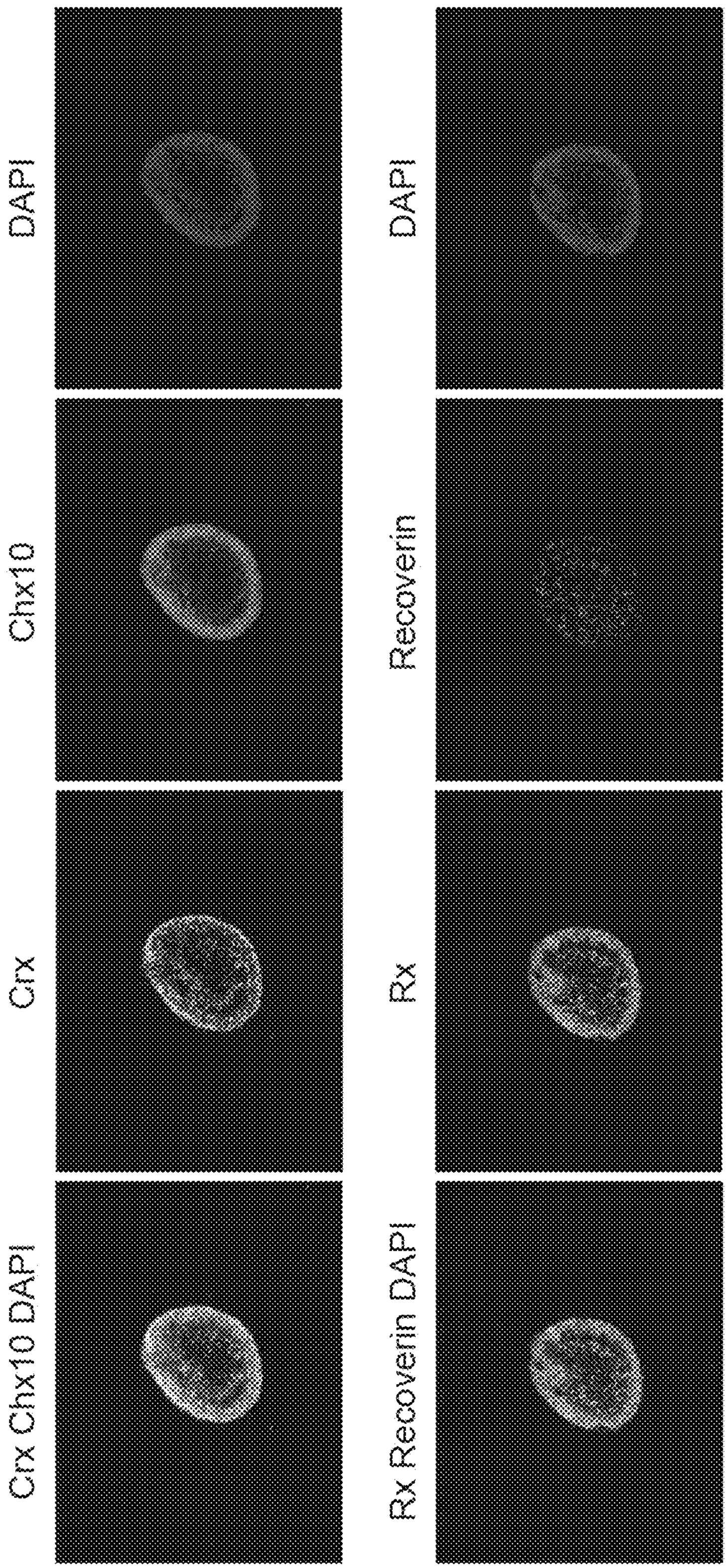
FIG. 13 is fluorescence microscope images showing results of performing immunostaining on a cap prepared from one cell aggregate in Reference Example 8.

The obtained transplant neural retina sheets were cultured for 7 days in B medium for analysis. The cultured transplant neural retina sheets were fixed with 4% paraformaldehyde, frozen and sectioned. The frozen sections were subjected to immunostaining to stain a neural retinal progenitor cell marker, Chx10 (anti-Chx10 antibody, Exalpha Biologicals, sheep) and a photoreceptor progenitor cell marker Crx (anti-Crx antibody, Takara Bio Inc., rabbit). Other frozen sections were subjected to immunostaining to stain a neural retina marker Rx (anti-Rx antibody, Takara Bio Inc., guinea pig) and a photoreceptor cell marker recoverin (anti-recoverin antibody, Proteintech Group, rabbit). The nuclei of the cells were stained with DAPI. These sections stained were observed using a fluorescence microscope (manufactured by Keyence Corp.) to obtain immunostained images. One example thereof (D3) is shown in FIG. 13.

The immunostained images were analyzed in ImageJ (version 1.52a, manufactured by National Institutes of Health (NIH)) to analyze the number of DAPI-positive cells, the number of DAPI-positive and Chx10-positive cells, and the number of DAPI-positive and Crx-positive cells as to each of the four transplant neural retina sheets. The immunostained images were analyzed in the same manner to analyze the number of DAPI-positive cells and the number of DAPI-positive and Rx-positive cells. From these numerical values, the ratio of Chx10-positive cells, the ratio of Crx-positive cells, and the ratio of Rx-positive cells were calculated. The obtained results are shown in Table 18.

TABLE 18

| Cap | The number of days from initiation of | Ratio of positive cell (%) | | |
|---|---|---|---|---|
| ID No | suspension culture (d) | Chx10 | Crx | Rx |
| B3 | 84 + 7 | 44.6 | 29.7 | 39.5 |
| D2 | 92 + 7 | 38.9 | 41.5 | 44.3 |
| D3 | 92 + 7 | 22.7 | 39.0 | 53.5 |
| G3 | 93 + 7 | 36.6 | 55.5 | 53.5 |

From the results described above, it was found that the ratio of Chx10-positive cells contained in the transplant neural retina sheet dissected from the cell aggregate was on the order of 23 to 45%, the ratio of Crx-positive cells was on the order of 30 to 56%, and the ratio of Rx-positive cells was on the order of 40 to 54%.

In short, it was suggested that about 34% (about 23 to 45%) Chx10-positive neural retinal progenitor cells, about 40% (30 to 56%) Crx-positive photoreceptor progenitor cells, and about 47% (40 to 54%) Rx-positive cells were contained in the transplant neural retina sheet.

Reference Example 9 Ratios of Photoreceptor Progenitor Cell and Neural Retinal Progenitor Cell Constituting Transplant Neural Retina Sheet The composition of cells constituting transplant neural retina sheets prepared from cell aggregates differentiated from various pluripotent stem cells was examined by an immunostaining method, flow cytometry (also referred to as FACS).

Human iPS cells (QHJI01s04 strain) were differentiated into retinas by the production method described in Reference Example 1. Thereafter, a Cap and a Ring were isolated by the method described in Reference Example 3 from the cell aggregate on Day 88 from initiation of suspension culture. The Cap was used as a transplant neural retina sheet. The transplant neural retina sheet was preserved at a low temperature of 17° C. for 2 days. Five transplant neural retina sheets obtained were combined as one sample, washed with PBS, enzymatically treated at 37° C. for 30 minutes using a neuronal cell dispersion solution (manufactured by FUJIFILM Wako Pure Chemical Corp, containing papain), and dispersed into single cells by pipetting to obtain a single-cell suspension. The obtained single-cell suspension was fixed using a fixative solution (manufactured by Becton, Dickinson and Company, CytoFix) to obtain a sample for FACS. The sample for FACS was subjected to blocking and permeation treatment (cell membrane perforation) using Perm/Wash (manufactured by Becton, Dickinson and Company) containing serum. Then, immunostaining was performed with the following antibodies fluorescently labeled: anti-Chx10 antibody (manufactured by Santa Cruz Biotechnology, Inc.), anti-Pax6 antibody (manufactured by Becton, Dickinson and Company), and anti-Crx antibody (manufactured by Santa Cruz Biotechnology, Inc.). Then, analysis was conducted by flow cytometry using an analyzer (manufactured by Becton, Dickinson and Company).

As a result, it was found that a Chx10-positive and Pax6-positive fraction (neural retinal progenitor cell fraction) occupied 11.5%, a Chx10-positive and Pax6-negative fraction (progenitor cell fraction biased toward bipolar cells) occupied 23.4%, a Chx10-negative and Pax6-positive fraction (ganglion cell and amacrine cell fraction) occupied 10.7%, and a Crx-positive cell fraction (photoreceptor progenitor cell fraction) occupied 17.4%.

Further, human iPS cells (DSP-SQ strain) were differentiated into retinas by the production method described in Reference Example 1. Thereafter, 11 cell aggregates on Day 88 from initiation of suspension culture were prepared, and 11 each of caps and rings were isolated by the method described in Reference Example 3 from each of the cell aggregates. The 11 caps were combined as one sample. Likewise, the 11 rings were combined as one sample. The Cap sample and the Ring sample were each washed with PBS and enzymatically treated at 37° C. for 30 minutes using a neuronal cell dispersion solution (manufactured by FUJIFILM Wako Pure Chemical Corp, containing papain) to obtain respective single-cell suspensions of the Cap and the ring. The obtained respective single-cell suspensions of the Cap and the Ring were fixed using a fixative solution (manufactured by Becton, Dickinson and Company, CytoFix) to obtain samples for FACS. The samples for FACS were subjected to blocking and perforation using Perm/Wash (manufactured by Becton, Dickinson and Company) containing serum and subjected to immunostaining with the following antibodies fluorescently labeled: anti-Chx10 antibody (manufactured by Santa Cruz Biotechnology, Inc.), anti-Crx antibody (manufactured by Santa Cruz Biotechnology, Inc.), and anti-SSEA-4 antibody. Isotype controls were used as negative controls for immunostaining. Then, analysis was conducted by flow cytometry using an analyzer (manufactured by Becton, Dickinson and Company). The ratio of Chx10-positive cells, the ratio of Crx-positive cells, and the ratio of SSEA-4-positive cells were calculated from delta from their respective isotype controls. The results are described in Table 19.

TABLE 19

| Sample | The number of days from initiation of suspension culture (d) | Ratio of positive cell (%) Chx10 | Crx | SSEA-4 |
|---|---|---|---|---|
| Cap | 88 | 29.4 | 15.8 | <1 |
| Ring | 88 | 28.1 | 21.7 | <1 |

In the Cap sample, the ratio of neural retinal progenitor cell marker Chx10-positive cells was 29.4%, the ratio of photoreceptor progenitor cell marker Crx-positive cells was 15.8%, and the ratio of pluripotent stem cell marker SSEA-4-positive cells (non-target cells) was less than 1%. In the Ring sample, the ratio of neural retinal progenitor cell marker Chx10-positive cells was 28.1%, the ratio of photoreceptor progenitor cell marker Crx-positive cells was 21.7%, and the ratio of pluripotent stem cell marker SSEA-4-positive cells (non-target cells) was less than 1%.

From these results, first, it was found that the Cap sample and the Ring sample were neural retinas containing Chx10-positive cells and Crx-positive cells and did not substantially contain undifferentiated iPS cells. Furthermore, it was able to be demonstrated that the ratios of Chx10-positive cells and Crx-positive cells contained in the Cap sample were equivalent to the ratios of Chx10-positive cells and Crx-positive cells contained in the Ring sample. Moreover, it was able to be demonstrated that, provided that the Ring sample was the neural retina, the Cap was also the neural retina.

Besides, it was found that, in the case of using such a Cap or a Ring (preferably cap) as a transplant neural retina sheet, the Chx10-positive fraction (neural retinal progenitor cell fraction) contained in this transplant neural retina sheet occupied about 30% (about 20 to 40%), and the Crx-positive cell fraction (photoreceptor progenitor cell fraction) occupied about 17% (about 10 to 30%).

INDUSTRIAL APPLICABILITY

The vehicle of the present invention and the composition for transplantation comprising a retinal tissue and the vehicle are very useful in the subretinal transplantation of a retinal tissue for the treatment of retinal degenerative diseases such as retinitis pigmentosa (RP).

The invention claimed is:

1. A method for treating a disease caused by the damage of a neural retina or the injury of a neural retina in a subject in need thereof, comprising subretinally transplanting, to the subject, a transplant retinal tissue and a vehicle, wherein the transplant retinal tissue comprises a neural retina sheet, the vehicle has a viscosity of 5 to 500 mPa·s at a shear rate of 2 (1/s) at 25° C. and comprises hyaluronic acid and a pharmaceutically acceptable aqueous liquid, the neural retina sheet (1) being derived from a cell aggregate obtained by a floating culturing of pluripotent stem cells, (2) having a three-dimensional structure which does not contain retinal pigment epithelial cells, (3) comprising a neural retina layer having a plurality of layer structures including a photoreceptor layer and an inner layer, (4) the photoreceptor layer comprising one or more cells selected from the group consisting of a photoreceptor progenitor cell and a photoreceptor cell, (5) the inner layer comprising one or more cells selected from the group consisting of a retinal progenitor cell, a ganglion cell, an amacrine cell and a bipolar cell, (6) the surface of the neural retinal layer having an apical surface, (7) the inner layer being present inside the photoreceptor layer present along the apical surface, (8) the area of the apical surface of the neural retinal layer being 50% or more with respect to the total area of the surface of the neural retina sheet, (9) the area of a continuous epithelium structure being 80% or more with respect to the total area of the apical surface of the neural retinal layer, and

(10) the expression of neural retina-related gene being found and the expression of non-neural retina-related cell-related gene being not found in the transplant neural retina sheet, wherein the non-neural retina-related cell-related gene comprising one of more brain and spinal cord tissue marker gene and one or more eyeball-related tissue maker gene, and the eyeball-related tissue marker gene at least comprises retinal pigment epithelium marker gene.

2. The method according to claim 1, wherein for the vehicle, the viscosity at a shear rate of 2 (1/s) at 25° C. is from 10 to 100 mPa·s.

3. The method according to claim 1, wherein for the vehicle, a viscosity at a shear rate of 1000 (1/s) at 25° C. is 100 mPa·s or less, and a viscosity difference between viscosity at a shear rate of 1 (1/s) and viscosity at a shear rate of 10 (1/s) is 100 mPa·s or less.

4. The method according to claim 1, wherein pH of the vehicle is from 7.0 to 7.5.

5. The method according to claim 1, wherein the pharmaceutically acceptable aqueous liquid is a balanced salt solution.

6. The method according to claim 1, wherein the vehicle comprises 0.15 w/v % to 1.50 w/v % of hyaluronic acid having an average molecular weight of 500,000 to 3,900,000.

7. The method according to claim 1, wherein the vehicle further comprises chondroitin sulfate.

8. The method according to claim 7, wherein the vehicle comprises 0.3 w/v % to 1.0 w/v % of chondroitin sulfate.

9. The method according to claim 1, wherein the vehicle comprises neither an antimicrobial agent nor an antiseptic.

10. The method according to claim 1, wherein the transplant neural retina sheet has a front surface and a back surface, wherein the front surface constitutes an apical surface containing a neural retinal layer, the back surface to the apical surface of the transplant neural retina sheet is from 100 μm to 1000 μm, a major axis of the transplant neural retina sheet is from 600 μm to 2500 μm, and a minor axis of the transplant neural retina sheet is from 200 μm to 1500 μm.

11. The method according to claim 1, wherein the front surface has a smooth shape with less change in curvature, and the back surface has an irregular shape with large change in curvature.

12. The method according to claim 1, wherein the transplant retinal tissue comprises 1 to 30 of the transplant neural retina sheets and 5 to 500 μl of the vehicle for transplantation.

13. The method according to claim 1, wherein the transplant neural retina sheet (1) has been isolated from a cell aggregate containing a neural retinal layer, (2) contains a region of the center and/or its neighborhood of continuous epithelial tissue in the cell aggregate, and (3) is from 600 μm to 2500 μm in major axis, from 200 μm to 1500 μm in minor axis, and from 100 μm to 1000 μm in thickness.

14. The method according to claim 1, wherein the transplant neural retina sheet (1) has been isolated from a cell aggregate containing at least first epithelial tissue and second epithelial tissue, wherein the first epithelial tissue contains a human neural retina, and the second epithelial tissue has the continuity of the slope of a tangent line to a surface different from the continuity of the slope of a tangent line to the surface of the first epithelial tissue, and contains a non-neural retina-related cell, (2) contains a region on the first epithelial tissue most distant from the second epithelial tissue, and (3) is from 600 μm to 2500 μm in major axis, from 200 μm to 1500 μm in minor axis, and from 100 μm to 1000 μm in thickness, wherein the second epithelial tissue is a tissue selected from the group consisting of eyeball-related tissue, brain and spinal cord tissue and other tissues different from the neural retina of the first epithelial tissue.

15. The method according to claim 1, wherein the ratio of a Rx-positive cell to the total number of cells in the transplant neural retina sheet is 30% or more and 80% or less, 40% or more and 70% or less, 45% or more and 60% or less, or 50% or more and 60% or less.

16. The method according to claim 1, wherein the ratio of a Chx10-positive cell to the total number of cells in the transplant neural retina sheet is 10% or more and 80% or less, 20% or more and 70% or less, 30% or more and 60% or less, or 40% or more and 50% or less.

17. The method according to claim 1, wherein the ratio of a Pax6-positive cell to the total number of cells in the transplant neural retina sheet is 10% or more and 80% or less, 20% or more and 70% or less, 30% or more and 60% or less, or 40% or more and 50% or less.

18. The method according to claim 1, wherein the ratio of a Crx-positive cell to the total number of cells in the transplant neural retina sheet is 10% or more and 70% or less, 10% or more and 60% or less, 20% or more and 60% or less, 30% or more and 60% or less, 40% or more and 60% or less, or 50% or more and 60% or less.

19. The method according to claim 1, wherein an apical surface/basal surface direction of the transplant neural retina sheet is maintained.

20. The method according to claim 1, comprising steps of:

(1) preparing a composition comprising 1 to 30 of the transplant neural retina sheets and 5 to 500 μl of the vehicle, (2) aspirating the transplant neural retina sheets into a device for transplantation, and (3) discharging them to a recipient without damaging the neural retina sheets.

21. The method according to claim 20, wherein the composition comprises 3 to 30 of the transplant neural retina sheets.

22. The method according to claim 1, wherein the disease is selected from a group consisting of retinal degenerative diseases, macular degeneration, age-related macular degeneration, retinitis pigmentosa, glaucoma, corneal diseases, retinal detachment, central serous chorioretinopathy, cone dystrophy, and cone rod dystrophy, and the injury is a state in which photoreceptor cells die of degeneration.

* * * * *